(12) United States Patent
Rehm et al.

(10) Patent No.: US 10,501,505 B2
(45) Date of Patent: Dec. 10, 2019

(54) POLYMER PARTICLES AND USES THEREOF

(71) Applicants: Bernd Helmut Adam Rehm, Brisbane (AU); Bryce Malcolm Buddle, Palmerston North (NZ); David Neil Wedlock, Palmerston North (NZ)

(72) Inventors: Bernd Helmut Adam Rehm, Brisbane (AU); Bryce Malcolm Buddle, Palmerston North (NZ); David Neil Wedlock, Palmerston North (NZ)

(*) Notice: Subject to any disclaimer, the term of this patent is extended or adjusted under 35 U.S.C. 154(b) by 10 days.

(21) Appl. No.: 15/116,338

(22) PCT Filed: Feb. 4, 2015

(86) PCT No.: PCT/NZ2015/050008
§ 371 (c)(1),
(2) Date: Aug. 3, 2016

(87) PCT Pub. No.: WO2015/119512
PCT Pub. Date: Aug. 13, 2015

(65) Prior Publication Data
US 2017/0008938 A1    Jan. 12, 2017

(30) Foreign Application Priority Data

Feb. 4, 2014  (NZ) ........................... 620682

(51) Int. Cl.
| | | |
|---|---|---|
| C07K 14/35 | (2006.01) | |
| A61K 39/04 | (2006.01) | |
| A61K 38/44 | (2006.01) | |
| A61K 38/45 | (2006.01) | |
| A61K 38/51 | (2006.01) | |
| C12N 9/10 | (2006.01) | |
| A61K 49/00 | (2006.01) | |
| G01N 33/68 | (2006.01) | |

(52) U.S. Cl.
CPC .............. *C07K 14/35* (2013.01); *A61K 38/44* (2013.01); *A61K 38/45* (2013.01); *A61K 38/51* (2013.01); *A61K 39/04* (2013.01); *A61K 49/0006* (2013.01); *C12N 9/1025* (2013.01); *G01N 33/6866* (2013.01); *G01N 33/6893* (2013.01); *C07K 2319/00* (2013.01); *G01N 2333/35* (2013.01); *G01N 2333/57* (2013.01); *G01N 2800/26* (2013.01)

(58) Field of Classification Search
None
See application file for complete search history.

(56) References Cited

U.S. PATENT DOCUMENTS

| | | |
|---|---|---|
| 5,965,140 A | 10/1999 | Valenzuela et al. |
| 2002/0176867 A1 | 11/2002 | Andersen et al. |
| 2006/0024332 A1 | 2/2006 | Waters et al. |

FOREIGN PATENT DOCUMENTS

| | | |
|---|---|---|
| WO | 2007/037706 A2 | 4/2007 |
| WO | 2011/013097 A2 | 2/2011 |
| WO | 2012/104791 A1 | 8/2012 |
| WO | 2014/009439 A1 | 1/2014 |

OTHER PUBLICATIONS

Shuxiong Chen et al., "New Skin Test for Detection of Bovine Tuberculosis on the Basis of Antigen-Displaying Polyester Inclusions Produced by Recombinant *Escherichia coli*", Applied and Environmental Microbiology, Apr. 2014, pp. 2526-2535, vol. 80, No. 8 (published online Feb. 14, 2014).
International Search Report for PCT/NZ2015/050008 dated Apr. 17, 2015.
Written Opinion for PCT/NZ2015/050008 dated Apr. 17, 2015.
Lin, Jiaming et al., "Fusion Expression on the Esat-6 and cfp-10 Genes of *Mycobacterium bovis* in *Escherichia Coli*" Applied Mechanics and Materials, Sep. 1, 2013, vol. 421, pp. 354-358.
Communication, dated Nov. 22, 2017, issued by the European Patent Office in European Patent Application No. 15746012.

*Primary Examiner* — Brian Gangle
(74) *Attorney, Agent, or Firm* — Sughrue Mion, PLLC

(57) ABSTRACT

The present invention relates to polymer particles and uses thereof. In particular the present invention relates to functionalized polymer particles, processes of production and uses thereof in the diagnosis, treatment or prevention of tuberculosis.

10 Claims, 11 Drawing Sheets

Figure 1:
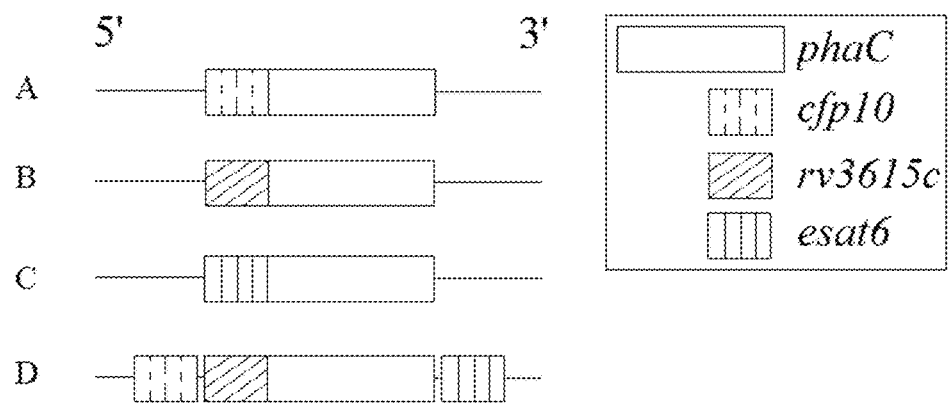

Specification includes a Sequence Listing.

SEQUENCE LISTING

```
<160> NUMBER OF SEQ ID NOS: 22

<210> SEQ ID NO 1
<211> LENGTH: 95
<212> TYPE: PRT
<213> ORGANISM: Mycobacterium bovis
<220> FEATURE:
<221> NAME/KEY: MISC_FEATURE
<223> OTHER INFORMATION: ESAT6 antigen

<400> SEQUEN

```
<211> LENGTH: 103
<212> TYPE: PRT
<213> ORGANISM: Mycobacterium bovis
<220> FEATURE:
<221> NAME/KEY: MISC_FEATURE
<223

```
Arg Asp Val Leu Ala Ala Gly Asp Phe Trp Gly Ala Gly Ser Val
             35                  40                  45

Ala Cys Gln Glu Phe Ile Thr Gln Leu Gly Arg Asn Phe Gln Val Ile
 50                  55                  60

Tyr Glu Gln Ala Asn Ala His Gly Gln Lys Val Gln Ala Ala Gly Asn
 65                  70                  75                  80

Asn Met Ala Gln Thr Asp Ser Ala Val Gly Ser Ser Trp Ala
                 85                  90
```

<210> SEQ ID NO 6
<211> LENGTH: 198
<212> TYPE: PRT
<213> ORGANISM: Artificial Sequence
<220> FEATURE:
<223> OTHER INFORMATION: Synthetic fusion polypeptide
<220> FEATURE:
<221> NAME/KEY: MISC_FEATURE
<223> OTHER INFORMATION: ESAT6-Rv3020c fusion

<400> SEQUENCE: 6

```
Glu Met Thr Glu Gln Gln Trp Asn Phe Ala Gly Ile Glu Ala Ala Ala
 1               5                  10                  15

Ser Ala Ile Gln Gly Asn Val Thr Ser Ile His Ser Leu Leu Asp Glu
                 20                  25                  30

Gly Lys Gln Ser Leu Thr Lys Leu Ala Ala Ala Trp Gly Gly Ser Gly
             35                  40                  45

Ser Glu Ala Tyr Gln Gly Val Gln Gln Lys Trp Asp Ala Thr Ala Thr
 50                  55                  60

Glu Leu Asn Asn Ala Leu Gln Asn Leu Ala Arg Thr Ile Ser Glu Ala
 65                  70                  75                  80

Gly Gln Ala Met Ala Ser Thr Glu Gly Asn Val Thr Gly Met Phe Ala
                 85                  90                  95

Gly Gly Gly Gly Gly Met Ser Leu Leu Asp Ala His Ile Pro Gln Leu
            100                 105                 110

Ile Ala Ser His Thr Ala Phe Ala Ala Lys Ala Gly Leu Met Arg His
            115                 120                 125

Thr Ile Gly Gln Ala Glu Gln Gln Ala Met Ser Ala Gln Ala Phe His
        130                 135                 140

Gln Gly Glu Ser Ala Ala Ala Phe Gln Gly Ala His Ala Arg Phe Val
145                 150                 155                 160

Ala Ala Ala Ala Lys Val Asn Thr Leu Leu Asp Ile Ala Gln Ala Asn
                165                 170                 175

Leu Gly Glu Ala Ala Gly Thr Tyr Val Ala Ala Asp Ala Ala Ala Ala
            180                 185                 190

Ser Ser Tyr Thr Gly Phe
        195
```

<210> SEQ ID NO 7
<211> LENGTH: 690
<212> TYPE: PRT
<213> ORGANISM: Artificial Sequence
<220> FEATURE:
<223> OTHER INFORMATION: Synthetic fusion polypeptide
<220> FEATURE:
<221> NAME/KEY: MISC_FEATURE
<223> OTHER INFORMATION: CFP10-PhaC fusion

<400> SEQUENCE: 7

```
Met Ala Glu Met Lys Thr Asp Ala Ala Thr Leu Ala Gln Glu Ala Gly
 1               5                  10                  15
```

```
Asn Phe Glu Arg Ile Ser Gly Asp Leu Lys Thr Gln Ile Asp Gln Val
                20                  25                  30

Glu Ser Thr Ala Gly Ser Leu Gln Gly Gln Trp Arg Gly Ala Ala Gly
            35                  40                  45

Thr Ala Ala Gln Ala Ala Val Val Arg Phe Gln Glu Ala Ala Asn Lys
 50                  55                  60

Gln Lys Gln Glu Leu Asp Glu Ile Ser Thr Asn Ile Arg Gln Ala Gly
 65                  70                  75                  80

Val Gln Tyr Ser Arg Ala Asp Glu Gln Gln Gln Ala Leu Ser Ser
                85                  90                  95

Gln Met Gly Phe His Met Ala Thr Gly Lys Gly Ala Ala Ala Ser Thr
                100                 105                 110

Gln Glu Gly Lys Ser Gln Pro Phe Lys Val Thr Pro Gly Pro Phe Asp
            115                 120                 125

Pro Ala Thr Trp Leu Glu Trp Ser Arg Gln Trp Gln Gly Thr Glu Gly
 130                 135                 140

Asn Gly His Ala Ala Ser Gly Ile Pro Gly Leu Asp Ala Leu Ala
145                 150                 155                 160

Gly Val Lys Ile Ala Pro Ala Gln Leu Gly Asp Ile Gln Gln Arg Tyr
                165                 170                 175

Met Lys Asp Phe Ser Ala Leu Trp Gln Ala Met Ala Glu Gly Lys Ala
                180                 185                 190

Glu Ala Thr Gly Pro Leu His Asp Arg Arg Phe Ala Gly Asp Ala Trp
            195                 200                 205

Arg Thr Asn Leu Pro Tyr Arg Phe Ala Ala Phe Tyr Leu Leu Asn
 210                 215                 220

Ala Arg Ala Leu Thr Glu Leu Ala Asp Ala Val Glu Ala Asp Ala Lys
225                 230                 235                 240

Thr Arg Gln Arg Ile Arg Phe Ala Ile Ser Gln Trp Val Asp Ala Met
                245                 250                 255

Ser Pro Ala Asn Phe Leu Ala Thr Asn Pro Glu Ala Gln Arg Leu Leu
                260                 265                 270

Ile Glu Ser Gly Gly Glu Ser Leu Arg Ala Gly Val Arg Asn Met Met
                275                 280                 285

Glu Asp Leu Thr Arg Gly Lys Ile Ser Gln Thr Asp Glu Ser Ala Phe
 290                 295                 300

Glu Val Gly Arg Asn Val Ala Val Thr Glu Gly Ala Val Phe Glu
305                 310                 315                 320

Asn Glu Tyr Phe Gln Leu Leu Gln Tyr Lys Pro Leu Thr Asp Lys Val
                325                 330                 335

His Ala Arg Pro Leu Leu Met Val Pro Pro Cys Ile Asn Lys Tyr Tyr
            340                 345                 350

Ile Leu Asp Leu Gln Pro Glu Ser Ser Leu Val Arg His Val Val Glu
 355                 360                 365

Gln Gly His Thr Val Phe Leu Val Ser Trp Arg Asn Pro Asp Ala Ser
 370                 375                 380

Met Ala Gly Ser Thr Trp Asp Asp Tyr Ile Glu His Ala Ala Ile Arg
385                 390                 395                 400

Ala Ile Glu Val Ala Arg Asp Ile Ser Gly Gln Asp Lys Ile Asn Val
                405                 410                 415

Leu Gly Phe Cys Val Gly Gly Thr Ile Val Ser Thr Ala Leu Ala Val
                420                 425                 430
```

```
Leu Ala Ala Arg Gly Glu His Pro Ala Ala Ser Val Thr Leu Leu Thr
            435                 440                 445

Thr Leu Leu Asp Phe Ala Asp Thr Gly Ile Leu Asp Val Phe Val Asp
450                 455                 460

Glu Gly His Val Gln Leu Arg Glu Ala Thr Leu Gly Gly Ala Gly
465                 470                 475                 480

Ala Pro Cys Ala Leu Leu Arg Gly Leu Glu Leu Ala Asn Thr Phe Ser
                485                 490                 495

Phe Leu Arg Pro Asn Asp Leu Val Trp Asn Tyr Val Val Asp Asn Tyr
                500                 505                 510

Leu Lys Gly Asn Thr Pro Val Pro Phe Asp Leu Leu Phe Trp Asn Gly
                515                 520                 525

Asp Ala Thr Asn Leu Pro Gly Pro Trp Tyr Cys Trp Tyr Leu Arg His
            530                 535                 540

Thr Tyr Leu Gln Asn Glu Leu Lys Val Pro Gly Lys Leu Thr Val Cys
545                 550                 555                 560

Gly Val Pro Val Asp Leu Ala Ser Ile Asp Val Pro Thr Tyr Ile Tyr
                565                 570                 575

Gly Ser Arg Glu Asp His Ile Val Pro Trp Thr Ala Ala Tyr Ala Ser
                580                 585                 590

Thr Ala Leu Leu Ala Asn Lys Leu Arg Phe Val Leu Gly Ala Ser Gly
            595                 600                 605

His Ile Ala Gly Val Ile Asn Pro Pro Ala Lys Asn Lys Arg Ser His
            610                 615                 620

Trp Thr Asn Asp Ala Leu Pro Glu Ser Pro Gln Gln Trp Leu Ala Gly
625                 630                 635                 640

Ala Ile Glu His His Gly Ser Trp Trp Pro Asp Trp Thr Ala Trp Leu
                645                 650                 655

Ala Gly Gln Ala Gly Ala Lys Arg Ala Ala Pro Ala Asn Tyr Gly Asn
                660                 665                 670

Ala Arg Tyr Arg Ala Ile Glu Pro Ala Pro Gly Arg Tyr Val Lys Ala
            675                 680                 685

Lys Ala
   690

<210> SEQ ID NO 8
<211> LENGTH: 693
<212> TYPE: PRT
<213> ORGANISM: Artificial Sequence
<220> FEATURE:
<223> OTHER INFORMATION: Synthetic fusion polypeptide
<220> FEATURE:
<221> NAME/KEY: MISC_FEATURE
<223> OTHER INFORMATION: RV3615C-PhaC fusion

<400> SEQUENCE: 8

Met Thr Glu Asn Leu Thr Val Gln Pro Glu Arg Leu Gly Val Leu Ala
1               5                   10                  15

Ser His His Asp Asn Ala Ala Val Asp Ala Ser Ser Gly Val Glu Ala
                20                  25                  30

Ala Ala Gly Leu Gly Glu Ser Val Ala Ile Thr His Gly Pro Tyr Cys
            35                  40                  45

Ser Gln Phe Asn Asp Thr Leu Asn Val Tyr Leu Thr Ala His Asn Ala
        50                  55                  60

Leu Gly Ser Ser Leu His Thr Ala Gly Val Asp Leu Ala Lys Ser Leu
65                  70                  75                  80
```

-continued

```
Arg Ile Ala Ala Lys Ile Tyr Ser Glu Ala Asp Glu Ala Trp Arg Lys
                85                  90                  95
Ala Ile Asp Gly Leu Phe Thr His Met Ala Thr Gly Lys Gly Ala Ala
            100                 105                 110
Ala Ser Thr Gln Glu Gly Lys Ser Gln Pro Phe Lys Val Thr Pro Gly
        115                 120                 125
Pro Phe Asp Pro Ala Thr Trp Leu Glu Trp Ser Arg Gln Trp Gln Gly
    130                 135                 140
Thr Glu Gly Asn Gly His Ala Ala Ser Gly Ile Pro Gly Leu Asp
145                 150                 155                 160
Ala Leu Ala Gly Val Lys Ile Ala Pro Ala Gln Leu Gly Asp Ile Gln
                165                 170                 175
Gln Arg Tyr Met Lys Asp Phe Ser Ala Leu Trp Gln Ala Met Ala Glu
            180                 185                 190
Gly Lys Ala Glu Ala Thr Gly Pro Leu His Asp Arg Arg Phe Ala Gly
        195                 200                 205
Asp Ala Trp Arg Thr Asn Leu Pro Tyr Arg Phe Ala Ala Ala Phe Tyr
    210                 215                 220
Leu Leu Asn Ala Arg Ala Leu Thr Glu Leu Ala Asp Ala Val Glu Ala
225                 230                 235                 240
Asp Ala Lys Thr Arg Gln Arg Ile Arg Phe Ala Ile Ser Gln Trp Val
                245                 250                 255
Asp Ala Met Ser Pro Ala Asn Phe Leu Ala Thr Asn Pro Glu Ala Gln
            260                 265                 270
Arg Leu Leu Ile Glu Ser Gly Gly Glu Ser Leu Arg Ala Gly Val Arg
        275                 280                 285
Asn Met Met Glu Asp Leu Thr Arg Gly Lys Ile Ser Gln Thr Asp Glu
    290                 295                 300
Ser Ala Phe Glu Val Gly Arg Asn Val Ala Val Thr Glu Gly Ala Val
305                 310                 315                 320
Val Phe Glu Asn Glu Tyr Phe Gln Leu Leu Gln Tyr Lys Pro Leu Thr
                325                 330                 335
Asp Lys Val His Ala Arg Pro Leu Leu Met Val Pro Pro Cys Ile Asn
            340                 345                 350
Lys Tyr Tyr Ile Leu Asp Leu Gln Pro Glu Ser Ser Leu Val Arg His
        355                 360                 365
Val Val Glu Gln Gly His Thr Val Phe Leu Val Ser Trp Arg Asn Pro
    370                 375                 380
Asp Ala Ser Met Ala Gly Ser Thr Trp Asp Asp Tyr Ile Glu His Ala
385                 390                 395                 400
Ala Ile Arg Ala Ile Glu Val Ala Arg Asp Ile Ser Gly Gln Asp Lys
                405                 410                 415
Ile Asn Val Leu Gly Phe Cys Val Gly Gly Thr Ile Val Ser Thr Ala
            420                 425                 430
Leu Ala Val Leu Ala Ala Arg Gly Glu His Pro Ala Ala Ser Val Thr
        435                 440                 445
Leu Leu Thr Thr Leu Leu Asp Phe Ala Asp Thr Gly Ile Leu Asp Val
    450                 455                 460
Phe Val Asp Glu Gly His Val Gln Leu Arg Glu Ala Thr Leu Gly Gly
465                 470                 475                 480
Gly Ala Gly Ala Pro Cys Ala Leu Leu Arg Gly Leu Glu Leu Ala Asn
                485                 490                 495
Thr Phe Ser Phe Leu Arg Pro Asn Asp Leu Val Trp Asn Tyr Val Val
```

```
            500                 505                 510

Asp Asn Tyr Leu Lys Gly Asn Thr Pro Val Pro Phe Asp Leu Leu Phe
        515                 520                 525

Trp Asn Gly Asp Ala Thr Asn Leu Pro Gly Pro Trp Tyr Cys Trp Tyr
    530                 535                 540

Leu Arg His Thr Tyr Leu Gln Asn Glu Leu Lys Val Pro Gly Lys Leu
545                 550                 555                 560

Thr Val Cys Gly Val Pro Val Asp Leu Ala Ser Ile Asp Val Pro Thr
                565                 570                 575

Tyr Ile Tyr Gly Ser Arg Glu Asp His Ile Val Pro Trp Thr Ala Ala
            580                 585                 590

Tyr Ala Ser Thr Ala Leu Leu Ala Asn Lys Leu Arg Phe Val Leu Gly
        595                 600                 605

Ala Ser Gly His Ile Ala Gly Val Ile Asn Pro Pro Ala Lys Asn Lys
    610                 615                 620

Arg Ser His Trp Thr Asn Asp Ala Leu Pro Glu Ser Pro Gln Gln Trp
625                 630                 635                 640

Leu Ala Gly Ala Ile Glu His His Gly Ser Trp Trp Pro Asp Trp Thr
                645                 650                 655

Ala Trp Leu Ala Gly Gln Ala Gly Ala Lys Arg Ala Ala Pro Ala Asn
            660                 665                 670

Tyr Gly Asn Ala Arg Tyr Arg Ala Ile Glu Pro Ala Pro Gly Arg Tyr
        675                 680                 685

Val Lys Ala Lys Ala
    690

<210> SEQ ID NO 9
<211> LENGTH: 685
<212> TYPE: PRT
<213> ORGANISM: Artificial Sequence
<220> FEATURE:
<223> OTHER INFORMATION: Synthetic fusion polypeptide
<220> FEATURE:
<221> NAME/KEY: MISC_FEATURE
<223> OTHER INFORMATION: ESAT6-PhaC fusion

<400> SEQUENCE: 9

Met Thr Glu Gln Gln Trp Asn Phe Ala Gly Ile Glu Ala Ala Ala Ser
1               5                   10                  15

Ala Ile Gln Gly Asn Val Thr Ser Ile His Ser Leu Leu Asp Glu Gly
            20                  25                  30

Lys Gln Ser Leu Thr Lys Leu Ala Ala Ala Trp Gly Gly Ser Gly Ser
        35                  40                  45

Glu Ala Tyr Gln Gly Val Gln Gln Lys Trp Asp Ala Thr Ala Thr Glu
    50                  55                  60

Leu Asn Asn Ala Leu Gln Asn Leu Ala Arg Thr Ile Ser Glu Ala Gly
65                  70                  75                  80

Gln Ala Met Ala Ser Thr Glu Gly Asn Val Thr Gly Met Phe Ala His
                85                  90                  95

Met Ala Thr Gly Lys Gly Ala Ala Ala Ser Thr Gln Glu Gly Lys Ser
            100                 105                 110

Gln Pro Phe Lys Val Thr Pro Gly Pro Phe Asp Pro Ala Thr Trp Leu
        115                 120                 125

Glu Trp Ser Arg Gln Trp Gln Gly Thr Glu Gly Asn Gly His Ala Ala
    130                 135                 140

Ala Ser Gly Ile Pro Gly Leu Asp Ala Leu Ala Gly Val Lys Ile Ala
```

```
            145                 150                 155                 160
        Pro Ala Gln Leu Gly Asp Ile Gln Gln Arg Tyr Met Lys Asp Phe Ser
                        165                 170                 175
        Ala Leu Trp Gln Ala Met Ala Glu Gly Lys Ala Glu Ala Thr Gly Pro
                        180                 185                 190
        Leu His Asp Arg Arg Phe Ala Gly Asp Ala Trp Arg Thr Asn Leu Pro
                        195                 200                 205
        Tyr Arg Phe Ala Ala Ala Phe Tyr Leu Leu Asn Ala Arg Ala Leu Thr
                        210                 215                 220
        Glu Leu Ala Asp Ala Val Glu Ala Asp Ala Lys Thr Arg Gln Arg Ile
        225                 230                 235                 240
        Arg Phe Ala Ile Ser Gln Trp Val Asp Ala Met Ser Pro Ala Asn Phe
                        245                 250                 255
        Leu Ala Thr Asn Pro Glu Ala Gln Arg Leu Leu Ile Glu Ser Gly Gly
                        260                 265                 270
        Glu Ser Leu Arg Ala Gly Val Arg Asn Met Met Glu Asp Leu Thr Arg
                        275                 280                 285
        Gly Lys Ile Ser Gln Thr Asp Glu Ser Ala Phe Glu Val Gly Arg Asn
                        290                 295                 300
        Val Ala Val Thr Glu Gly Ala Val Val Phe Glu Asn Glu Tyr Phe Gln
        305                 310                 315                 320
        Leu Leu Gln Tyr Lys Pro Leu Thr Asp Lys Val His Ala Arg Pro Leu
                        325                 330                 335
        Leu Met Val Pro Pro Cys Ile Asn Lys Tyr Tyr Ile Leu Asp Leu Gln
                        340                 345                 350
        Pro Glu Ser Ser Leu Val Arg His Val Val Glu Gln Gly His Thr Val
                        355                 360                 365
        Phe Leu Val Ser Trp Arg Asn Pro Asp Ala Ser Met Ala Gly Ser Thr
                        370                 375                 380
        Trp Asp Asp Tyr Ile Glu His Ala Ala Ile Arg Ala Ile Glu Val Ala
        385                 390                 395                 400
        Arg Asp Ile Ser Gly Gln Asp Lys Ile Asn Val Leu Gly Phe Cys Val
                        405                 410                 415
        Gly Gly Thr Ile Val Ser Thr Ala Leu Ala Val Leu Ala Ala Arg Gly
                        420                 425                 430
        Glu His Pro Ala Ala Ser Val Thr Leu Leu Thr Thr Leu Leu Asp Phe
                        435                 440                 445
        Ala Asp Thr Gly Ile Leu Asp Val Phe Val Asp Glu Gly His Val Gln
                        450                 455                 460
        Leu Arg Glu Ala Thr Leu Gly Gly Ala Gly Ala Pro Cys Ala Leu
        465                 470                 475                 480
        Leu Arg Gly Leu Glu Leu Ala Asn Thr Phe Ser Phe Leu Arg Pro Asn
                        485                 490                 495
        Asp Leu Val Trp Asn Tyr Val Val Asp Asn Tyr Leu Lys Gly Asn Thr
                        500                 505                 510
        Pro Val Pro Phe Asp Leu Leu Phe Trp Asn Gly Asp Ala Thr Asn Leu
                        515                 520                 525
        Pro Gly Pro Trp Tyr Cys Trp Tyr Leu Arg His Thr Tyr Leu Gln Asn
                        530                 535                 540
        Glu Leu Lys Val Pro Gly Lys Leu Thr Val Cys Gly Val Pro Val Asp
        545                 550                 555                 560
        Leu Ala Ser Ile Asp Val Pro Thr Tyr Ile Tyr Gly Ser Arg Glu Asp
                        565                 570                 575
```

```
His Ile Val Pro Trp Thr Ala Ala Tyr Ala Ser Thr Ala Leu Leu Ala
            580                 585                 590

Asn Lys Leu Arg Phe Val Leu Gly Ala Ser Gly His Ile Ala Gly Val
            595                 600                 605

Ile Asn Pro Pro Ala Lys Asn Lys Arg Ser His Trp Thr Asn Asp Ala
610                 615                 620

Leu Pro Glu Ser Pro Gln Gln Trp Leu Ala Gly Ala Ile Glu His His
625                 630                 635                 640

Gly Ser Trp Trp Pro Asp Trp Thr Ala Trp Leu Ala Gly Gln Ala Gly
                645                 650                 655

Ala Lys Arg Ala Ala Pro Ala Asn Tyr Gly Asn Ala Arg Tyr Arg Ala
            660                 665                 670

Ile Glu Pro Ala Pro Gly Arg Tyr Val Lys Ala Lys Ala
            675                 680                 685

<210> SEQ ID NO 10
<211> LENGTH: 914
<212> TYPE: PRT
<213> ORGANISM: Artificial Sequence
<220> FEATURE:
<223> OTHER INFORMATION: Synthetic fusion polypeptide
<220> FEATURE:
<221> NAME/KEY: MISC_FEATURE
<223> OTHER INFORMATION: CFP10-RV3615C-PhaC-ESAT6 fusion

<400> SEQUENCE: 10

Met Ala Glu Met Lys Thr Asp Ala Ala Thr Leu Ala Gln Glu Ala Gly
1               5                   10                  15

Asn Phe Glu Arg Ile Ser Gly Asp Leu Lys Thr Gln Ile Asp Gln Val
            20                  25                  30

Glu Ser Thr Ala Gly Ser Leu Gln Gly Gln Trp Arg Gly Ala Ala Gly
        35                  40                  45

Thr Ala Ala Gln Ala Ala Val Val Arg Phe Gln Glu Ala Ala Asn Lys
    50                  55                  60

Gln Lys Gln Glu Leu Asp Glu Ile Ser Thr Asn Ile Arg Gln Ala Gly
65                  70                  75                  80

Val Gln Tyr Ser Arg Ala Asp Glu Glu Gln Gln Gln Ala Leu Ser Ser
                85                  90                  95

Gln Met Gly Phe Gly Pro Gly Gly Gly Gly Pro Met Thr Glu Asn
            100                 105                 110

Leu Thr Val Gln Pro Glu Arg Leu Gly Val Leu Ala Ser His His Asp
            115                 120                 125

Asn Ala Ala Val Asp Ala Ser Ser Gly Val Glu Ala Ala Gly Leu
    130                 135                 140

Gly Glu Ser Val Ala Ile Thr His Gly Pro Tyr Cys Ser Gln Phe Asn
145                 150                 155                 160

Asp Thr Leu Asn Val Tyr Leu Thr Ala His Asn Ala Leu Gly Ser Ser
                165                 170                 175

Leu His Thr Ala Gly Val Asp Leu Ala Lys Ser Leu Arg Ile Ala Ala
            180                 185                 190

Lys Ile Tyr Ser Glu Ala Asp Glu Ala Trp Arg Lys Ala Ile Asp Gly
            195                 200                 205

Leu Phe Thr Thr Ser Ala Thr Gly Lys Gly Ala Ala Ala Ser Thr Gln
        210                 215                 220

Glu Gly Lys Ser Gln Pro Phe Lys Val Thr Pro Gly Pro Phe Asp Pro
225                 230                 235                 240
```

```
Ala Thr Trp Leu Glu Trp Ser Arg Gln Trp Gln Gly Thr Glu Gly Asn
            245                 250                 255

Gly His Ala Ala Ala Ser Gly Ile Pro Gly Leu Asp Ala Leu Ala Gly
            260                 265                 270

Val Lys Ile Ala Pro Ala Gln Leu Gly Asp Ile Gln Gln Arg Tyr Met
            275                 280                 285

Lys Asp Phe Ser Ala Leu Trp Gln Ala Met Ala Glu Gly Lys Ala Glu
            290                 295                 300

Ala Thr Gly Pro Leu His Asp Arg Arg Phe Ala Gly Asp Ala Trp Arg
305                 310                 315                 320

Thr Asn Leu Pro Tyr Arg Phe Ala Ala Phe Tyr Leu Leu Asn Ala
            325                 330                 335

Arg Ala Leu Thr Glu Leu Ala Asp Ala Val Glu Ala Asp Ala Lys Thr
            340                 345                 350

Arg Gln Arg Ile Arg Phe Ala Ile Ser Gln Trp Val Asp Ala Met Ser
            355                 360                 365

Pro Ala Asn Phe Leu Ala Thr Asn Pro Glu Ala Gln Arg Leu Leu Ile
            370                 375                 380

Glu Ser Gly Gly Glu Ser Leu Arg Ala Gly Val Arg Asn Met Met Glu
385                 390                 395                 400

Asp Leu Thr Arg Gly Lys Ile Ser Gln Thr Asp Glu Ser Ala Phe Glu
            405                 410                 415

Val Gly Arg Asn Val Ala Val Thr Glu Gly Ala Val Val Phe Glu Asn
            420                 425                 430

Glu Tyr Phe Gln Leu Leu Gln Tyr Lys Pro Leu Thr Asp Lys Val His
            435                 440                 445

Ala Arg Pro Leu Leu Met Val Pro Pro Cys Ile Asn Lys Tyr Tyr Ile
450                 455                 460

Leu Asp Leu Gln Pro Glu Ser Ser Leu Val Arg His Val Val Glu Gln
465                 470                 475                 480

Gly His Thr Val Phe Leu Val Ser Trp Arg Asn Pro Asp Ala Ser Met
            485                 490                 495

Ala Gly Ser Thr Trp Asp Asp Tyr Ile Glu His Ala Ala Ile Arg Ala
            500                 505                 510

Ile Glu Val Ala Arg Asp Ile Ser Gly Gln Asp Lys Ile Asn Val Leu
            515                 520                 525

Gly Phe Cys Val Gly Gly Thr Ile Val Ser Thr Ala Leu Ala Val Leu
            530                 535                 540

Ala Ala Arg Gly Glu His Pro Ala Ala Ser Val Thr Leu Leu Thr Thr
545                 550                 555                 560

Leu Leu Asp Phe Ala Asp Thr Gly Ile Leu Asp Val Phe Val Asp Glu
            565                 570                 575

Gly His Val Gln Leu Arg Glu Ala Thr Leu Gly Gly Ala Gly Ala
            580                 585                 590

Pro Cys Ala Leu Leu Arg Gly Leu Glu Leu Ala Asn Thr Phe Ser Phe
            595                 600                 605

Leu Arg Pro Asn Asp Leu Val Trp Asn Tyr Val Val Asp Asn Tyr Leu
            610                 615                 620

Lys Gly Asn Thr Pro Val Pro Phe Asp Leu Leu Phe Trp Asn Gly Asp
625                 630                 635                 640

Ala Thr Asn Leu Pro Gly Pro Trp Tyr Cys Trp Tyr Leu Arg His Thr
            645                 650                 655
```

```
Tyr Leu Gln Asn Glu Leu Lys Val Pro Gly Lys Leu Thr Val Cys Gly
                660                 665                 670

Val Pro Val Asp Leu Ala Ser Ile Asp Val Pro Thr Tyr Ile Tyr Gly
            675                 680                 685

Ser Arg Glu Asp His Ile Val Pro Trp Thr Ala Ala Tyr Ala Ser Thr
        690                 695                 700

Ala Leu Leu Ala Asn Lys Leu Arg Phe Val Leu Gly Ala Ser Gly His
705                 710                 715                 720

Ile Ala Gly Val Ile Asn Pro Pro Ala Lys Asn Lys Arg Ser His Trp
                725                 730                 735

Thr Asn Asp Ala Leu Pro Glu Ser Pro Gln Gln Trp Leu Ala Gly Ala
            740                 745                 750

Ile Glu His His Gly Ser Trp Trp Pro Asp Trp Thr Ala Trp Leu Ala
        755                 760                 765

Gly Gln Ala Gly Ala Lys Arg Ala Ala Pro Ala Asn Tyr Gly Asn Ala
770                 775                 780

Arg Tyr Arg Ala Ile Glu Pro Ala Pro Gly Arg Tyr Val Lys Ala Lys
785                 790                 795                 800

Ala His Met Val Leu Ala Val Ala Ile Asp Lys Arg Gly Gly Gly Gly
                805                 810                 815

Gly Leu Glu Met Thr Glu Gln Gln Trp Asn Phe Ala Gly Ile Glu Ala
            820                 825                 830

Ala Ala Ser Ala Ile Gln Gly Asn Val Thr Ser Ile His Ser Leu Leu
835                 840                 845

Asp Glu Gly Lys Gln Ser Leu Thr Lys Leu Ala Ala Trp Gly Gly
            850                 855                 860

Ser Gly Ser Glu Ala Tyr Gln Gly Val Gln Gln Lys Trp Asp Ala Thr
865                 870                 875                 880

Ala Thr Glu Leu Asn Asn Ala Leu Gln Asn Leu Ala Arg Thr Ile Ser
                885                 890                 895

Glu Ala Gly Gln Ala Met Ala Ser Thr Glu Gly Asn Val Thr Gly Met
            900                 905                 910

Phe Ala
```

<210> SEQ ID NO 11
<211> LENGTH: 606
<212> TYPE: DNA
<213> ORGANISM: Artificial Sequence
<220> FEATURE:
<223> OTHER INFORMATION: Synthetic sequence encoding ESAT6-Rv3020c
      fusion polypeptide

<400> SEQUENCE: 11

```
ctcgagatga cggaacaaca atggaacttt gctggcatcg aagccgccgc atctgctatt      60
caaggcaatg tgacctctat ccactcgctg ctggatgaag caaacagag tctgaccaaa     120 ctggcagcag catggggcgg tagcggctct gaagcctatc aaggtgtgca gcaaaaatgg     180
gacgctaccg cgacggaact gaacaatgcc ctgcagaacc tggcacgtac gatttctgaa     240
gcaggtcaag ctatggcaag cacggaaggc aatgtcacgg gcatgttcgc aggcggcggc     300
ggcggcatga gcctgctgga tgcgcatatt ccgcagctga ttgcgagcca taccgcgttt     360
gcggcgaaag cgggcctgat gcgtcatacc attggccagg cggaacagca ggcgatgagc     420
gcgcaggcgt tcatcaggg cgaaagcgcg cggcgtttc agggcgcgca tgcgcgtttt     480
gtggcggcgc cggcgaaagt gaacaccctg ctggatattg cgcaggcgaa cctgggcgaa     540
```

| gcggcgggca cctatgtggc ggcggatgcg gcggcggcga gcagctatac cggcttttaa | 600 |
| ggatcc | 606 |

<210> SEQ ID NO 12
<211> LENGTH: 2073
<212> TYPE: DNA
<213> ORGANISM: Artificial Sequence
<220> FEATURE:
<223> OTHER INFORMATION: Synthetic sequence encoding CFP10-PhaC fusion
      polypeptide

<400> SEQUENCE: 12

| atggcagaaa tgaaaacgga tgcggcgacc ctggcacaag aagcgggcaa ctttgaacgt | 60 |
| attagcggcg acctgaaaac ccaaatcgat caggttgaaa gcaccgcggg ttctctgcaa | 120 |
| ggccagtggc gtggtgcggc cggtacggca gctcaagcgg ccgtggttcg ctttcaggaa | 180 |
| gcagctaaca acaaaaaca ggaactggat gaaatttcaa ccaatatccg tcaagccggc | 240 |
| gtgcagtatt cgcgcgcaga cgaagaacag caacaggctc tgagctctca aatgggtttc | 300 |
| catatggcga ccggcaaagg cgcggcagct tccacgcagg aaggcaagtc ccaaccattc | 360 |
| aaggtcacgc cggggccatt cgatccagcc acatggctgg aatggtcccg ccagtggcag | 420 |
| ggcactgaag gcaacggcca cgcggccgcg tccggcattc cgggcctgga tgcgctggca | 480 |
| ggcgtcaaga tcgcgccggc gcagctgggt gatatccagc agcgctacat gaaggacttc | 540 |
| tcagcgctgt ggcaggccat ggccgagggc aaggccgagg ccaccggtcc gctgcacgac | 600 |
| cggcgcttcg ccggcgacgc atggcgcacc aacctcccat atcgcttcgc tgccgcgttc | 660 |
| tacctgctca atgcgcgcgc cttgaccgag ctggccgatg ccgtcgaggc cgatgccaag | 720 |
| acccgccagc gcatccgctt cgcgatctcg caatgggtcg atgcgatgtc gcccgccaac | 780 |
| ttccttgcca ccaatcccga ggcgcagcgc ctgctgatcg agtcgggcgg cgaatcgctg | 840 |
| cgtgccggcg tgcgcaacat gatggaagac ctgacacgcg gcaagatctc gcagaccgac | 900 |
| gagagcgcgt ttgaggtcgg ccgcaatgtc gcggtgaccg aaggcgccgt ggtcttcgag | 960 |
| aacgagtact ccagctgttt gcagtacaag ccgctgaccg acaaggtgca cgcgcgcccg | 1020 |
| ctgctgatgg tgccgccgtg catcaacaag tactacatcc tggacctgca gccggagagc | 1080 |
| tcgctggtgc gccatgtggt ggagcaggga catacggtgt ttctggtgtc gtggcgcaat | 1140 |
| ccggacgcca gcatggccgg cagcacctgg gacgactaca tcgagcacgc ggccatccgc | 1200 |
| gccatcgaag tcgcgcgcga catcagcggc caggacaaga tcaacgtgct cggcttctgc | 1260 |
| gtgggcggca ccattgtctc gaccgcgctg gcggtgctgg ccgcgcgcgg cgagcacccg | 1320 |
| gccgccagcg tcacgctgct gaccacgctg ctggactttg ccgacacggg catcctcgac | 1380 |
| gtctttgtcg acgagggcca tgtgcagttg cgcgaggcca cgctgggcgg cggcgccggc | 1440 |
| gcgccgtgcg cgctgctgcg cggccttgag ctggccaata ccttctcgtt cttgcgcccg | 1500 |
| aacgacctgg tgtggaacta cgtggtcgac aactacctga aggcaacac gccggtgccg | 1560 |
| ttcgacctgc tgttctggaa cggcgacgcc accaacctgc cggggccgtg gtactgctgg | 1620 |
| tacctgcgcc acacctacct gcagaacgag ctcaaggtac cggcaagct gaccgtgtgc | 1680 |
| ggcgtgccgg tggacctggc cagcatcgac gtgccgacct atatctacgg ctcgcgcgaa | 1740 |
| gaccatatcg tgccgtggac gcggccctat gcctcgaccg cgctgctggc gaacaagctg | 1800 |
| cgcttcgtgc tgggtgcgtc gggccatatc gccggtgtga tcaacccgcc ggccaagaac | 1860 |
| aagcgcagcc actggactaa cgatgcgctg ccggagtcgc cgcagcaatg gctggccggc | 1920 |

```
gccatcgagc atcacggcag ctggtggccg gactggaccg catggctggc cgggcaggcc    1980
ggcgcgaaac gcgccgcgcc cgccaactat ggcaatgcgc gctatcgcgc aatcgaaccc    2040
gcgcctgggc gatacgtcaa agccaaggca tga                                 2073

<210> SEQ ID NO 13
<211> LENGTH: 2085
<212> TYPE: DNA
<213> ORGANISM: Artificial Sequence
<220> FEATURE:
<223> OTHER INFORMATION: Synthetic sequence encoding Rv3615c-PhaC fusion
      polypeptide

<400> SEQUENCE: 13
atgatgaccg aaaacctgac ggttcagccg aacgtctggg tgtcctggc aagtcatcac       60 gataatgcag cagtcgacgc cagttccggt gtggaagcag ctgcaggtct gggtgaaagt     120
gtggcgatta cccatggtcc gtattgctcc cagtttaacg ataccctgaa tgtttacctg     180
acggcccata cgcactgggt tcatcgctca cacggctgtg tcgacct ggcaaaatct       240 ctgcgcatcg ccgcaaaaat ctattcagaa gcagacgaag cgtggcgtaa agcaatcgac     300
ggcctgttca cccatatggc gaccggcaaa ggcgcggcac ttccacgca ggaaggcaag      360 tcccaaccat tcaaggtcac gccggggcca ttcgatccag ccacatggct ggaatggtcc     420
cgccagtggc agggcactga aggcaacggc cacgcggccg cgtccggcat tccgggcctg     480
gatgcgctgg caggcgtcaa gatcgcgccg gcgcagctgg gtgatatcca gcagcgctac     540
atgaaggact tctcagcgct gtggcaggcc atggccgagg caaggccga ggccaccggt      600 ccgctgcacg accggcgctt cgccggcgac gcatggcgca ccaacctccc atatcgcttc     660
gctgccgcgt tctacctgct caatgcgcgc gccttgaccg agctggccga tgccgtcgag     720
gccgatgcca agacccgcca gcgcatccgc ttcgcgatct cgcaatgggt cgatgcgatg     780
tcgcccgcca acttccttgc caccaatccc gaggcgcagc gcctgctgat cgagtcgggc     840
ggcgaatcgc tgcgtgccgg cgtgcgcaac atgatggaag acctgacacg cggcaagatc     900
tcgcagaccg acgagagcgc gtttgaggtc ggccgcaatg tcgcggtgac cgaaggcgcc     960
gtggtcttcg agaacgagta cttccagctg ttgcagtaca agccgctgac cgacaaggtg    1020
cacgcgcgcc cgctgctgat ggtgccgccg tgcatcaaca agtactacat cctggacctg    1080
cagccggaga gctcgctggt gcgccatgtg gtggagcagg acatacggt gtttctggtg     1140 tcgtggcgca atccggacgc cagcatggcc ggcagcacct gggacgacta catcgagcac    1200
gcggccatcc gcgccatcga agtcgcgcgc gacatcagcg ccaggacaa gatcaacgtg    1260 ctcggcttct gcgtgggcgg caccattgtc tcgaccgcgc tggcggtgct ggccgcgcgc    1320
ggcgagcacc cggccgccag cgtcacgctg ctgaccacgc tgctggactt tgccgacacg    1380
ggcatcctcg acgtctttgt cgacgagggc catgtgcagt gcgcgaggc cacgctgggc    1440 ggcggcgccg cgcgccgtg cgcgctgctg cgcggcttg agctggccaa taccttctcg     1500
ttcttgcgcc cgaacgacct ggtgtggaac tacgtggtcg acaactacct gaagggcaac    1560
acgccggtgc cgttcgacct gctgttctgg aacggcgacg ccaccaacct gccggggccg    1620
tggtactgct ggtacctgcg ccacacctac ctgcagaacg agctcaaggt accgggcaag    1680
ctgaccgtgt gcggcgtgcc ggtggacctg gccagcatcg acgtgccgac ctatatctac    1740
ggctcgcgcg aagaccatat cgtgccgtgg accgcggcct atgcctcgac cgcgctgctg    1800
gcgaacaagc tgcgcttcgt gctgggtgcg tcgggccata tcgccggtgt gatcaacccg    1860
```

```
ccggccaaga acaagcgcag ccactggact aacgatgcgc tgccggagtc gccgcagcaa   1920
tggctggccg gcgccatcga gcatcacggc agctggtggc cggactggac cgcatggctg   1980
gccgggcagg ccggcgcgaa acgcgccgcg cccgccaact atggcaatgc gcgctatcgc   2040
gcaatcgaac ccgcgcctgg gcgatacgtc aaagccaagg catga                   2085
```

<210> SEQ ID NO 14
<211> LENGTH: 2058
<212> TYPE: DNA
<213> ORGANISM: Artificial Sequence
<220> FEATURE:
<223> OTHER INFORMATION: Synthetic sequence encoding ESAT6-PhaC fusion polypeptide

<400> SEQUENCE: 14

```
atgacggaac aacaatggaa ctttgctggc atcgaagccg ccgcatctgc tattcaaggc     60
aatgtgacct ctatccactc gctgctggat gaaggcaaac agagtctgac caaactggca    120
gcagcatggg gcggtagcgg ctctgaagcc tatcaaggtg tgcagcaaaa atgggacgct    180
accgcgacgg aactgaacaa tgccctgcag aacctggcac gtacgatttc tgaagcaggt    240
caagctatgg caagcacgga aggcaatgtc acgggcatgt tcgcacatat ggcgaccggc    300
aaaggcgcgg cagcttccac gcaggaaggc aagtcccaac cattcaaggt cacgccgggg    360
ccattcgatc cagccacatg gctggaatgg tcccgccagt ggcagggcac tgaaggcaac    420
ggccacgcgg ccgcgtccgg cattccgggc ctggatgcgc tggcaggcgt caagatcgcg    480
ccggcgcagc tgggtgatat ccagcagcgc tacatgaagg acttctcagc gctgtggcag    540
gccatggccg agggcaaggc cgaggccacc ggtccgctgc acgaccggcg cttcgccggc    600
gacgcatggc gcaccaacct cccatatcgc ttcgctgccg cgttctacct gctcaatgcg    660
cgcgccttga ccgagctggc cgatgccgtc gaggccgatg ccaagacccg ccagcgcatc    720
cgcttcgcga tctcgcaatg ggtcgatgcg atgtcgcccg ccaacttcct tgccaccaat    780
cccgaggcgc agcgcctgct gatcgagtcg ggcggcgaat cgctgcgtgc cggcgtgcgc    840
aacatgatgg aagacctgac acgcggcaag atctcgcaga ccgacgagag cgcgtttgag    900
gtcggccgca atgtcgcggt gaccgaaggc gccgtggtct tcgagaacga gtacttccag    960
ctgttgcagt acaagccgct gaccgacaag gtgcacgcgc gcccgctgct gatggtgccg   1020
ccgtgcatca acaagtacta catcctggac ctgcagccgg agagctcgct ggtgcgccat   1080
gtggtggagc agggacatac ggtgtttctg gtgtcgtggc gcaatccgga cgccagcatg   1140
gccggcagca cctgggacga ctacatcgag cacgcggcca tccgcgccat cgaagtcgcg   1200
cgcgacatca gcggccagga caagatcaac gtgctcggct tctgcgtggg cggcaccatt   1260
gtctcgaccg cgctggcggt gctggccgcg cgcggcgagc acccggccgc cagcgtcacg   1320
ctgctgacca cgctgctgga ctttgccgac acgggcatcc tcgacgtctt tgtcgacgag   1380
ggccatgtgc agttgcgcga ggccacgctg ggcggcggcg ccggcgcgcc gtgcgcgctg   1440
ctgcgcggcc ttgagctggc caataccttc tcgttcttgc gcccgaacga cctggtgtgg   1500
aactacgtgg tcgacaacta cctgaagggc aacacgccgg tgccgttcga cctgctgttc   1560
tggaacggcg acgccaccaa cctgccgggg ccgtggtact gctggtacct gcgccacacc   1620
tacctgcaga acgagctcaa ggtaccgggc aagctgaccg tgtgcggcgt gccggtggac   1680
ctggccagca tcgacgtgcc gacctatatc tacggctcgc gcgaagacca tatcgtgccg   1740
tggaccgcgg cctatgcctc gaccgcgctg ctggcgaaca agctgcgctt cgtgctgggt   1800
```

```
gcgtcgggcc atatcgccgg tgtgatcaac ccgccggcca agaacaagcg cagccactgg    1860
actaacgatg cgctgccgga gtcgccgcag caatggctgg ccggcgccat cgagcatcac    1920
ggcagctggt ggccggactg gaccgcatgg ctggccgggc aggccggcgc gaaacgcgcc    1980
gcgcccgcca actatggcaa tgcgcgctat cgcgcaatcg aacccgcgcc tgggcgatac    2040
gtcaaagcca aggcatga                                                  2058
```

<210> SEQ ID NO 15
<211> LENGTH: 2745
<212> TYPE: DNA
<213> ORGANISM: Artificial Sequence
<220> FEATURE:
<223> OTHER INFORMATION: Synthetic sequence encoding CFP10-Rv3615c-PhaC-
      ESAT6 fusion polypeptide

<400> SEQUENCE: 15

```
atggcagaaa tgaaaacgga tgcggcgacc ctggcacaag aagcgggcaa ctttgaacgt     60
attagcggcg acctgaaaac ccaaatcgat caggttgaaa gcaccgcggg ttctctgcaa    120
ggccagtggc gtggtgcggc cggtacggca gctcaagcgg ccgtggttcg ctttcaggaa    180
gcagctaaca acaaaaaaca ggaactggat gaaatttcaa ccaatatccg tcaagccggc    240
gtgcagtatt cgcgcgcaga cgaagaacag caacaggctc tgagctctca aatgggtttc    300
gggcccggcg gtggcggtgg cccgatgacc gaaaacctga cggttcagcc ggaacgtctg    360
ggtgtcctgg caagtcatca cgataatgca gcagtcgacg ccagttccgg tgtggaagca    420
gctgcaggtc tgggtgaaag tgtggcgatt acccatggtc cgtattgctc ccagtttaac    480
gataccctga atgtttacct gacggcccat aacgcactgg gttcatcgct gcacacggct    540
ggtgtcgacc tggcaaaatc tctgcgcatc gccgcaaaaa tctattcaga agcagacgaa    600
gcgtggcgta agcaatcga cggcctgttc accactagtg cgaccggcaa aggcgcggca    660
gcttccacgc aggaaggcaa gtcccaacca ttcaaggtca cgccggggcc attcgatcca    720
gccacatggc tggaatggtc ccgccagtgg cagggcactg aaggcaacgg ccacgcggcc    780
gcgtccggca ttccgggcct ggatgcgctg caggcgtca agatcgcgcc ggcgcagctg    840
ggtgatatcc agcagcgcta catgaaggac ttctcagcgc tgtggcaggc catggccgag    900
ggcaaggccg aggccaccgg tccgctgcac gaccggcgct cgccggcga cgcatggcgc    960 accaacctcc catatcgctt cgctgccgcg ttctacctgc tcaatgcgcg cgccttgacc   1020
gagctggccg atgccgtcga ggccgatgcc aagacccgcc agcgcatccg cttcgcgatc   1080
tcgcaatggg tcgatgcgat gtcgcccgcc aacttccttg ccaccaatcc cgaggcgcag   1140
cgcctgctga tcgagtcggg cggcgaatcg ctgcgtgccg gcgtgcgcaa catgatggaa   1200
gacctgacac gcggcaagat ctcgcagacc gacgagagcg cgtttgaggt cggccgcaat   1260
gtcgcggtga ccgaaggcgc cgtggtcttc gagaacgagt acttccagct gttgcagtac   1320
aagccgctga ccgacaaggt gcacgcgcgc ccgctgctga tggtgccgcc gtgcatcaac   1380
aagtactaca tcctggacct gcagccggag agctcgctgg tgcgccatgt ggtggagcag   1440
ggacatacgg tgtttctggt gtcgtggcgc aatccggacg ccagcatggc cggcagcacc   1500
tgggacgact acatcgagca gcggccatc cgcgccatcg aagtcgcgcg cgacatcagc   1560
ggccaggaca agatcaacgt gctcggcttc tgcgtgggcg gcaccattgt ctcgaccgcg   1620
ctggcggtgc tggccgcgcg cggcgagcac ccggccgcca cgtcacgct gctgaccacg   1680 ctgctggact tgccgacac gggcatcctc gacgtctttg tcgacgaggg ccatgtgcag   1740
```

```
ttgcgcgagg ccacgctggg cggcggcgcc ggcgcgccgt gcgcgctgct gcgcggcctt   1800
gagctggcca ataccttctc gttcttgcgc ccgaacgacc tggtgtggaa ctacgtggtc   1860
gacaactacc tgaagggcaa cacgccggtg ccgttcgacc tgctgttctg gaacggcgac   1920
gccaccaacc tgccggggcc gtggtactgc tggtacctgc gccacaccta cctgcagaac   1980
gagctcaagg taccgggcaa gctgaccgtg tgcggcgtgc cggtggacct ggccagcatc   2040
gacgtgccga cctatatcta cggctcgcgc gaagaccata tcgtgccgtg gaccgcggcc   2100
tatgcctcga ccgcgctgct ggcgaacaag ctgcgcttcg tgctgggtgc gtcgggccat   2160
atcgccggtg tgatcaaccc gccggccaag aacaagcgca gccactggac taacgatgcg   2220
ctgccggagt cgccgcagca atggctggcc ggcgccatcg agcatcacgg cagctggtgg   2280
ccggactgga ccgcatggct ggccgggcag gccggcgcga acgcgccgc gcccgccaac   2340 tatggcaatg cgcgctatcg cgcaatcgaa cccgcgcctg ggcgatacgt caaagccaag   2400
gcacatatgg tgctggcggt ggcgattgat aaacgcggag gcggtggagg cctcgagatg   2460
acggaacaac aatggaactt tgctggcatc gaagccgccg catctgctat tcaaggcaat   2520
gtgacctcta tccactcgct gctggatgaa ggcaaacaga gtctgaccaa actggcagca   2580
gcatggggcg gtagcggctc tgaagcctat caaggtgtgc agcaaaaatg ggacgctacc   2640
gcgacggaac tgaacaatgc cctgcagaac ctggcacgta cgatttctga agcaggtcaa   2700
gctatggcaa gcacggaagg caatgtcacg ggcatgttcg cataa              2745

<210> SEQ ID NO 16
<211> LENGTH: 31
<212> TYPE: DNA
<213> ORGANISM: Artificial Sequence
<220> FEATURE:
<223> OTHER INFORMATION: Synthetic oligonucleotide

<400> SEQUENCE: 16
aacatatggc agaaatgaaa acggatgcgg c                                  31

<210> SEQ ID NO 17
<211> LENGTH: 33
<212> TYPE: DNA
<213> ORGANISM: Artificial Sequence
<220> FEATURE:
<223> OTHER INFORMATION: Synthetic oligonucleotide

<400> SEQUENCE: 17
ttcatatgga aacccatttg agagctcaga gcc                                33

<210> SEQ ID NO 18
<211> LENGTH: 33
<212> TYPE: DNA
<213> ORGANISM: Artificial Sequence
<220> FEATURE:
<223> OTHER INFORMATION: Synthetic oligonucleotide

<400> SEQUENCE: 18
aacatatgac cgaaaacctg acggttcagc cgg                                33

<210> SEQ ID NO 19
<211> LENGTH: 34
<212> TYPE: DNA
<213> ORGANISM: Artificial Sequence
<220> FEATURE:
<223> OTHER INFORMATION: Synthetic oligonucleotide

<400> SEQUENCE: 19
```

```
ttcatatggg tgaacaggcc gtcgattgct ttac                                      34

<210> SEQ ID NO 20
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 20
aacatatgac ggaacaacaa tggaactttg ctggc                                    35

<210> SEQ ID NO 21
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 21
ttcatatgtg cgaacatgcc cgtgacattg ccttc                                    35

<210> SEQ ID NO 22
<211> LENGTH: 1016
<212> TYPE: PRT
<213> ORGANISM: Artificial Sequence
<220> FEATURE:
<223> OTHER INFORMATION: Synthetic fusion polypeptide
<220> FEATURE:
<221> NAME/KEY: MISC_FEATURE
<223> OTHER INFORMATION: CFP10-Rv3615c-PhaC-ESAT6-Rv3020c fusion

<400> SEQUENCE: 22

Met Ala Glu Met Lys Thr Asp Ala Ala Thr Leu Ala Gln Glu Ala Gly
1               5                   10                  15

Asn Phe Glu Arg Ile Ser Gly Asp Leu Lys Thr Gln Ile Asp Gln Val
                20                  25                  30

Glu Ser Thr Ala Gly Ser Leu Gln Gly Gln Trp Arg Gly Ala Ala Gly
            35                  40                  45

Thr Ala Ala Gln Ala Ala Val Val Arg Phe Gln Glu Ala Ala Asn Lys
        50                  55                  60

Gln Lys Gln Glu Leu Asp Glu Ile Ser Thr Asn Ile Arg Gln Ala Gly
65                  70                  75                  80

Val Gln Tyr Ser Arg Ala Asp Glu Glu Gln Gln Gln Ala Leu Ser Ser
                85                  90                  95

Gln Met Gly Phe Gly Pro Gly Gly Gly Gly Pro Met Thr Glu Asn
                100                 105                 110

Leu Thr Val Gln Pro Glu Arg Leu Gly Val Leu Ala Ser His His Asp
            115                 120                 125

Asn Ala Ala Val Asp Ala Ser Ser Gly Val Glu Ala Ala Ala Gly Leu
        130                 135                 140

Gly Glu Ser Val Ala Ile Thr His Gly Pro Tyr Cys Ser Gln Phe Asn
145                 150                 155                 160

Asp Thr Leu Asn Val Tyr Leu Thr Ala His Asn Ala Leu Gly Ser Ser
                165                 170                 175

Leu His Thr Ala Gly Val Asp Leu Ala Lys Ser Leu Arg Ile Ala Ala
            180                 185                 190

Lys Ile Tyr Ser Glu Ala Asp Glu Ala Trp Arg Lys Ala Ile Asp Gly
        195                 200                 205
```

```
Leu Phe Thr Thr Ser Ala Thr Gly Lys Gly Ala Ala Ser Thr Gln
    210                 215                 220
Glu Gly Lys Ser Gln Pro Phe Lys Val Thr Pro Gly Pro Phe Asp Pro
225                 230                 235                 240
Ala Thr Trp Leu Glu Trp Ser Arg Gln Trp Gln Gly Thr Glu Gly Asn
                245                 250                 255
Gly His Ala Ala Ala Ser Gly Ile Pro Gly Leu Asp Ala Leu Ala Gly
            260                 265                 270
Val Lys Ile Ala Pro Ala Gln Leu Gly Asp Ile Gln Gln Arg Tyr Met
        275                 280                 285
Lys Asp Phe Ser Ala Leu Trp Gln Ala Met Ala Glu Gly Lys Ala Glu
290                 295                 300
Ala Thr Gly Pro Leu His Asp Arg Arg Phe Ala Gly Asp Ala Trp Arg
305                 310                 315                 320
Thr Asn Leu Pro Tyr Arg Phe Ala Ala Ala Phe Tyr Leu Leu Asn Ala
                325                 330                 335
Arg Ala Leu Thr Glu Leu Ala Asp Ala Val Glu Ala Asp Ala Lys Thr
            340                 345                 350
Arg Gln Arg Ile Arg Phe Ala Ile Ser Gln Trp Val Asp Ala Met Ser
        355                 360                 365
Pro Ala Asn Phe Leu Ala Thr Asn Pro Glu Ala Gln Arg Leu Leu Ile
370                 375                 380
Glu Ser Gly Gly Glu Ser Leu Arg Ala Gly Val Arg Asn Met Met Glu
385                 390                 395                 400
Asp Leu Thr Arg Gly Lys Ile Ser Gln Thr Asp Glu Ser Ala Phe Glu
                405                 410                 415
Val Gly Arg Asn Val Ala Val Thr Glu Gly Ala Val Val Phe Glu Asn
            420                 425                 430
Glu Tyr Phe Gln Leu Leu Gln Tyr Lys Pro Leu Thr Asp Lys Val His
        435                 440                 445
Ala Arg Pro Leu Leu Met Val Pro Pro Cys Ile Asn Lys Tyr Tyr Ile
450                 455                 460
Leu Asp Leu Gln Pro Glu Ser Ser Leu Val Arg His Val Val Glu Gln
465                 470                 475                 480
Gly His Thr Val Phe Leu Val Ser Trp Arg Asn Pro Asp Ala Ser Met
                485                 490                 495
Ala Gly Ser Thr Trp Asp Asp Tyr Ile Glu His Ala Ala Ile Arg Ala
            500                 505                 510
Ile Glu Val Ala Arg Asp Ile Ser Gly Gln Asp Lys Ile Asn Val Leu
        515                 520                 525
Gly Phe Cys Val Gly Gly Thr Ile Val Ser Thr Ala Leu Ala Val Leu
530                 535                 540
Ala Ala Arg Gly Glu His Pro Ala Ala Ser Val Thr Leu Leu Thr Thr
545                 550                 555                 560
Leu Leu Asp Phe Ala Asp Thr Gly Ile Leu Asp Val Phe Val Asp Glu
                565                 570                 575
Gly His Val Gln Leu Arg Glu Ala Thr Leu Gly Gly Ala Gly Ala
            580                 585                 590
Pro Cys Ala Leu Leu Arg Gly Leu Glu Leu Ala Asn Thr Phe Ser Phe
        595                 600                 605
Leu Arg Pro Asn Asp Leu Val Trp Asn Tyr Val Val Asp Asn Tyr Leu
610                 615                 620
Lys Gly Asn Thr Pro Val Pro Phe Asp Leu Leu Phe Trp Asn Gly Asp
```

```
                625                 630                 635                 640
Ala Thr Asn Leu Pro Gly Pro Trp Tyr Cys Trp Tyr Leu Arg His Thr
                    645                 650                 655

Tyr Leu Gln Asn Glu Leu Lys Val Pro Gly Lys Leu Thr Val Cys Gly
                    660                 665                 670

Val Pro Val Asp Leu Ala Ser Ile Asp Val Pro Thr Tyr Ile Tyr Gly
                    675                 680                 685

Ser Arg Glu Asp His Ile Val Pro Trp Thr Ala Ala Tyr Ala Ser Thr
                    690                 695                 700

Ala Leu Leu Ala Asn Lys Leu Arg Phe Val Leu Gly Ala Ser Gly His
705                 710                 715                 720

Ile Ala Gly Val Ile Asn Pro Pro Ala Lys Asn Lys Arg Ser His Trp
                    725                 730                 735

Thr Asn Asp Ala Leu Pro Glu Ser Pro Gln Gln Trp Leu Ala Gly Ala
                    740                 745                 750

Ile Glu His His Gly Ser Trp Trp Pro Asp Trp Thr Ala Trp Leu Ala
                    755                 760                 765

Gly Gln Ala Gly Ala Lys Arg Ala Ala Pro Ala Asn Tyr Gly Asn Ala
                    770                 775                 780

Arg Tyr Arg Ala Ile Glu Pro Ala Pro Gly Arg Tyr Val Lys Ala Lys
785                 790                 795                 800

Ala His Met Val Leu Ala Val Ala Ile Asp Lys Arg Gly Gly Gly Gly
                    805                 810                 815

Gly Leu Glu Met Thr Glu Gln Gln Trp Asn Phe Ala Gly Ile Glu Ala
                    820                 825                 830

Ala Ala Ser Ala Ile Gln Gly Asn Val Thr Ser Ile His Ser Leu Leu
                    835                 840                 845

Asp Glu Gly Lys Gln Ser Leu Thr Lys Leu Ala Ala Trp Gly Gly
                    850                 855                 860

Ser Gly Ser Glu Ala Tyr Gln Gly Val Gln Gln Lys Trp Asp Ala Thr
865                 870                 875                 880

Ala Thr Glu Leu Asn Asn Ala Leu Gln Asn Leu Ala Arg Thr Ile Ser
                    885                 890                 895

Glu Ala Gly Gln Ala Met Ala Ser Thr Glu Gly Asn Val Thr Gly Met
                    900                 905                 910

Phe Ala Gly Gly Gly Gly Gly Met Ser Leu Leu Asp Ala His Ile Pro
                    915                 920                 925

Gln Leu Ile Ala Ser His Thr Ala Phe Ala Ala Lys Ala Gly Leu Met
                    930                 935                 940

Arg His Thr Ile Gly Gln Ala Glu Gln Gln Ala Met Ser Ala Gln Ala
945                 950                 955                 960

Phe His Gln Gly Glu Ser Ala Ala Ala Phe Gln Gly Ala His Ala Arg
                    965                 970                 975

Phe Val Ala Ala Ala Lys Val Asn Thr Leu Leu Asp Ile Ala Gln
                    980                 985                 990

Ala Asn Leu Gly Glu Ala Ala Gly  Thr Tyr Val Ala Ala  Asp Ala Ala
                    995                 1000                1005

Ala Ala  Ser Ser Tyr Thr Gly  Phe
     1010                 1015
```

POLYMER PARTICLES AND USES THEREOF

CROSS REFERENCE TO RELATED APPLICATIONS

This application is a National Stage of International Application No. PCT/NZ2015/050008 filed Feb. 4, 2015, claiming priority based on New Zealand Patent Application No. 620682 filed Feb. 4, 2014, the contents of all of which are incorporated herein by reference in their entirety.

TECHNICAL FIELD

The present invention relates to recombinant proteins and related constructs and methods, and to polymer particles and uses thereof. In particular the present invention relates to functionalised polymer particles, processes of production and uses thereof in eliciting an immune response and in the diagnosis or treatment of *tuberculosis*.

BACKGROUND

The following includes information that is useful in understanding the present invention. It is not an admission that any of the information provided herein is prior art, or relevant, to the presently described or claimed inventions, or that any publication or document that is specifically or implicitly referenced is prior art.

Pathogens including intracellular and extracellular pathogens are known to cause a number of harmful diseases in humans, including, for example, *tuberculosis*, hepatitis, influenza, leprosy, listeriosis, typhoid fever, dysentery, plague, pneumonia, typhus, chlamydia, anthrax disease, and meningitis, amongst others. Both the ability to generate a robust cell-mediated immune response and a humoral response, elicited by traditional vaccination strategies, are encompassed herein.

*Tuberculosis* (TB), for example, is estimated to kill over 2 million people each year. Current methods for the treatment or prevention of *tuberculosis* are being challenged by the emergence of multi-drug resistant strains of *Mycobacterium tuberculosis* bacteria (Anderson, 2007; Mustafa, 2001). *Tuberculosis* is also a significant problem in livestock. The identification, treatment or prevention of TB is complicated by the inaccessability of the intracellular bacteria to the host's immune system.

It would be desirable to develop a safe, efficient and accurate method for identifying individuals who have been exposed to or are suffering from *tuberculosis* that overcomes many of the disadvantages of conventional diagnosis systems. Disadvantages include cost and difficulty in administering current diagnostic tests, together with low sensitivity/specificity.

There is thus a need for compositions capable of eliciting a robust immune response that is readily detectable, sensitive, and specific.

The properties of polyhydroxyalkyl carboxylates, in particular polyhydroxy alkanoates (PHAs) have been investigated for their application in bioplastics, in addition to their use as a matrix for the transport of drugs and other active agents in medical, pharmaceutical and food industry applications. Through bioengineering of the PHA molecule, the composition and expression of the PHA molecule can be manipulated to suit a particular function.

It is an object of the present invention to provide polymer particles for use in the diagnosis of *tuberculosis* and in the identification of *tuberculosis*-causing bacteria, including, for example, by immunological assays, to provide methods and compositions for eliciting an effective immune response in subjects in need thereof, or to at least provide the public with a useful choice.

BRIEF SUMMARY

The inventions described and claimed herein have many attributes and embodiments including, but not limited to, those set forth or described or referenced in this Brief Summary. It is not intended to be all-inclusive and the inventions described and claimed herein are not limited to or by the features or nonlimiting embodiments identified in this Brief Summary, which is included for purposes of illustration only and not restriction.

In a first aspect the present invention relates to a polymer particle comprising one or more fusion polypeptides, wherein one or more of the fusion polypeptides comprises a particle-forming protein and two or more of the group comprising
  i. an ESAT6 antigen or a binding domain capable of binding an ESAT6 antigen;
  ii. a CFP10 antigen or a binding domain capable of binding a CFP10 antigen,
  iii. an Rv3615c antigen or a binding domain capable of binding an Rv3615c antigen, and
  iv. an Rv3020c antigen or a binding domain capable of binding an Rv3020c antigen.

In one embodiment, one or more of the fusion polypeptides comprises a particle-forming protein and three or more of the group comprising
  i. an ESAT6 antigen or a binding domain capable of binding an ESAT6 antigen;
  ii. a CFP10 antigen or a binding domain capable of binding a CFP10 antigen;
  iii. an Rv3615c antigen or a binding domain capable of binding an Rv3615c antigen, and
  iv. an Rv3020c antigen or a binding domain capable of binding an Rv3020c antigen.

In one embodiment, one or more of the fusion polypeptides comprises a particle-forming protein, an ESAT6 antigen, a CFP10 antigen, and an Rv3615c antigen. For example, one or more of the fusion polypeptides comprises a particle-forming protein, an ESAT6 antigen, a CFP10 antigen, and an Rv3615c antigen, wherein said fusion polypeptide has at least about 95% sequence identity to the amino acid sequence depicted in SEQ. ID. NO. 10.

In one embodiment, one or more of the fusion polypeptides comprises a particle-forming protein and
  i. an ESAT6 antigen or a binding domain capable of binding an ESAT6 antigen; and
  ii. a CFP10 antigen or a binding domain capable of binding a CFP10 antigen; and
  iii. an Rv3615c antigen or a binding domain capable of binding an Rv3615c antigen, and
  iv. an Rv3020c antigen or a binding domain capable of binding an Rv3020c antigen.

In one embodiment, one or more of the fusion polypeptides comprises a particle-forming protein, an ESAT6 antigen, a CFP10 antigen, an Rv3615c antigen, and an Rv3020c antigen.

In various embodiments, one or more of the fusion polypeptides comprises an Rv2346c antigen. In one example, one or more of the fusion polypeptides comprises a particle-forming protein and three or more of the group comprising i. an ESAT6 antigen or a binding domain capable of binding an ESAT6 antigen;
ii. a CFP10 antigen or a binding domain capable of binding a CFP10 antigen;
iii. an Rv3615c antigen or a binding domain capable of binding an Rv3615c antigen;
iv. an Rv3020c antigen or a binding domain capable of binding an Rv3020c antigen; and
v. an Rv2346c antigen or a binding domain capable of binding an Rv2346c antigen.

In one embodiment, one or more of the fusion polypeptides comprises a particle-forming protein, an ESAT6 antigen, a CFP10 antigen, an Rv3615c antigen, an Rv3020c antigen, and an Rv2346c antigen.

In one embodiment the polymer particle comprises two or more different fusion polypeptides. In one embodiment, the polymer particle comprises at least one fusion polypeptide comprising a particle-forming protein and two or more of the group comprising
  i. an ESAT6 antigen or a binding domain capable of binding an ESAT6 antigen;
  ii. a CFP10 antigen or a binding domain capable of binding a CFP10 antigen;
  iii. an Rv3615c antigen or a binding domain capable of binding an Rv3615c antigen;
  iv. an Rv3020c antigen or a binding domain capable of binding an Rv3020c antigen; and
  v. an Rv2346c antigen or a binding domain capable of binding an Rv2346c antigen;
and at least one fusion polypeptide comprising a particle-forming protein and one or more of the group comprising
  vi. an ESAT6 antigen or a binding domain capable of binding an ESAT6 antigen;
  vii. a CFP10 antigen or a binding domain capable of binding a CFP10 antigen;
  viii. an Rv3615c antigen or a binding domain capable of binding an Rv3615c antigen;
  ix. an Rv3020c antigen or a binding domain capable of binding an Rv3020c antigen; and
  x. an Rv2346c antigen or a binding domain capable of binding an Rv2346c antigen.

In one embodiment, the one or more antigens of the group (vi) to (x) is different to the two or more antigens of group (i) to (v). In one embodiment, the fusion polypeptide comprising one or more antigens of the group (vi) to (x) is different to the fusion polypeptide comprising two or more antigens of group (i) to (v).

In one embodiment, the polymer particle comprises at least one fusion polypeptide comprising a particle-forming protein and three or more of the group comprising
  i. an ESAT6 antigen or a binding domain capable of binding an ESAT6 antigen;
  ii. a CFP10 antigen or a binding domain capable of binding a CFP10 antigen;
  iii. an Rv3615c antigen or a binding domain capable of binding an Rv3615c antigen; and
  iv. an Rv3020c antigen or a binding domain capable of binding an Rv3020c antigen;
and at least one fusion polypeptide comprising a particle-forming protein and an Rv2346c antigen.

In one embodiment the polymer particle comprises two or more different fusion polypeptides on the polymer particle surface.

In one embodiment the polymer particle further comprises at least one substance bound to or incorporated into the polymer particle, or a combination thereof.

In one embodiment the substance is an antigen, or an adjuvant, or an immunostimulatory molecule.

In one embodiment the substance is bound by crosslinking.

In one embodiment, the ESAT6 antigen comprises 10 or more contiguous amino acids from the amino acid sequence of SEQ. ID. No. 1. For example, the ESAT6 antigen comprises 15 or more, 20 or more, 25 or more, or 30 or more contiguous amino acids from the amino acid sequence of SEQ. ID. No. 1. In one specifically contemplated embodiment, the ESAT6 antigen comprises the amino acid sequence of SEQ. ID. No. 1.

In one embodiment, the CFP10 antigen comprises 10 or more contiguous amino acids from the amino acid sequence of SEQ. ID. No. 2. For example, the CFP10 antigen comprises 15 or more, 20 or more, 25 or more, or 30 or more contiguous amino acids from the amino acid sequence of SEQ. ID. No. 2. In one specifically contemplated embodiment, the CFP10 antigen comprises the amino acid sequence of SEQ. ID. No. 2.

In one embodiment, the Rv3615c antigen comprises 10 or more contiguous amino acids from the amino acid sequence of SEQ. ID. No. 3. For example, the Rv3615c antigen comprises 15 or more, 20 or more, 25 or more, or 30 or more contiguous amino acids from the amino acid sequence of SEQ. ID. No. 3. In one specifically contemplated embodiment, the Rv3615c antigen comprises the amino acid sequence of SEQ. ID. No. 3.

In one embodiment, the Rv3020c antigen comprises 10 or more contiguous amino acids from the amino acid sequence of SEQ. ID. No. 4. For example, the Rv3020c antigen comprises 15 or more, 20 or more, 25 or more, or 30 or more contiguous amino acids from the amino acid sequence of SEQ. ID. No. 4. In one specifically contemplated embodiment, the Rv3020c antigen comprises the amino acid sequence of SEQ. ID. No. 4.

In one embodiment, the Rv2346c antigen comprises 10 or more contiguous amino acids from the amino acid sequence of SEQ. ID. No. 5. For example, the Rv2346c antigen comprises 15 or more, 20 or more, 25 or more, or 30 or more contiguous amino acids from the amino acid sequence of SEQ. ID. No. 5. In one specifically contemplated embodiment, the Rv2346c antigen comprises the amino acid sequence of SEQ. ID. No. 5.

Another aspect of the present invention relates to a polymer particle produced according to a method of the invention.

Another aspect of the present invention relates to a composition comprising one or more polymer particles of the invention and a pharmaceutically acceptable carrier.

In one embodiment, the composition comprises one or more polymer particles comprising one or more fusion polypeptides, wherein one or more of the fusion polypeptides comprises a particle-forming protein and two or more of the group comprising
  i. an ESAT6 antigen or a binding domain capable of binding an ESAT6 antigen;
  ii. a CFP10 antigen or a binding domain capable of binding a CFP10 antigen,
  iii. an Rv3615c antigen or a binding domain capable of binding an Rv3615c antigen, and
  iv. an Rv3020c antigen or a binding domain capable of binding an Rv3020c antigen.

In one embodiment, the composition comprises one or more polymer particles comprising one or more fusion polypeptides, wherein one or more fusion polypeptides comprises a particle-forming protein, an ESAT6 antigen, a CFP10 antigen, and an Rv3615c antigen. In another embodiment, the composition comprises one or more polymer particles comprising one or more fusion polypeptides, wherein one or more fusion polypeptides comprises a particle-forming protein, an ESAT6 antigen, a CFP10 antigen, an Rv3615c antigen, and an Rv3020c antigen.

In various embodiments, one or more of the fusion polypeptides comprises an Rv2346c antigen. In one example, one or more of the fusion polypeptides comprises a particle-forming protein and three or more of the group comprising
  i. an ESAT6 antigen or a binding domain capable of binding an ESAT6 antigen;
  ii. a CFP10 antigen or a binding domain capable of binding a CFP10 antigen;
  iii. an Rv3615c antigen or a binding domain capable of binding an Rv3615c antigen;
  iv. an Rv3020c antigen or a binding domain capable of binding an Rv3020c antigen; and
  v. an Rv2346c antigen or a binding domain capable of binding an Rv2346c antigen.

In one embodiment, one or more of the fusion polypeptides comprises a particle-forming protein, an ESAT6 antigen, a CFP10 antigen, an Rv3615c antigen, an Rv3020c antigen, and an Rv2346c antigen.

In one embodiment, the composition comprises two or more fusion polypeptides, wherein one or more fusion polypeptides comprises a particle-forming protein and two or more of the group comprising
  i. an ESAT6 antigen or a binding domain capable of binding an ESAT6 antigen;
  ii. a CFP10 antigen or a binding domain capable of binding a CFP10 antigen;
  iii. an Rv3615c antigen or a binding domain capable of binding an Rv3615c antigen;
  iv. an Rv3020c antigen or a binding domain capable of binding an Rv3020c antigen; and
  v. an Rv2346c antigen or a binding domain capable of binding an Rv2346c antigen;
and at least one fusion polypeptide comprises a particle-forming protein and one or more of the group comprising
  vi. an ESAT6 antigen or a binding domain capable of binding an ESAT6 antigen;
  vii. a CFP10 antigen or a binding domain capable of binding a CFP10 antigen;
  viii. an Rv3615c antigen or a binding domain capable of binding an Rv3615c antigen;
  ix. an Rv3020c antigen or a binding domain capable of binding an Rv3020c antigen; and
  x. an Rv2346c antigen or a binding domain capable of binding an Rv2346c antigen.

In one embodiment, the fusion polypeptide comprising one or more antigens of the group (vi) to (x) is different to the fusion polypeptide comprising two or more antigens of group (i) to (v).

In one embodiment, the composition comprises two or more populations of polymer particles, wherein one population of polymer particles comprises one or more fusion polypeptides comprising a particle-forming protein and two or more of the group comprising
  i. an ESAT6 antigen or a binding domain capable of binding an ESAT6 antigen;
  ii. a CFP10 antigen or a binding domain capable of binding a CFP10 antigen;
  iii. an Rv3615c antigen or a binding domain capable of binding an Rv3615c antigen;
  iv. an Rv3020c antigen or a binding domain capable of binding an Rv3020c antigen; and
  v. an Rv2346c antigen or a binding domain capable of binding an Rv2346c antigen;
and one population of polymer particles comprises one or more fusion polypeptides comprising a particle-forming protein and one or more of the group comprising
  vi. an ESAT6 antigen or a binding domain capable of binding an ESAT6 antigen;
  vii. a CFP10 antigen or a binding domain capable of binding a CFP10 antigen;
  viii. an Rv3615c antigen or a binding domain capable of binding an Rv3615c antigen;
  ix. an Rv3020c antigen or a binding domain capable of binding an Rv3020c antigen; and
  x. an Rv2346c antigen or a binding domain capable of binding an Rv2346c antigen;
wherein the fusion polypeptides are different from one another, for example, wherein one or more of the fusion polypeptides present on one population of polymer particles is different to one or more of the fusion polypeptides present on another population of polymer particles.

In one example, the arrangement of the antigens differs between the fusion polypeptides. In one embodiment the composition of the antigens differs between the fusion polypeptides.

Another aspect of the present invention relates to a composition of polymer particles, wherein the polymer particles are produced according to a method of the invention.

In various embodiments, the composition is a vaccine composition. In various embodiments the vaccine composition additionally comprises one or more adjuvants or immunostimulatory molecules.

Another aspect of the present invention relates to a diagnostic reagent comprising one or more polymer particles of the invention, or comprising a composition of polymer particles of the invention.

In one embodiment, the diagnostic reagent is for topical administration.

In one embodiment, the diagnostic reagent is formulated to provide less than 10 microgram total antigen per dose. For example, the diagnostic reagent comprises less than 9 μg total antigen per dose, less than 8 μg total antigen per dose, less than 7 μg total antigen per dose, less than 6 μg total antigen per dose, less than 5 μg total antigen per dose, less than 4 μg total antigen per dose, less than 3 μg total antigen per dose, less than 2 μg total antigen per dose, or less than 1 μg total antigen per dose.

In one embodiment the diagnostic reagent is formulated to provide less than 5 μg of one or more of the antigens present per dose. For example, the diagnostic reagent comprises less than 5 μg of one or more of the antigens present per dose, less than 4 μg of one or more of the antigens present per dose, less than 3 μg of one or more of the antigens present per dose, less than 2 μg of one or more of the antigens present per dose, or less than 1 μg of one or more of the antigens present per dose.

In one embodiment the diagnostic reagent is formulated to provide less than 5 μg of each antigen present per dose. For example, the diagnostic reagent comprises less than 5 μg of each antigen present per dose, less than 4 μg of each antigen present per dose, less than 3 μg of each antigen present per dose, less than 2 μg of each antigen present per dose, less than 1 μg of each antigen present per dose.

In one embodiment the diagnostic reagent is formulated to provide less than 0.9 μg of one or more of the antigens present per dose. For example, the diagnostic reagent comprises less than 0.9 µg of one or more of the antigens present per dose, less than 0.8 µg of one or more of the antigens present per dose, less than 0.7 µg of one or more of the antigens present per dose, less than 0.6 µg of one or more of the antigens present per dose, less than 0.5 µg of one or more of the antigens present per dose, less than 0.4 µg of one or more of the antigens present per dose, less than 0.3 µg of one or more of the antigens present per dose, less than 0.2 µg of one or more of the antigens present per dose, or less than 0.1 µg of one or more of the antigens present per dose.

In particularly contemplated embodiments, the diagnostic reagent comprises less than 0.9 µg of each antigen present per dose, less than 0.8 µg of each antigen present per dose, less than 0.7 µg of each antigen present per dose, less than 0.6 µg of each antigen present per dose, less than 0.5 µg of each antigen present per dose, less than 0.4 µg of each antigen present per dose, less than 0.3 µg of each antigen present per dose, less than 0.2 µg of each antigen present per dose, or less than 0.1 µg of each antigen present per dose.

For example, in one exemplary embodiment the diagnostic reagent comprises 0.3 µg ESAT6 antigen, 0.3 µg CFP10 antigen, and 0.3 µg Rv3615c antigen, per dose.

In various embodiments, the diagnostic reagent is for contacting a sample obtained from a subject.

In other particularly contemplated embodiments, the diagnostic reagent is formulated to provide less than 50 ng of each antigen present per dose, less than 40 ng of each antigen present per dose, less than 30 ng of each antigen present per dose, less than 20 ng of each antigen present per dose, less than 10 ng of each antigen present per dose, or less than 5 ng of each antigen present per dose. In other examples, the diagnostic reagent is formulated to provide less than 50 ng total antigen per dose, less than 40 ng total antigen per dose, less than 30 ng total antigen per dose, less than 20 ng total antigen per dose, less than 10 ng total antigen per dose, less than 7.5 ng total antigen per dose, less than 6 ng total antigen per dose, or less than 5 ng total antigen per dose.

Another aspect of the present invention relates to a diagnostic kit comprising a composition of polymer particles of the invention, and optionally instructions for use.

In one embodiment, the composition comprises an homogenous population of polymer particles.

In one embodiment, the composition comprises a mixed population of polymer particles.

In one embodiment, the composition additionally comprises one or more of the following:
one or more *M. tuberculosis* or *M. bovis* antigens,
one or more binding domains capable of binding one or more *M. tuberculosis* or *M. bovis* antigens,
one or more adjuvants, or
one or more immunomodulatory agents or molecules.

Another aspect of the present invention relates to a method of eliciting an immune response in a subject, wherein the method comprises administering to a subject in need thereof at least one polymer particle of the invention in an amount sufficient to elicit an immune response in the subject.

In one embodiment the invention relates to a method of eliciting an immune response in a subject infected with *tuberculosis*, wherein the method comprises administering to the subject one or more polymer particles comprising one or more fusion polypeptides, wherein one or more of the fusion polypeptides comprises a particle-forming protein and two or more of the group comprising i. an ESAT6 antigen or a binding domain capable of binding an ESAT6 antigen;
ii. a CFP10 antigen or a binding domain capable of binding a CFP10 antigen,
iii. an Rv3615c antigen or a binding domain capable of binding an Rv3615c antigen, and
iv. an Rv3020c antigen or a binding domain capable of binding an Rv3020c antigen.

In one embodiment, the one or more polymer particles is present in a composition additionally comprising at least one polymer particle comprising one or more fusion polypeptides comprising a binding domain capable of binding an *M. tuberculosis* or *M. bovis* antigen, for example, an endogenous *M. tuberculosis* or *M. bovis* antigen.

In various embodiments the subject is infected with *tuberculosis*.

In another embodiment the subject has been immunised against an intracellular pathogen, for example. For example, the subject has been vaccinated with *Bacillus* Calmette-Guerin (BCG). In one embodiment, the immune response elicited in a subject exposed to *M. tuberculosis* or *M. bovis* or suffering from *tuberculosis* differs to that elicited in a subject immunised against *tuberculosis*, for example with BCG.

In one embodiment the invention relates to a method of diagnosing *tuberculosis* in a subject, the method comprising administering to the subject an effective amount of at least one polymer particle of the invention, and detecting an immune response in the subject, wherein the presence of an immune response is indicative of *tuberculosis*.

In one embodiment, the invention relates to a method of detecting *M. tuberculosis* or *M. bovis* in a subject, the method comprising administering to a subject an effective amount of at least one polymer particle of the invention, and detecting an immune response in the subject, wherein the presence of an immune response is indicative of *tuberculosis*.

In one embodiment, the administration is topical, for example, by skin prick.

In various embodiments, the effective amount of at least one polymer particle of the invention is present in a diagnostic reagent as herein described. Accordingly, in one embodiment the method comprises administering to a subject a diagnostic reagent of the present invention.

For example, in one embodiment the method comprises administering to a subject a diagnostic reagent of the present invention, wherein the diagnostic reagent comprises less than 5 µg of each antigen present per dose, and detecting an immune response in the subject, wherein the presence of an immune response is indicative of *tuberculosis*.

In one embodiment, the administration is of a diagnostic reagent of the present invention, wherein the diagnostic reagent comprises less than 5 µg total antigen per dose.

In one embodiment, the administration is of a diagnostic reagent of the present invention, wherein the diagnostic reagent comprises less than 1 µg of each antigen present per dose.

In one embodiment, the administration is of a diagnostic reagent of the present invention, wherein the diagnostic reagent comprises less than 0.5 µg of each antigen present per dose.

In one embodiment the immune response indicative of *tuberculosis* is a delayed-type hypersensitivity response.

In one embodiment, the method is capable of discriminating between a subject exposed to *M. tuberculosis* or *M. bovis* or suffering from *tuberculosis*, and a subject immunised against *tuberculosis*, for example with BCG.

In various embodiments, a positive skin test is as follows: (i) SICCT response considered positive if the change in (Δ) skin thickness for PPD-B−PPD-A is >4 mm, or (ii) >2 mm (strict United Kingdom test); (iii) SIT response considered positive if Δ skin thickness for PPD-B is ≥4 mm; and (iv) responses for polymer particles of the invention are considered positive if Δ skin thickness is ≥1 mm.

For example, a positive skin test with the diagnostic reagent of the present invention or in a method of the invention, including, for example, a method comprising the administration of a diagnostic reagent comprising less than 1 µg of each antigen present per dose is a Δ skin thickness is ≥1 mm.

In one embodiment, the invention relates to a method of detecting *M. tuberculosis* or *M. bovis* in a subject, the method comprising
providing a sample from a subject,
contacting the sample with at least one polymer particle of the invention, and
detecting a response indicative of the presence of one or more *M. tuberculosis* antigens in the sample,
wherein a response indicative of the presence of one or more *M. tuberculosis* or *M. bovis* antigens is indicative of *M. tuberculosis* or *M. bovis* in the subject.

In one embodiment, the response indicative of the presence of one or more *M. tuberculosis* or *M. bovis* antigens is a detecting the presence of an antibody to *M. tuberculosis* or *M. bovis* in said sample.

In one embodiment, the response indicative of the presence of one or more *M. tuberculosis* or *M. bovis* antigens is a detecting the presence of an immune cell responsive to *M. tuberculosis* or *M. bovis* in said sample.

In one embodiment the detection is by immunoassay.

In one embodiment the detection is by ELISA, radioimmunoassay, or Western Blot.

In one embodiment, the detection is by cytokine assay. In one embodiment, the detection is of interferon-gamma.

In one embodiment the presence of an immune cell responsive to *Mycobacterium tuberculosis* or *M. bovis* is detected by a cell proliferation assay, a cell sorting assay including FACS, or an in situ hybridisation assay.

In one embodiment the method relates to a method of immunising a subject against *tuberculosis*, wherein the method comprises administering to a subject in need thereof an effective amount of at least one polymer particle of the invention.

The use of a polymer particle of the invention in the preparation of a medicament for immunising a subject against *tuberculosis*, or of a composition for eliciting an immune response in a subject including a subject infected with or immunised against *tuberculosis*, is also contemplated.

In anther aspect the invention relates to a method for producing polymer particles, the method comprising providing a host cell comprising at least one expression construct, the at least one expression construct comprising:
at least one nucleic acid sequence encoding a particle-forming protein; and
two or more nucleic acid sequences selected from the group consisting of a nucleic acid sequence encoding an ESAT6 antigen, a nucleic acid sequence encoding a binding domain capable of binding an ESAT6 antigen, a nucleic acid sequence encoding a CFP10 antigen, a nucleic acid sequence encoding a binding domain capable of binding a CFP10 antigen, a nucleic acid sequence encoding an Rv3615c antigen, and a nucleic acid sequence encoding a binding domain capable of binding an Rv3615c antigen, a nucleic acid sequence encoding an Rv3020c antigen, and a nucleic acid sequence encoding a binding domain capable of binding an Rv3020c antigen;
maintaining the host cell under conditions suitable for expression of the expression construct; and
separating polymer particles from host cells.

In one embodiment the at least one expression construct comprises:
at least one nucleic acid sequence encoding a particle-forming protein; and
at least one nucleic acid sequence encoding an ESAT6 antigen or at least one nucleic acid sequence encoding a binding domain capable of binding an ESAT6 antigen; and at least one nucleic acid sequence encoding a CFP10 antigen or at least one nucleic acid sequence encoding a binding domain capable of binding a CFP10 antigen; and at least one nucleic acid sequence encoding an Rv3615c antigen or at least one nucleic acid sequence encoding a binding domain capable of binding an Rv3615c antigen.

In one embodiment the at least one expression construct comprises
at least one nucleic acid sequence encoding a particle-forming protein; and
at least one nucleic acid sequence encoding an ESAT6 antigen; and
at least one nucleic acid sequence encoding a CFP10 antigen; and
at least one nucleic acid sequence encoding an Rv3615c antigen.

In one embodiment the at least one expression construct comprises
at least one nucleic acid sequence encoding a particle-forming protein; and
at least one nucleic acid sequence encoding an ESAT6 antigen; and
at least one nucleic acid sequence encoding a CFP10 antigen; and
at least one nucleic acid sequence encoding an Rv3615c antigen; and
at least one nucleic acid sequence encoding an Rv3020c antigen.

In one embodiment the particle-forming protein is a polymer synthase.

In one embodiment the expression construct is in a high copy number vector.

In one embodiment the at least one nucleic acid sequence encoding a particle-forming protein, is operably linked to a strong promoter.

In one embodiment the strong promoter is a viral promoter or a phage promoter.

In one embodiment the promoter is a phage promoter, for example a T7 phage promoter.

In one embodiment the host cell is maintained in the presence of a substrate of a polymer synthase, preferably a substrate of a polymer synthase when present or a substrate mixture, including monomeric substrate, or a precursor substrate able to be metabolised by the host cell to form a substrate of the particle-forming protein.

In one embodiment the host cell comprises at least two different expression constructs.

In some embodiments in which the host cell comprises at least two different expression constructs, at least one of the expression constructs is selected from the group comprising:
an expression construct comprising a nucleic acid sequence encoding a particle-forming protein, and at least one antigen selected from the group consisting of ESAT6, CFP10, and Rv3615c, or an expression construct comprising a nucleic acid sequence encoding a particle-forming protein, and a binding domain capable of binding at least one antigen selected from the group consisting of ESAT6, CFP10, Rv3615c, and Rv3020c, or an expression construct comprising a nucleic acid sequence encoding an adjuvant.

In other embodiments in which the host cell comprises at least two different expression constructs, one of the expression constructs is selected from the group comprising:

an expression construct comprising a nucleic acid sequence encoding a particle-forming protein, or an expression construct comprising a nucleic acid sequence encoding a particle-size determining protein, or an expression construct comprising a nucleic acid sequence encoding a polymer regulator.

In one embodiment the host cell comprises a mixed population of expression constructs wherein each expression construct comprises a nucleic acid sequence encoding a fusion polypeptide, the fusion polypeptide comprising:

at least one particle-forming protein, and either at least one antigen selected from the group consisting of ESAT6, CFP10, Rv3615c, and Rv3020c, or at least one binding domain capable of binding at least one antigen selected from the group consisting of ESAT6, CFP10, Rv3615c, and Rv3020c.

In various embodiments, the fusion polypeptide comprises two or more antigens selected from the group consisting of ESAT6, CFP10, and Rv3615c, for example the fusion polypeptide comprises each of the antigens of the group comprising ESAT6, CFP10, and Rv3615c.

In various embodiments, the fusion polypeptide comprises two or more antigens selected from the group consisting of ESAT6, CFP10, Rv3615c, and Rv3020c, for example the fusion polypeptide comprises each of the antigens of the group comprising ESAT6, CFP10, Rv3615c, and Rv3020c.

Another aspect of the present invention relates to an isolated nucleic acid or an expression construct, the isolated nucleic acid or expression construct comprising:

at least one nucleic acid sequence encoding a particle-forming protein; and two or more nucleic acid sequences selected from the group consisting of a nucleic acid sequence encoding an ESAT6 antigen, a nucleic acid sequence encoding a binding domain capable of binding an ESAT6 antigen, a nucleic acid sequence encoding a CFP10 antigen, a nucleic acid sequence encoding a binding domain capable of binding a CFP10 antigen, a nucleic acid sequence encoding an Rv3615c antigen, a nucleic acid sequence encoding a binding domain capable of binding an Rv3615c antigen, a nucleic acid sequence encoding an Rv3020c antigen, and a nucleic acid sequence encoding a binding domain capable of binding an Rv3020c antigen.

In one embodiment the at least one nucleic acid sequence encoding the particle-forming protein and the two or more nucleic acid sequences encoding the antigen(s) or binding domain(s) are present as a single open reading frame.

In one embodiment the at least one nucleic acid sequence encoding the particle-forming protein is operably linked to a strong promoter.

In various embodiments, the at least one nucleic acid comprises 20 or more contiguous nucleic acids selected from one of SEQ. ID. NO.s 11-21 herein. Isolated nucleic acid sequences comprising 20 or more contiguous nucleic acids selected from one of SEQ. ID. NO.s 11-15, including sequences encoding two or more antigens and a particle-forming protein, are particularly contemplated.

In one embodiment, the at least one nucleic acid comprises the nucleic acid sequence of one of SEQ. ID. NO.s 11-21 herein.

Probes or primers comprising 20 or more contiguous nucleic acids of one of SEQ. ID. NO.s 11-15, particularly probes or primers comprising nucleic acid sequences encoding two or more antigens and a particle-forming protein, are particularly contemplated.

In one embodiment the expression construct comprises at least one nucleic acid sequence encoding an additional polypeptide.

In one embodiment, the expression construct comprises:

at least one nucleic acid sequence encoding a fusion polypeptide that comprises a particle-forming protein, and at least one a binding domain capable of binding an antigen selected from the group consisting of ESAT6, CFP10, Rv3615c, and Rv3020c; and at least one nucleic acid sequence encoding an additional polypeptide that binds the binding domain capable of binding an antigen selected from the group consisting of ESAT6, CFP10, Rv3615c, and Rv3020c.

In one embodiment the additional polypeptide is a fusion polypeptide comprising a particle-forming protein, and at least one *M. tuberculosis* or *M. bovis* antigen.

In one embodiment the construct additionally comprises a nucleic acid encoding
  i. at least one thiolase, or
  ii. at least one reductase, or
  iii. both (i) and (ii).

In one embodiment the construct comprises a nucleic acid encoding
  i. at least one thiolase,
  ii. at least one reductase,
  iii. at least one polymer synthase;
  iv. at least one *M. tuberculosis* or *M. bovis* antigen, or
  v. at least one binding domain capable of binding at least one *M. tuberculosis* or *M. bovis* antigen,
  vi. a fusion protein comprising one or more of i) to v) above,
  vii. any combination of i) to vi) above.

Another aspect of the present invention relates to a vector comprising an expression construct of the invention.

In one embodiment the vector is a high copy number vector.

In one embodiment the vector is a low copy number vector.

Another aspect of the present invention relates to a host cell comprising an expression construct or a vector as defined above.

In one embodiment the host cell comprises an expression construct comprising a nucleic acid sequence encoding a particle-forming protein, at least one nucleic acid sequence encoding an ESAT6 antigen or at least one nucleic acid sequence encoding a binding domain capable of binding an ESAT6 antigen, and at least one nucleic acid sequence encoding a CFP10 antigen or at least one nucleic acid sequence encoding a binding domain capable of binding a CFP10 antigen, and at least one nucleic acid sequence encoding an Rv3615c antigen or at least one nucleic acid sequence encoding a binding domain capable of binding an Rv3615c antigen.

In another embodiment the host cell comprises an expression construct comprising a nucleic acid sequence encoding a particle-forming protein, at least one nucleic acid sequence encoding an ESAT6 antigen or at least one nucleic acid sequence encoding a binding domain capable of binding an ESAT6 antigen, and at least one nucleic acid sequence encoding a CFP10 antigen or at least one nucleic acid sequence encoding a binding domain capable of binding a CFP10 antigen, and at least one nucleic acid sequence encoding an Rv3615c antigen or at least one nucleic acid sequence encoding a binding domain capable of binding an Rv3615c antigen, and at least one nucleic acid sequence encoding an Rv3020c antigen or at least one nucleic acid sequence encoding a binding domain capable of binding an Rv3020c antigen.

Any of the embodiments described herein including those following may relate to any of the aspects described herein.

In various embodiments the particle-forming protein is a polymer synthase.

In various embodiments the polymer particle comprises a polymer selected from poly-beta-amino acids, polylactates, polythioesters and polyesters. Most preferably the polymer comprises polyhydroxyalkanoate (PHA), preferably poly(3-hydroxybutyrate) (PHB).

In various embodiments the polymer particle comprises a polymer particle encapsulated by a phospholipid monolayer.

In various embodiments the polymer particle comprises two or more different fusion polypeptides.

In various embodiments the polymer particle comprises two or more different fusion polypeptides on the polymer particle surface.

In various embodiments the polymer particle comprises three or more different fusion polypeptides, such as three or more different fusion polypeptides on the polymer particle surface.

In various embodiments the polymer particle further comprises at least one substance bound to or incorporated into the polymer particle, or a combination thereof.

In various embodiments the substance is an antigen, adjuvant or immunostimulatory molecule.

In various embodiments the substance is bound to the polymer particle by cross-linking.

In various embodiments the polymer synthase is bound to the polymer particle or to the phospholipid monolayer or is bound to both.

In various embodiments the polymer synthase is covalently or non-covalently bound to the polymer particle it forms.

In various embodiments the polymer synthase is a PHA synthase from the class 1 genera *Acinetobacter, Vibrio, Aeromonas, Chromobacterium, Pseudomonas, Zoogloea, Alcaligenes, Delftia, Burkholderia, Ralstonia, Rhodococcus, Gordonia, Rhodobacter, Paracoccus, Rickettsia, Caulobacter, Methylobacterium, Azorhizobium, Agrobacterium, Rhizobium, Sinorhizobium, Rickettsia, Crenarchaeota, Synechocystis, Ectothiorhodospira, Thiocapsa, Thyocystis* and *Allochromatium*, the class 2 genera *Burkholderia* and *Pseudomonas*, or the class 4 genera *Bacillus*, more preferably from the group comprising class 1 *Acinetobacter* sp. RA3849, *Vibrio cholerae, Vibrio parahaemolyticus, Aeromonas punctata* FA440, *Aeromonas hydrophila, Chromobacterium violaceum, Pseudomonas* sp. 61-3, *Zoogloea ramigera, Alcaligenes latus, Alcaligenes* sp. SH-69, *Delftia acidovorans, Burkholderia* sp. DSMZ9242, *Ralstonia eutrophia* H16, *Burkholderia cepacia, Rhodococcus rubber* PP2, *Gordonia rubripertinctus, Rickettsia prowazekii, Synechocystis* sp. PCC6803, *Ectothiorhodospira shaposhnikovii* N1, *Thiocapsa pfennigii* 9111, *Allochromatium vinosum* D, *Thyocystis violacea* 2311, *Rhodobacter sphaeroides, Paracoccus denitrificans, Rhodobacter capsulatus, Caulobacter crescentus, Methylobacterium extorquens, Azorhizobium caulinodans, Agrobacterium tumefaciens, Sinorhizobium meliloti* 41, *Rhodospirillum rubrum* HA, and *Rhodospirillum rubrum* ATCC25903, class 2 *Burkholderia caryophylli, Pseudomonas chloraphis, Pseudomonas* sp. 61-3, *Pseudomonas putida* U, *Pseudomonas oleovorans, Pseudomonas aeruginosa, Pseudomonas resinovorans, Pseudomonas stutzeri, Pseudomonas mendocina, Pseudomonas pseudolcaligenes, Pseudomonas putida* BM01, *Pseudomonas nitroreducins, Pseudomonas chloraphis*, and class 4 *Bacillus megaterium* and *Bacillus* sp. INT005.

In other embodiments the polymer synthase is a PHA polymer synthase from Gram-negative and Gram-positive eubacteria, or from archaea.

In various examples, the polymer synthase may comprise a PHA polymer synthase from *C. necator, P. aeruginosa, A. vinosum, B. megaterium, H. marismortui, P. aureofaciens*, or *P. putida*, which have Accession No.s AY836680, AE004091, AB205104, AF109909, YP137339, AB049413 and AF150670, respectively.

Other polymer synthases amenable to use in the present invention include polymer synthases, each identified by it accession number, from the following organisms: *R. eutropha* (A34341), *T. pfennigii* (X93599), *A. punctata* (O32472), *Pseudomonas* sp. 61-3 (AB014757 and AB014758), *R. sphaeroides* (AAA72004), *C. violaceum* (AAC69615), *A. borkumensis* SK2 (CAL17662), *A. borkumensis* SK2 (CAL16866), *R. sphaeroides* KD131 (ACM01571 and YP002526072), *R. opacus* B4 (BAH51880 and YP002780825), *B. multivorans* ATCC 17616 (YP001946215 and BAG43679), *A. borkumensis* SK2 (YP693934 and YP693138), *R. rubrum* (AAD53179), gamma proteobacterium HTCC5015 (ZP05061661 and EDY86606), *Azoarcus* sp. BH72 (YP932525), *C. violaceum* ATCC 12472 (NP902459), *Limnobacter* sp. MED105 (ZP01915838 and EDM82867), *M. algicola* DG893 (ZP01895922 and EDM46004), *R. sphaeroides* (CAA65833), *C. violaceum* ATCC 12472 (AAQ60457), *A. latus* (AAD10274, AAD01209 and AAC83658), *S. maltophilia* K279a (CAQ46418 and YP001972712), *R. solanacearum* IPO1609 (CAQ59975 and YP002258080), *B. multivorans* ATCC 17616 (YP001941448 and BAG47458), *Pseudomonas* sp. g113 (ACJ02400), *Pseudomonas* sp. g106 (ACJ02399), *Pseudomonas* sp. g101 (ACJ02398), R. sp. g132 (ACJ02397), *R. leguminosarum* bv. *viciae* 3841 (CAK10329 and YP770390), *Azoarcus* sp. BH72 (CAL93638), *Pseudomonas* sp. LDC-5 (AAV36510), *L. nitroferrum* 2002 (ZP03698179), *Thauera* sp. MZ1T (YP002890098 and ACR01721), *M. radiotolerans* JCM 2831 (YP001755078 and ACB24395), *Methylobacterium* sp. 4-46 (YP001767769 and ACA15335), *L. nitroferrum* 2002 (EEG08921), *P. denitrificans* (BAA77257), *M. gryphiswaldense* (ABG23018), *Pseudomonas* sp. USM4-55 (ABX64435 and ABX64434), *A. hydrophila* (AAT77261 and AAT77258), *Bacillus* sp. INT005 (BAC45232 and BAC45230), *P. putida* (AAM63409 and AAM63407), *G. rubripertinctus* (AAB94058), *B. megaterium* (AAD05260), *D. acidovorans* (BAA33155), *P. seriniphilus* (ACM68662), *Pseudomonas* sp. 14-3 (CAK18904), *Pseudomonas* sp. LDC-5 (AAX18690), *Pseudomonas* sp. PC17 (ABV25706), *Pseudomonas* sp. 3Y2 (AAV35431, AAV35429 and AAV35426), *P. mendocina* (AAM10546 and AAM10544), *P. nitroreducens* (AAK19608), *P. pseudoalcaligenes*

(AAK19605), *P. resinovorans* (AAD26367 and AAD26365), *Pseudomonas* sp. USM7-7 (ACM90523 and ACM90522), *P. fluorescens* (AAP58480) and other uncultured bacterium (BAE02881, BAE02880, BAE02879, BAE02878, BAE02877, BAE02876, BAE02875, BAE02874, BAE02873, BAE02872, BAE02871, BAE02870, BAE02869, BAE02868, BAE02867, BAE0286, BAE02865, BAE02864, BAE02863, BAE02862, BAE02861, BAE02860, BAE02859, BAE02858, BAE02857, BAE07146, BAE07145, BAE07144, BAE07143, BAE07142, BAE07141, BAE07140, BAE07139, BAE07138, BAE07137, BAE07136, BAE07135, BAE07134, BAE07133, BAE07132, BAE07131, BAE07130, BAE07129, BAE07128, BAE07127, BAE07126, BAE07125, BAE07124, BAE07123, BAE07122, BAE07121, BAE07120, BAE07119, BAE07118, BAE07117, BAE07116, BAE07115, BAE07114, BAE07113, BAE07112, BAE07111, BAE07110, BAE07109, BAE07108, BAE07107, BAE07106, BAE07105, BAE07104, BAE07103, BAE07102, BAE07101, BAE07100, BAE07099, BAE07098, BAE07097, BAE07096, BAE07095, BAE07094, BAE07093, BAE07092, BAE07091, BAE07090, BAE07089, BAE07088, BAE07053, BAE07052, BAE07051, BAE07050, BAE07049, BAE07048, BAE07047, BAE07046, BAE07045, BAE07044, BAE07043, BAE07042, BAE07041, BAE07040, BAE07039, BAE07038, BAE07037, BAE07036, BAE07035, BAE07034, BAE07033, BAE07032, BAE07031, BAE07030, BAE07029, BAE07028, BAE07027, BAE07026, BAE07025, BAE07024, BAE07023, BAE07022, BAE07021, BAE07020, BAE07019, BAE07018, BAE07017, BAE07016, BAE07015, BAE07014, BAE07013, BAE07012, BAE07011, BAE07010, BAE07009, BAE07008, BAE07007, BAE07006, BAE07005, BAE07004, BAE07003, BAE07002, BAE07001, BAE07000, BAE06999, BAE06998, BAE06997, BAE06996, BAE06995, BAE06994, BAE06993, BAE06992, BAE06991, BAE06990, BAE06989, BAE06988, BAE06987, BAE06986, BAE06985, BAE06984, BAE06983, BAE06982, BAE06981, BAE06980, BAE06979, BAE06978, BAE06977, BAE06976, BAE06975, BAE06974, BAE06973, BAE06972, BAE06971, BAE06970, BAE06969, BAE06968, BAE06967, BAE06966, BAE06965, BAE06964, BAE06963, BAE06962, BAE06961, BAE06960, BAE06959, BAE06958, BAE06957, BAE06956, BAE06955, BAE06954, BAE06953, BAE06952, BAE06951, BAE06950, BAE06949, BAE06948, BAE06947, BAE06946, BAE06945, BAE06944, BAE06943, BAE06942, BAE06941, BAE06940, BAE06939, BAE06938, BAE06937, BAE06936, BAE06935, BAE06934, BAE06933, BAE06932, BAE06931, BAE06930, BAE06929, BAE06928, BAE06927, BAE06926, BAE06925, BAE06924, BAE06923, BAE06922, BAE06921, BAE06920, BAE06919, BAE06918, BAE06917, BAE06916, BAE06915, BAE06914, BAE06913, BAE06912, BAE06911, BAE06910, BAE06909, BAE06908, BAE06907, BAE06906, BAE06905, BAE06904, BAE06903, BAE06902, BAE06901, BAE06900, BAE06899, BAE06898, BAE06897, BAE06896, BAE06895, BAE06894, BAE06893, BAE06892, BAE06891, BAE06890, BAE06889, BAE06888, BAE06887, BAE06886, BAE06885, BAE06884, BAE06883, BAE06882, BAE06881, BAE06880, BAE06879, BAE06878, BAE06877, BAE06876, BAE06875, BAE06874, BAE06873, BAE06872, BAE06871, BAE06870, BAE06869, BAE06868, BAE06867, BAE06866, BAE06865, BAE06864, BAE06863, BAE06862, BAE06861, BAE06860, BAE06859, BAE06858, BAE06857, BAE06856, BAE06855, BAE06854, BAE06853 and BAE06852).

In various embodiments the polymer synthase can be used for the in vitro production of polymer particles by polymerising or facilitating the polymerisation of the substrates (R)-Hydroxyacyl-CoA or other CoA thioester or derivatives thereof.

In various embodiments the substrate or the substrate mixture comprises at least one optionally substituted amino acid, lactate, ester or saturated or unsaturated fatty acid, preferably acetyl-CoA.

In various embodiments the expression construct is in a high copy number vector.

In various embodiments the expression construct comprises at least one nucleic acid sequence encoding an additional polypeptide.

In various embodiments the nucleic acid sequence that codes for a fusion polypeptide comprises:

a nucleic acid sequence that codes for an ESAT6 antigen or at least one nucleic acid sequence encoding a binding domain capable of binding an ESAT6 antigen, or that codes for a CFP10 antigen or at least one nucleic acid sequence encoding a binding domain capable of binding a CFP10 antigen, or that codes for an Rv3615c antigen or at least one nucleic acid sequence encoding a binding domain capable of binding an Rv3615c antigen, or that codes for an Rv3020c antigen or at least one nucleic acid sequence encoding a binding domain capable of binding an Rv3020c antigen, contiguous with the 5' or 3' end of the nucleic acid sequence that codes for a particle-forming protein, preferably a polymer synthase, or a nucleic acid sequence that codes for an ESAT6 antigen or at least one nucleic acid sequence encoding a binding domain capable of binding an ESAT6 antigen, or that codes for a CFP10 antigen or at least one nucleic acid sequence encoding a binding domain capable of binding a CFP10 antigen, or that codes for an Rv3615c antigen or at least one nucleic acid sequence encoding a binding domain capable of binding an Rv3615c antigen, or that codes for an Rv3020c antigen or at least one nucleic acid sequence encoding a binding domain capable of binding an Rv3020c antigen, indirectly fused with the 5' or 3' end of the nucleic acid sequence that codes for a particle-forming protein, preferably a polymer synthase, through a polynucleotide linker or spacer sequence of a desired length; or a nucleic acid sequence that codes for an ESAT6 antigen or at least one nucleic acid sequence encoding a binding domain capable of binding an ESAT6 antigen, or that codes for a CFP10 antigen or at least one nucleic acid sequence encoding a binding domain capable of binding a CFP10 antigen, or that codes for an Rv3615c antigen or at least one nucleic acid sequence encoding a binding domain capable of binding an Rv3615c antigen, or that codes for an Rv3020c antigen or at least one nucleic acid sequence encoding a binding domain capable of binding an Rv3020c antigen, that is inserted into the nucleic acid sequence that codes for a particle-forming protein, preferably a polymer synthase, optionally through a polynucleotide linker or spacer sequence of a desired length; or a nucleic acid sequence that codes for a protease cleavage site spaced between the nucleic acid sequence that codes for an ESAT6 antigen or at least one nucleic acid sequence encoding a binding domain capable of binding an ESAT6 antigen, or that codes for a CFP10 antigen or at least one nucleic acid sequence encoding a binding domain capable of binding a CFP10 antigen, or that codes for an Rv3615c antigen or at least one nucleic acid sequence encoding a binding domain capable of binding an Rv3615c antigen, or that codes for an Rv3020c antigen or at least one nucleic acid sequence encoding a binding domain capable of binding an Rv3020c antigen, and the nucleic acid sequence that codes for a particle-forming protein, preferably a polymer synthase; or a nucleic acid sequence that codes for a self-splicing element spaced between the nucleic acid sequence that codes for an ESAT6 antigen or at least one nucleic acid sequence encoding a binding domain capable of binding an ESAT6 antigen, or that codes for a CFP10 antigen or at least one nucleic acid sequence encoding a binding domain capable of binding a CFP10 antigen, or that codes for an Rv3615c antigen or at least one nucleic acid sequence encoding a binding domain capable of binding an Rv3615c antigen, or that codes for an Rv3020c antigen or at least one nucleic acid sequence encoding a binding domain capable of binding an Rv3020c antigen, and the nucleic acid sequence that codes for a particle-forming protein, preferably a polymer synthase; or any combination of two or more thereof.

In various embodiments the at least one fusion polypeptide comprises:

an amino acid sequence that comprises an ESAT6 antigen or a binding domain capable of binding an ESAT6 antigen, or a CFP10 antigen or a binding domain capable of binding a CFP10 antigen, or an Rv3615c antigen or a binding domain capable of binding an Rv3615c antigen, or an Rv3020c antigen or a binding domain capable of binding an Rv3020c antigen, contiguous with the N- or C-terminal end of the amino acid sequence that comprises a particle-forming protein, preferably a polymer synthase; or an amino acid sequence that comprises an ESAT6 antigen or a binding domain capable of binding an ESAT6 antigen, or a CFP10 antigen or a binding domain capable of binding a CFP10 antigen, or an Rv3615c antigen or a binding domain capable of binding an Rv3615c antigen, or an Rv3020c antigen or a binding domain capable of binding an Rv3020c antigen, indirectly fused with the N- or C-terminal of the amino acid sequence that comprises a particle-forming protein, preferably a polymer synthase, through a peptide linker or spacer sequence of a desired length; or an amino acid sequence sequence that comprises an ESAT6 antigen or a binding domain capable of binding an ESAT6 antigen, or a CFP10 antigen or a binding domain capable of binding a CFP10 antigen, or an Rv3615c antigen or a binding domain capable of binding an Rv3615c antigen, or an Rv3020c antigen or a binding domain capable of binding an Rv3020c antigen, that is inserted into the amino acid sequence that comprises a particle-forming protein, preferably a polymer synthase, through a peptide linker or spacer sequence of a desired length; or an amino acid sequence that comprises a protease cleavage site spaced between the amino acid sequence that comprises an ESAT6 antigen or a binding domain capable of binding an ESAT6 antigen, or a CFP10 antigen or a binding domain capable of binding a CFP10 antigen, or an Rv3615c antigen or a binding domain capable of binding an Rv3615c antigen, or an Rv3020c antigen or a binding domain capable of binding an Rv3020c antigen, and the amino acid sequence that codes for a particle-forming protein, preferably a polymer synthase; or an amino acid sequence that comprises a self-splicing element spaced between the amino acid sequence that comprises an ESAT6 antigen or a binding domain capable of binding an ESAT6 antigen, or a CFP10 antigen or a binding domain capable of binding a CFP10 antigen, or an Rv3615c antigen or a binding domain capable of binding an Rv3615c antigen, or an Rv3020c antigen or a binding domain capable of binding an Rv3020c antigen, and the amino acid sequence that codes for a particle-forming protein, preferably a polymer synthase; or any combination of two or more thereof.

In certain embodiments, such as those exemplified herein, one or more of the amino acid sequences comprising an ESAT6, CFP10, Rv3615c, or Rv3020c antigen or a binding domain capable of binding an ESAT6, CFP10, Rv3615c, and Rv3020c antigen is N-terminal to the amino acid sequence that codes for a particle-forming protein, preferably a polymer synthase, and one or more of the amino acid sequences comprising an ESAT6, CFP10, Rv3615c, or Rv3020c antigen or a binding domain capable of binding an ESAT6, CFP10, Rv3615c, and Rv3020c antigen is C-terminal to the amino acid sequence that codes for a particle-forming protein, preferably a polymer synthase.

In various embodiments the expression construct comprises a constitutive or regulatable promoter system.

In various embodiments the regulatable promoter system is an inducible or repressible promoter system.

In various embodiments the regulatable promoter system is selected from LacI, Trp, phage γ and phage RNA polymerase.

In one embodiment the promoter is any strong promoter known to those skilled in the art. Suitable strong promoters comprise adenoviral promoters, such as the adenoviral major late promoter; or heterologous promoters, such as the cytomegalovirus (CMV) promoter; the respiratory syncytial virus (RSV) promoter; the simian virus 40 (SV40) promoter; inducible promoters, such as the MMT promoter, the metallothionein promoter; heat shock promoters; the albumin promoter; the ApoAI promoter; human globin promoters; viral thymidine kinase promoters, such as the Herpes simplex thymidine kinase promoter; retroviral LTRs; the b-actin promoter; human growth hormone promoters; phage promoters such as the T7, SP6 and T3 RNA polymerase promoters and the cauliflower mosaic 35S (CaMV 35S) promoter.

In various embodiments the promoter is a T7 RNA polymerase promoter, such as a T7 RNA polymerase promoter as described in PCT/NZ2006/000251, published as WO 2007/037706.

In various embodiments the cell comprises two or more different expression constructs that each encode a different fusion polypeptide.

In various embodiments the antigen capable of eliciting a cell-mediated immune response is an antigen derived from an intracellular pathogen.

In various embodiments the binding domain capable of binding the antigen capable of eliciting an immune response, such as a binding domain capable of binding an antigen capable of eliciting a cell-mediated immune response is selected from a protein, a protein fragment, a binding domain, a target-binding domain, a binding protein, a binding protein fragment, an antibody, an antibody fragment, an antibody heavy chain, an antibody light chain, a single chain antibody, a single-domain antibody (a VHH for example), a Fab antibody fragment, an Fc antibody fragment, an Fv antibody fragment, a F(ab') 2 antibody fragment, a Fab' antibody fragment, a single-chain Fv (scFv) antibody fragment, a T-cell receptor, a MHC Class I molecule, MHC Class II molecule, or a combination thereof.

For example, in various embodiments the *M. tuberculosis* or *M. bovis* antigen binding domain is selected from a protein, a protein fragment, a binding domain, a target-binding domain, a binding protein, a binding protein fragment, an antibody, an antibody fragment, an antibody heavy chain, an antibody light chain, a single chain antibody, a single-domain antibody (a VHH for example), a Fab antibody fragment, an Fc antibody fragment, an Fv antibody fragment, a F(ab')2 antibody fragment, a Fab' antibody fragment, a single-chain Fv (scFv) antibody fragment, a T-cell receptor, a MHC Class I molecule, MHC Class II molecule, or a combination thereof.

In various embodiments, the immune response is a cell-mediated immune response, such as that indicated by an IFN-γ response, in the absence of a significant IgA response, or in the absence of a significant IgE response, or in the absence of a significant IgG response, including the absence of a significant IgG1 response, or the absence of a significant IgG2 response, or in the absence of a significant IgM response.

In another example, the immune response is a humoral response without significant cell-mediated response.

It is intended that reference to a range of numbers disclosed herein (for example, 1 to 10) also incorporates reference to all rational numbers within that range (for example, 1, 1.1, 2, 3, 3.9, 4, 5, 6, 6.5, 7, 8, 9 and 10) and also any range of rational numbers within that range (for example, 2 to 8, 1.5 to 5.5 and 3.1 to 4.7) and, therefore, all sub-ranges of all ranges expressly disclosed herein are hereby expressly disclosed. These are only examples of what is specifically intended and all possible combinations of numerical values between the lowest value and the highest value enumerated are to be considered to be expressly stated in this application in a similar manner.

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

BRIEF DESCRIPTION OF THE DRAWINGS

Further aspects of the present invention will become apparent from the following description which is given by way of example only and with reference to the accompanying drawings.

FIG. 1 shows a schematic representation of hybrid genes which fusion proteins mediated production of polyester particles displaying TB antigens.

FIG. 2 depicts photomicrographs of fluorescence microscopy of recombinant *E. coli* BL21 (DE3), harboring pMCS69 and the various fusion protein encoding pET expression vectors stained with Nile red. (A) pET-14b phaC; (B) pET-14b cfp10-phaC; (C) pET-14b rv3615c-phaC; (D) pET-14b esat6-phaC; (E) pET-14b cfp10-rv3615c-phaC-esat6.

FIG. 3 presents TEM analysis of recombinant *E. coli* harbouring various plasmids (A-E) and of isolated polyester particles displaying mycobacterial antigens (F-J). (A and F) pET-14b phaC; (B and G) pET-14b cfp10-phaC; (C and H) pET-14b rv3615c-phaC, (D and I) pET-14b esat6-phaC; (E and J) pET-14b cfp10-rv3615c-phaC-esat6.

FIG. 4 presents protein profiles of polyester particles isolated from recombinant *E. coli* harbouring various plasmids with and without a protease inhibitor treatment. The fusion proteins in the polyester bead fractions were analysed by SDS-PAGE as follows: Lanes 1-6, samples with no protease inhibitor treatment and lanes 7-10 with protease inhibitor treatment. Lanes 1 and 7, molecular weight marker (Mark 12, Invitrogen); lanes 2 and 8, PhaC (WT, 63 kDa); lane 3, Rv3615c-PhaC (75.2 kDa); lane 4, ESAT6-PhaC (74.3 kDa); lanes 5 and 9, CFP10-PhaC (75.2 kDa); lanes 6 and 10, CFP10-Rv3615c-PhaC-ESAT6 (98.1 kDa). The presence of PhaC-TB antigens fusion proteins was confirmed by tryptic peptide fingerprinting using MALDI-TOF/MS (Table 3).

FIG. 5 is a model of a triple TB antigen-displaying polyester particle of the invention produced by recombinant *E. coli*.

FIG. 6 presents graphs reporting the assessment of TB antigen reactivityjn vitro. The ELISA assay is described in Materials and Methods. All measurements were conducted in triplicate. The mean of TB antigen reactivity to a specific antibody is reported ±SD. (A) Reactivity of TB antigens on the surface of polyester particles. WT (particles) is the negative control. Recombinant TB antigens (CFP10, Rv3615c, ESAT6, and the mixture of CFP10, Rv3615c and ESAT6) were used as positive controls. The testing samples are immobilized TB antigens (bead-CFP10, bead-Rv3615c, bead-ESAT6, and bead-CFP10-Rv3615c-ESAT6). The anti-CFP10 and anti-ESAT6 were mouse monoclonal antibodies and the anti-RV3615C polyclonal antibody was produced in a rabbit.* significantly higher than single antigen ($P<0.05$) (B) Control experiment; the rabbit pre-immune serum was used to replace the three specific antibodies as indicated in Figure B.

FIG. 7 presents graphs showing TB skin test response. Four diagnostic reagents, avian PPD (PPD-A), bovine PPD (PPD-B), particles displaying three TB antigens and control particles were used to skin test cattle. The result was positive if the increase in skin thickness was ≥1 mm. (A) Cattle experimentally-infected by *M. bovis*. (B) Non-infected cattle naturally exposed to environmental mycobacteria. Bar indicates median.

FIG. 8 presents a graphic depicting the construction of the plasmid encoding a 4 antigen polymer particle of the invention, pET-14b cfp10-linker-rv3615c-phaC-linker-esat6-linker-rv3020c, as described herein in Example 2.

FIG. 9 presents a Coomassie brilliant blue-stained SDS-PAGE analysis (LifeTechnologies Bolt 10% Bis-Tris, 165V×35 mins) of various samples from the preparation and purification of the 4-antigen polymer particle described herein in Example 2, as follows: Lane 1—Marker; Lane 2—Lysate; Lane 3—Detergent wash 1 (DW1); Lane 4—DW2; Lane 5—Caustic Wash; Lane 6—Pre Tangential flow filtration (Pre TFF); Lane 7—Post TFF 1; Lane 8—Post TFF 2; Lane 9—TFF end; Lane 10—Bulk Product.

FIG. 10 presents a graph depicting median skin thickness (mm) dose response data from six subjects, as described in Example 3 herein. Bovine—PPDB control, Avian—PPDA control, BB—undiluted tetravalent TB antigen-comprising polymer particles (TTPP), 3 μg—TTPP providing 3 μg total antigens, 3 μg—TTPP providing 3 μg total antigens, 3 μg—TTPP providing 3 μg total antigens, 1 μg—TTPP providing 1 μg total antigens, 0.33 μg—TTPP providing 0.33 µg total antigens, 0.11 µg—TTPP providing 0.11 µg total antigens, 0.4 µg—TTPP providing 0.4 µg total antigens, 0.1 µg—TTPP providing 0.1 µg total antigens.

Figure 11:
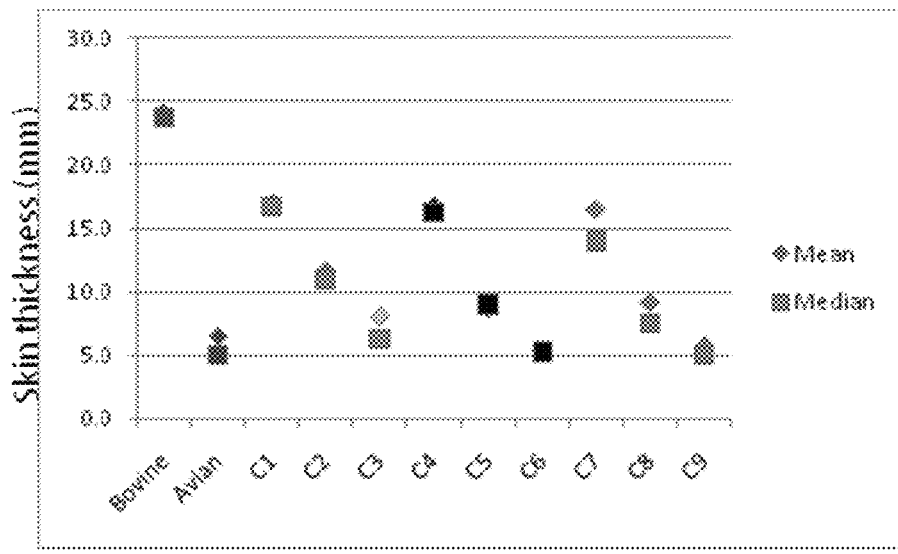

FIG. 11 presents a graph depicting mean and median skin thickness (mm) response data from six subjects in an assay of formulation effects, as described in Example 3 herein. Bovine—PPDB control, Avian—PPDA control, C1—TTPP in PBS/Dextran providing 3 µg total antigens, C2—TTPP in PBS/Dextran providing 0.11 µg total antigens, C3—TTPP in PBS/Dextran providing 0.012 µg total antigens, C4—TTPP in 2% ethanol providing 3 µg total antigens, C5—TTPP in 2% ethanol providing 0.11 µg total antigens, C6—TTPP in 2% ethanol providing 0.012 µg total antigens, C7—TTPP in 10 mM Tris (pH 8.5) providing 3 µg total antigens, C8—TTPP in 10 mM Tris (pH 8.5) providing 0.11 µg total antigens, C9—TTPP in 10 mM Tris (pH 8.5) providing 0.012 µg total antigens.

Figure 12:
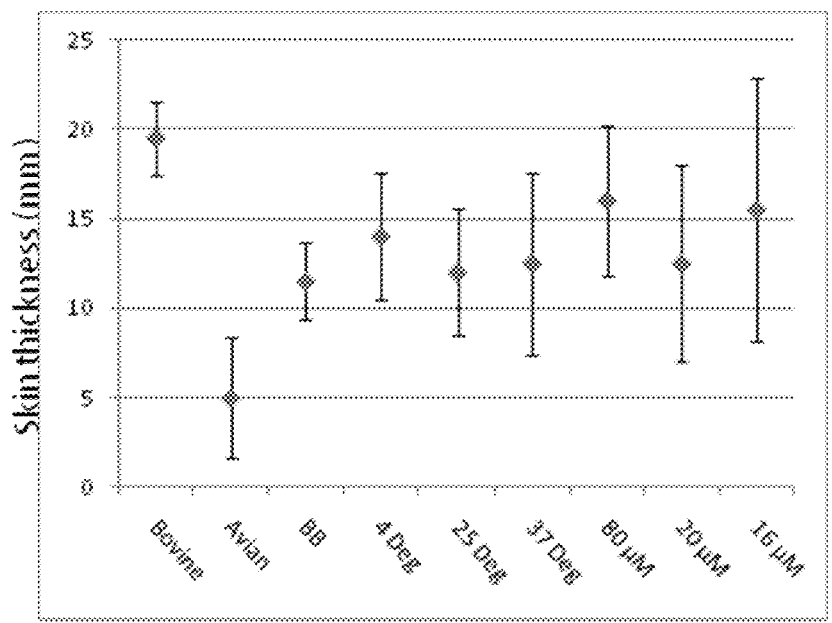

FIG. 12 presents a graph depicting median skin thickness (mm) response data from six subjects testing stability and aggregation, as described in Example 3 herein. Bovine—PPDB control, Avian—PPDA control, BB—undiluted tetravalent TB antigen-comprising polymer particles (TTPP), 4 Deg—TTPP providing 3 µg total antigens stored for 6 months at 4° C., 25 Deg—TTPP providing 3 µg total antigens stored for 6 months at 25° C., 37 Deg—TTPP providing 3 µg total antigens stored for 6 months at 37° C., 80 µm—TTPP in 2% ethanol providing 3 µg total antigens with mean particle size of 80 µm, 20 µm—TTPP in 2% ethanol providing 3 µg total antigens with mean particle size of 20 µm, 16 µm—TTPP in 2% ethanol providing 3 µg total antigens with mean particle size of 16 µm.

Figure 13A:
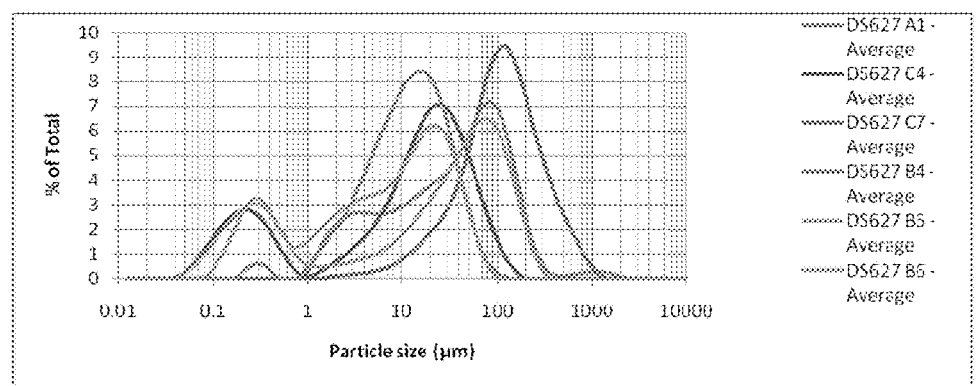
Figure 13B:
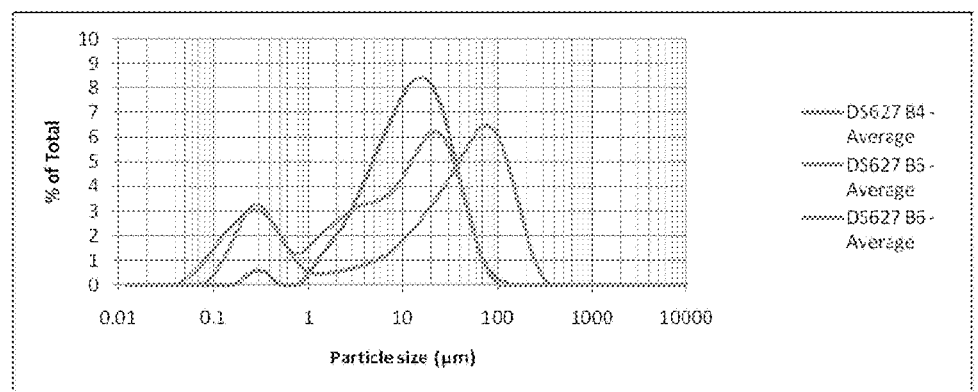

FIG. 13 presents a graph depicting average size distribution of TTPP containing compositions utilized in Example 3 herein. FIG. 13A: DS627 A1—TTPP produced in batch DS627 and formulated in PBS/Dextran providing 3 µg total antigens, DS627 C4—TTPP produced in batch DS627 and formulated in 2% ethanol providing 3 µg total antigens, DS627 C7—TTPP produced in batch DS627 and formulated in 10 mM Tris (pH 8.5) providing 3 µg total antigens, DS627 B4—TTPP produced in batch DS627 and formulated in 2% ethanol with mean particle size of 16 µm and providing 3 µg total antigens, DS627 B5—TTPP produced in batch DS627 and formulated in 2% ethanol with mean particle size of 20 µm an providing 3 µg total antigens, DS627 B6—TTPP produced in batch DS627 and formulated in 2% ethanol with mean particle size of 80 µm an providing 3 µg total antigens. FIG. 13B: DS627 B4—TTPP produced in batch DS627 and formulated in 2% ethanol with mean particle size of 16 µm and providing 3 µg total antigens, DS627 B5—TTPP produced in batch DS627 and formulated in 2% ethanol with mean particle size of 20 µm an providing 3 µg total antigens, DS627 B6—TTPP produced in batch DS627 and formulated in 2% ethanol with mean particle size of 80 µm an providing 3 µg total antigens.

Figure 14:
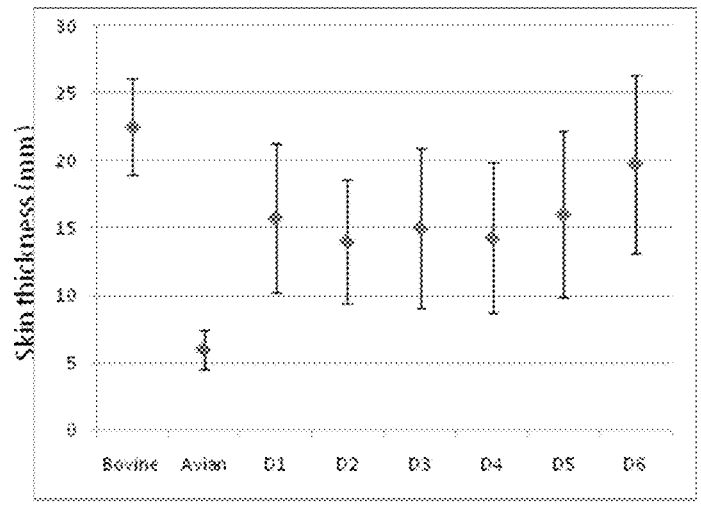

FIG. 14 presents a graph depicting median skin thickness (mm) dose response data from six subjects testing batch variability, as described in Example 3 herein. Bovine—PPDB control, Avian—PPDA control, D1—TTPP produced in batch DS498 and formulated in PBS/Dextran providing 3 µg total antigens, D2—TTPP produced in batch DS504 and formulated in PBS/Dextran providing 3 µg total antigens, D3—TTPP produced in batch DS507 and formulated in PBS/Dextran providing 3 µg total antigens, D4—TTPP produced in batch DS560 and formulated in PBS/Dextran providing 3 µg total antigens, D5—TTPP produced in batch DS585 and formulated in PBS/Dextran providing 3 µg total antigens, D6—TTPP produced in batch DS625 and formulated in PBS/Dextran providing 3 µg total antigens.

Figure 15:
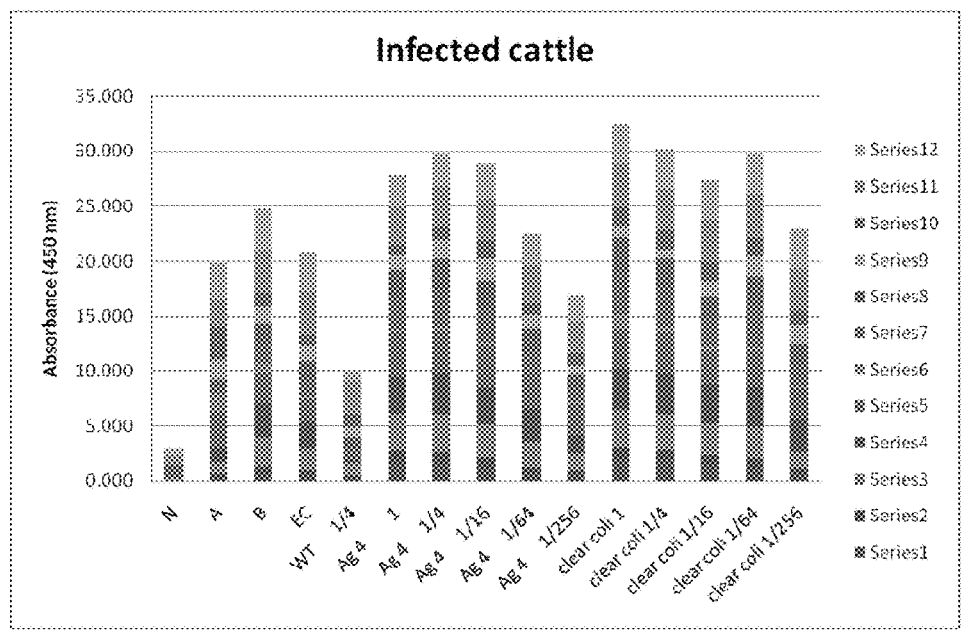
Figure 16:
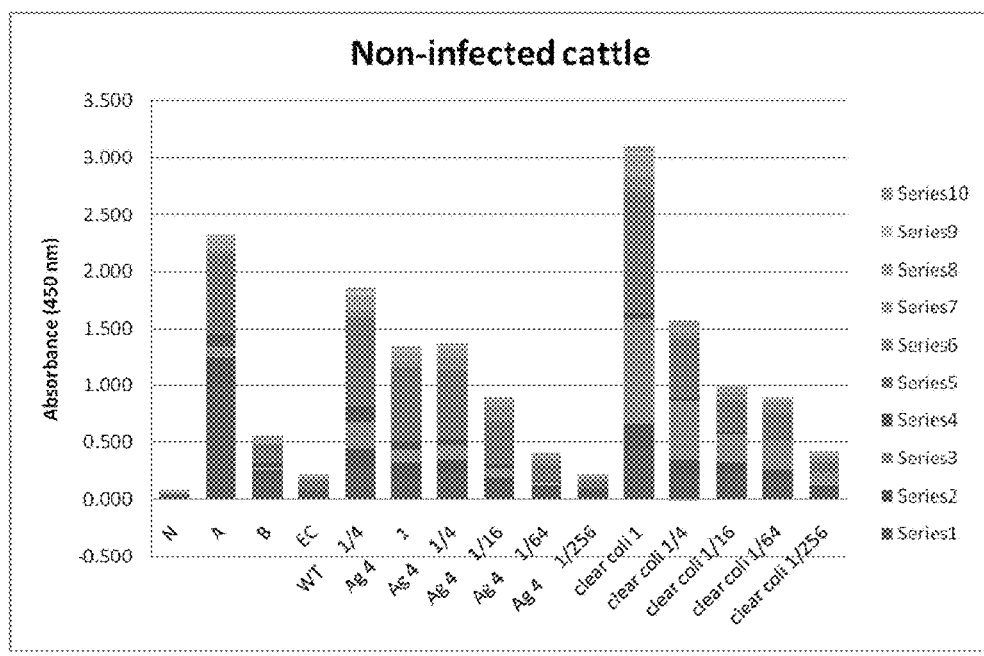

FIG. 15 presents a graph depicting IFN-γ data (absorbance at 450 nm) from 12 series of TB-infected subjects, as described in Example 4 herein. N—PBS control, A—PPDA control, B—PPDB control, EC—soluble ESAT6/CFP10 antigen (4 µg in well), WT—PhaC-only control particles, Ag 4 1—TTPP produced in LPS+ host providing 0.38 μg total antigens, Ag 4 1/4—TTPP produced in LPS+ host providing 0.1 μg total antigens, Ag 4 1/16—TTPP produced in LPS+ host providing 25 ng total antigens, Ag 4 1/64—TTPP produced in LPS+ host providing 6 ng total antigens, Ag 4 1/256—TTPP produced in LPS+ host providing 1.5 ng total antigens, clear *coli* 1—TTPP produced in LPS− host providing 0.38 μg total antigens, clear *coli* 1/4—TTPP produced in LPS− host providing 0.1 μg total antigens, clear *coli* 1/16—TTPP produced in LPS− host providing 25 ng total antigens, clear *coli* 1/64—TTPP produced in LPS− host providing 6 ng total antigens, clear *coli* 1/256—TTPP produced in LPS− host providing 1.5 ng total antigens.

FIG. 16 presents a graph depicting IFN-γ data (absorbance at 450 nm) from 10 series of non-infected subjects, as described in Example 4 herein. N—PBS control, A—PPDA control, B PPDB control, EC—soluble ESAT6/CFP10 antigen (4 μg in well), WT—PhaC-only control particles, Ag 4 1—TTPP produced in LPS+ host providing 0.38 μg total antigens, Ag 4 1/4—TTPP produced in LPS+ host providing 0.1 μg total antigens, Ag 4 1/16—TTPP produced in LPS+ host providing 25 ng total antigens, Ag 4 1/64—TTPP produced in LPS+ host providing 6 ng total antigens, Ag 4 1/256—TTPP produced in LPS+ host providing 1.5 ng total antigens, clear *coli* 1—TTPP produced in LPS− host providing 0.38 μg total antigens, clear *coli* 1/4—TTPP produced in LPS− host providing 0.1 μg total antigens, clear *coli* 1/16—TTPP produced in LPS− host providing 25 ng total antigens, clear *coli* 1/64—TTPP produced in LPS− host providing 6 ng total antigens, clear *coli* 1/256—TTPP produced in LPS− host providing 1.5 ng total antigens.

DETAILED DESCRIPTION

The present invention relates to polymer particles and uses thereof. In particular the present invention relates to functionalised polymer particles, for example, processes of production of functionalised polymer particles, and uses thereof in the diagnosis, treatment or prevention of *tuberculosis*.

Functionalised polymer particles of the present invention may comprise one or more surface-bound fusion polypeptides, and may also comprise one or more substances incorporated or adsorbed into the polymer particle core, one or more substances bound to surface bound fusion polypeptides, or a combination thereof.

1. Definitions

The term "coding region" or "open reading frame" (ORF) refers to the sense strand of a genomic DNA sequence or a cDNA sequence that is capable of producing a transcription product and/or a polypeptide under the control of appropriate regulatory sequences. The coding sequence is identified by the presence of a 5' translation start codon and a 3' translation stop codon. When inserted into a genetic construct, a "coding sequence" is capable of being expressed when it is operably linked to promoter and terminator sequences.

The term "comprising" as used in this specification means "consisting at least in part of." When interpreting each statement in this specification that includes the term "comprising", features other than that or those prefaced by the term may also be present. Related terms such as "comprise" and "comprises" are to be interpreted in the same manner.

The term "coupling reagent" as used herein refers to an inorganic or organic compound that is suitable for binding at least one substance or a further coupling reagent that is suitable for binding a coupling reagent on one side and at least one substance on the other side. Examples of suitable coupling reagents, as well as exemplary methods for their use including methods suitable for the chemical modification of particles or fusion proteins of the present invention, are presented in PCT/DE2003/002799, published as WO 2004/020623 (Bernd Rehm), herein incorporated by reference in its entirety.

The term "expression construct" refers to a genetic construct that includes elements that permit transcribing the insert polynucleotide molecule, and, optionally, translating the transcript into a polypeptide. An expression construct typically comprises in a 5' to 3' direction:
(1) a promoter, functional in the host cell into which the construct will be introduced,
(2) the polynucleotide to be expressed, and
(3) a terminator functional in the host cell into which the construct will be introduced.

Expression constructs of the invention are inserted into a replicable vector for cloning or for expression, or are incorporated into the host genome.

Examples of expression constructs amenable for adaptation for use in the present invention are provided in PCT/DE2003/002799 published as WO 2004/020623 (Bernd Rehm) and PCT/NZ2006/000251 published as WO 2007/037706 (Bernd Rehm) which are each herein incorporated by reference in their entirety.

The terms "form a polymer particle" and "formation of polymer particles", as used herein, refer to the activity of a particle-forming protein as discussed herein.

A "fragment" of a polypeptide is a subsequence of the polypeptide that performs a function that is required for the enzymatic or binding activity and/or provides three dimensional structure of the polypeptide.

The term "fusion polypeptide", as used herein, refers to a polypeptide comprising two or amino acid sequences, for example two or more polypeptide domains, fused through respective amino and carboxyl residues by a peptide linkage to form a single continuous polypeptide. It should be understood that the two or more amino acid sequences can either be directly fused or indirectly fused through their respective amino and carboxyl terimini through a linker or spacer or an additional polypeptide.

In one embodiment, one of the amino acid sequences comprising the fusion polypeptide comprises a particle-forming protein.

In particularly contemplated embodiments of the invention, two or more of the amino acid sequences comprising the fusion polypeptide comprise a *M. tuberculosis* antigen selected from the group comprising an ESAT6 antigen, a binding domain capable of binding an ESAT6 antigen, a CFP10 antigen, a binding domain capable of binding a CFP10 antigen, an Rv3615c antigen, a binding domain capable of binding an Rv3615c antigen, or a fusion partner.

In other particularly contemplated embodiments of the invention, three or more of the amino acid sequences comprising the fusion polypeptide comprise a *M. tuberculosis* antigen selected from the group comprising an ESAT6 antigen, a binding domain capable of binding an ESAT6 antigen, a CFP10 antigen, a binding domain capable of binding a CFP10 antigen, an Rv3615c antigen, a binding domain capable of binding an Rv3615c antigen, an Rv3020c antigen, a binding domain capable of binding an Rv3020c antigen, or a fusion partner.

The term "fusion partner" as used herein refers to a polypeptide such as a protein, a protein fragment, a binding domain, a target-binding domain, a binding protein, a binding protein fragment, an antibody, an antibody fragment, an antibody heavy chain, an antibody light chain, a single chain antibody, a single-domain antibody (a VHH for example), a Fab antibody fragment, an Fc antibody fragment, an Fv antibody fragment, a F(ab')2 antibody fragment, a Fab' antibody fragment, a single-chain Fv (scFv) antibody fragment, an antibody binding domain (a ZZ domain for example), an antigen, an antigenic determinant, an epitope, a hapten, an immunogen, an immunogen fragment, biotin, a biotin derivative, an avidin, a streptavidin, a substrate, an enzyme, an abzyme, a co-factor, a receptor, a receptor fragment, a receptor subunit, a receptor subunit fragment, a ligand, an inhibitor, a hormone, a lectin, a polyhistidine, a coupling domain, a DNA binding domain, a FLAG epitope, a cysteine residue, a library peptide, a reporter peptide, an affinity purification peptide, or any combination of any two or more thereof.

It should be understood that two or more polypeptides listed above can form the fusion partner.

In one embodiment the amino acid sequences of the fusion polypeptide are indirectly fused through a linker or spacer, the amino acid sequences of said fusion polypeptide arranged in the order of polymer synthase-linker-antigen capable of eliciting an immune response, or antigen capable of eliciting an immune response-linker-polymer synthase, or polymer synthase-linker-binding domain of an antigen capable of eliciting an immune response, or binding domain of antigen capable of eliciting an immune response-linker-polymer synthase, for example. In other embodiments the amino acid sequences of the fusion polypeptide are indirectly fused through or comprise an additional polypeptide arranged in the order of polymer synthase-additional polypeptide-antigen capable of eliciting an immune response or polymer synthase-additional polypeptide-binding domain of an antigen capable of eliciting an immune response, or polymer synthase-linker-antigen capable of eliciting an immune response-additional polypeptide or polymer synthase-linker-binding domain of an antigen capable of eliciting an immune response—additional polypeptide. Again, N-terminal extensions of the polymer synthase are expressly contemplated herein.

Immune responses include cell-mediated and humoral immune responses.

In one embodiment the amino acid sequences of the fusion polypeptide are indirectly fused through a linker or spacer, the amino acid sequences of said fusion polypeptide arranged in the order of polymer synthase-linker-*M. tuberculosis* or *M. bovis* antigen or *M. tuberculosis* or *M. bovis* antigen-linker-polymer synthase, or polymer synthase-linker-*M. tuberculosis* or *M. bovis* antigen binding domain or *M. tuberculosis* or *M. bovis* antigen binding domain-linker-polymer synthase, for example. In other embodiments the amino acid sequences of the fusion polypeptide are indirectly fused through or comprise an additional polypeptide arranged in the order of polymer synthase-additional polypeptide-*M. tuberculosis* or *M. bovis* antigen or polymer synthase-additional polypeptide—*M. tuberculosis* or *M. bovis* antigen binding domain, or polymer synthase-linker-

*M. tuberculosis* or *M. bovis* antigen-additional polypeptide or polymer synthase-linker-*M. tuberculosis* or *M. bovis* antigen binding domain-additional polypeptide. Again, N-terminal extensions of the polymer synthase are expressly contemplated herein.

A fusion polypeptide according to the invention may also comprise one or more polypeptide sequences inserted within the sequence of another polypeptide. For example, a polypeptide sequence such as a protease recognition sequence are inserted into a variable region of a protein comprising a particle binding domain.

Conveniently, a fusion polypeptide of the invention are encoded by a single nucleic acid sequence, wherein the nucleic acid sequence comprises at least two subsequences each encoding a polypeptide or a polypeptide domain. In certain embodiments, the at least two subsequences will be present "in frame" so as comprise a single open reading frame and thus will encode a fusion polypeptide as contemplated herein. In other embodiments, the at least two subsequences are present "out of frame", and are separated by a ribosomal frame-shifting site or other sequence that promotes a shift in reading frame such that, on translation, a fusion polypeptide is formed. In certain embodiments, the at least two subsequences are contiguous. In other embodiments, such as those discussed above where the at least two polypeptides or polypeptide domains are indirectly fused through an additional polypeptide, the at least two subsequences are not contiguous.

Reference to a "binding domain" or a "domain capable of binding" is intended to mean one half of a complementary binding pair and may include binding pairs from the list above. For example, antibody-antigen, antibody-antibody binding domain, biotin-streptavidin, receptor-ligand, enzyme-inhibitor pairs. A target-binding domain will bind a target molecule in a sample, and are an antibody or antibody fragment, for example. A polypeptide-binding domain will bind a polypeptide, and are an antibody or antibody fragment, or a binding domain from a receptor or signalling protein, for example.

Examples of substances that are bound by a binding domain include a protein, a protein fragment, a peptide, a polypeptide, a polypeptide fragment, an antibody, an antibody fragment, an antibody binding domain, an antigen, an antigen fragment, an antigenic determinant, an epitope, a hapten, an immunogen, an immunogen fragment, a pharmaceutically active agent, a biologically active agent, an adjuvant or any combination of any two or more thereof. Such substances are "target components" in a sample that is analysed according to a method of the invention.

Accordingly, a "domain capable of binding [an antigen]" and grammatical equivalents will be understood to refer to one component in a complementary binding pair, wherein the other component is the specified antigen.

Accordingly, a "*M. tuberculosis* antigen binding domain" is a domain that is able to bind one or more *M. tuberculosis* antigens.

A "*M. tuberculosis* antigen" as used herein is an antigen derived from *M. tuberculosis*. Likewise, other antigens are identified by the organism from which they are derived.

The phrase "antigen capable of eliciting an immune response" refers to an antigen that, when contacted with one or more agentsagents of the immune system, such as one or more antibodies or one or more cells, is able to elicit or upregulate the responsiveness of the immune system, such as, for example, an upregulation in one or more T cell populations, such as for example increased CD8+ T-cell or CD4+ T cell activity or number, or an upregulation in one or more B cell populations, such as one or more B cell populations capable of producing antibodies specific to the antigen or capable of binding the antigen, or an increase in the amount or activity of one or more populations of antibodies.

The phrase "antigen capable of eliciting a cell-mediated response" refers to an antigen that, when contacted with one or more cells of the immune system, is able to elicit or upregulate the responsiveness of the immune system, such as, for example, an upregulation in one or more T cell populations, such as for example increased CD8+ T-cell or CD4+ T cell activity or number.

The term "genetic construct" refers to a polynucleotide molecule, usually double-stranded DNA, which may have inserted into it another polynucleotide molecule (the insert polynucleotide molecule) such as, but not limited to, a cDNA molecule. A genetic construct may contain the necessary elements that permit transcribing the insert polynucleotide molecule, and, optionally, translating the transcript into a polypeptide. The insert polynucleotide molecule are derived from the host cell, or are derived from a different cell or organism and/or are a recombinant polynucleotide. Once inside the host cell the genetic construct becomes integrated in the host chromosomal DNA. In one example the genetic construct is linked to a vector.

The term "host cell" refers to a bacterial cell, a fungi cell, yeast cell, a plant cell, an insect cell or an animal cell such as a mammalian host cell that is either 1) a natural PHA particle producing host cell, or 2) a host cell carrying an expression construct comprising nucleic acid sequences encoding at least a thiolase and a reductase and optionally a phasin. Which genes are required to augment what the host cell lacks for polymer particle formation will be dependent on the genetic makeup of the host cell and which substrates are provided in the culture medium.

The term "linker or spacer" as used herein relates to an amino acid or nucleotide sequence that indirectly fuses two or more polypeptides or two or more nucleic acid sequences encoding two or more polypeptides. In some embodiments the linker or spacer is about 1, 5, 10, 15, 20, 25, 30, 35, 40, 45, 50, 55, 60, 65, 70, 75, 80, 85, 90, 95 or about 100 amino acids or nucleotides in length. In other embodiments the linker or spacer is about 100, 125, 150, 175, 200, 225, 250, 275, 300, 325, 350, 375, 400, 450, 500, 550, 600, 650, 700, 750, 800, 850, 900, 950 or about 1000 amino acids or nucleotides in length. In still other embodiments the linker or spacer is from about 1 to about 1000 amino acids or nucleotides in length, from about 10 to about 1000, from about 50 to about 1000, from about 100 to about 1000, from about 200 to about 1000, from about 300 to about 1000, from about 400 to about 1000, from about 500 to about 1000, from about 600 to about 1000, from about 700 to about 1000, from about 800 to about 1000, or from about 900 to about 1000 amino acids or nucleotides in length.

In one embodiment the linker or spacer may comprise a restriction enzyme recognition site. In another embodiment the linker or spacer may comprise a protease cleavage recognition sequence such as enterokinase, thrombin or Factor Xa recognition sequence, or a self-splicing element such as an intein. In another embodiment the linker or spacer facilitates independent folding of the fusion polypeptides.

The term "mixed population", as used herein, refers to two or more populations of entities, each population of entities within the mixed population differing in some respect from another population of entities within the mixed population. For example, when used in reference to a mixed population of expression constructs, this refers to two or more populations of expression constructs where each population of expression construct differs in respect of the fusion polypeptide encoded by the members of that population, or in respect of some other aspect of the construct, such as for example the identity of the promoter present in the construct. Alternatively, when used in reference to a mixed population of fusion polypeptides, this refers to two or more populations of fusion polypeptides where each population of fusion polypeptides differs in respect of the polypepetides, such as polymer synthase, the antigen capable of eliciting a cell-mediated immune response, or the binding domain capable of binding an antigen capable of eliciting a cell-mediated immune response, the members that population contains. For example, in the context of use in the treatment of tuberculosis, a mixed population of fusion polypeptides refers to two or more populations of fusion polypeptides where each population of fusion polypeptides differs in respect of the polypepetides, such as polymer synthase, the M. tuberculosis antigens, or the M. tuberculosis antigen binding domains, the members that population contains. Still further, when used in reference to a mixed population of polymer particles, this refers to two or more populations of polymer particles where each population of polymer particles differs in respect of the fusion polypeptide or fusion polypeptides the members of that population carry.

The term "nucleic acid" as used herein refers to a single- or double-stranded polymer of deoxyribonucleotide, ribonucleotide bases or known analogues of natural nucleotides, or mixtures thereof. The term includes reference to a specified sequence as well as to a sequence complimentary thereto, unless otherwise indicated. The terms "nucleic acid" and "polynucleotide" are used herein interchangeably.

"Operably-linked" means that the sequenced to be expressed is placed under the control of regulatory elements that include promoters, tissue-specific regulatory elements, temporal regulatory elements, enhancers, repressors and terminators.

The term "over-expression" generally refers to the production of a gene product in a host cell that exceeds levels of production in normal or non-transformed host cells. The term "overexpression" when used in relation to levels of messenger RNA preferably indicates a level of expression at least about 3-fold higher than that typically observed in a host cell in a control or non-transformed cell. More preferably the level of expression is at least about 5-fold higher, about 10-fold higher, about 15-fold higher, about 20-fold higher, about 25-fold higher, about 30-fold higher, about 35-fold higher, about 40-fold higher, about 45-fold higher, about 50-fold higher, about 55-fold higher, about 60-fold higher, about 65-fold higher, about 70-fold higher, about 75-fold higher, about 80-fold higher, about 85-fold higher, about 90-fold higher, about 95-fold higher, or about 100-fold higher or above, than typically observed in a control host cell or non-transformed cell.

Levels of mRNA are measured using any of a number of techniques known to those skilled in the art including, but not limited to, Northern blot analysis and RT-PCR, including quantitative RT-PCR.

The term "particle-forming protein", as used herein, refers to proteins involved in the formation of the particle. It may, for example, be selected from the group of proteins which comprises a polymer depolymerase, a polymer regulator, a polymer synthase and a particle size-determining protein. Preferably the particle-forming protein is selected from the group comprising a thiolase, a reductase, a polymer synthase and a phasin. A particle-forming protein such as a synthase may catalyse the formation of a polymer particle by polymerising a substrate or a derivative of a substrate to form a polymer particle. Alternatively, a particle-forming protein such as a thiolase, a reductase or a phasin may facilitate the formation of a polymer particle by facilitating polymerisation. For example, a thiolase or reductase may catalyse production of suitable substrates for a polymerase. A phasin may control the size of the polymer particle formed. Preferably the particle-forming protein comprises a particle binding domain and a particle forming domain.

As used herein, the term "particle-forming reaction mixture" refers to at least a polymer synthase substrate if the host cell or expression construct comprises a synthase catalytic domain or a polymer synthase and its substrate if the host cell or expression construct comprises another particle-forming protein or a particle binding domain that is not a polymer synthase catalytic domain.

A "particle size-determining protein" refers to a protein that controls the size of the polymer particles. It may for example be derived from the family of phasin-like proteins, preferably selected from the those from the genera Ralstonia, Alcaligenes and Pseudomonas, more preferably the phasin gene phaP from Ralstonia eutropha and the phasin gene phaF from Pseudomonas oleovorans. Phasins are amphiphilic proteins with a molecular weight of 14 to 28 kDa which bind tightly to the hydrophobic surface of the polymer particles. It may also comprise other host cell proteins that bind particles and influence particle size.

It will be appreciated that pathogens are typically host-specific. Accordingly, the methods and compositions of the invention are amenable to use in a particular host species against a particular pathogen, including against a species-specific pathogen. For example, embodiments for human subjects, for example for use in the detection of human-specific tuberculosis pathogens, will typically focus on Mycobacterium tuberculosis.

In other examples, embodiments for use with bovine, cervine and ovine subjects will typically target Mycobacterium spp., including for example e.g M. bovis, M. tuberculosis, M. leprae, M. kansasii, M. avium, M. avium paratuberculosis, and other Mycobacterium spp.

Accordingly, a "subject" is an animal, such as a mammal, including a mammalian companion animal or a human. Representative companion animals include feline, equine, and canine. Representative agricultural animals include bovine, ovine, cervine, and porcine. In one embodiment the human is an adult, a child, or an infant, including an immunocompromised adult, child, or infant, or an adult, a child or an infant vaccinated against, infected with, exposed to or at risk of infection or exposure to a pathogen.

The term "treat" and its derivatives (including "treatment") should be interpreted in their broadest possible context. The term should not be taken to imply that a subject is treated until total recovery. Accordingly, "treat" broadly includes amelioration and/or prevention of the onset of the symptoms or severity of a particular condition.

A "polymer regulator" as used herein refers to a protein which regulates the transcription of the genes phaA, phaB and phaC involved in the formation of the polymer particles. It is withdrawn from transcription regulation by binding to the particle surface. One example of such a regulator is the phasin repressor (phaR) from R. eutropha YP_725943, which binds to the promoter of a phasin-like gene, the expression product of which regulates the size of polymer particles formed, and prevents the gene from being read. Because the phasin repressor is bound on the surface of the polymer particles formed, this site on the promoter is released and transcription of the underlying gene can begin.

A "polymer synthase" as used herein refers to a protein which is capable of catalysing the formation of a polymer particle by polymerising a substrate or a derivative of a substrate to form a polymer particle. The nucleotide sequences of 88 PHA synthase genes from >45 different bacteria have been obtained, differing in primary structure, substrate specificity and subunit composition (Rehm, 2007).

A polymer synthase comprises at least the synthase catalytic domain at the C-terminus of the synthase protein that mediates polymerisation of the polymer and attachment of the synthase protein to the particle core. Polymer synthases for use in the present invention are described in detail in Rehm, 2003, which is herein incorporated by reference in its entirety. For example, the polymer synthase is a PHA synthase from the class 1 genera *Acinetobacter, Vibrio, Aeromonas, Chromobacterium, Pseudomonas, Zoogloea, Alcaligenes, Delftia, Burkholderia, Ralstonia, Rhodococcus, Gordonia, Rhodobacter, Paracoccus, Rickettsia, Caulobacter, Methylobacterium, Azorhizobium, Agrobacterium, Rhizobium, Sinorhizobium, Rickettsia, Crenarchaeota, Synechocystis, Ectothiorhodospira, Thiocapsa, Thyocystis* and *Allochromatium*, the class 2 genera *Burkholderia* and *Pseudomonas*, or the class 4 genera *Bacillus*, more preferably from the group comprising class 1 *Acinetobacter* sp. RA3849, *Vibrio cholerae, Vibrio parahaemolyticus, Aeromonas punctata* FA440, *Aeromonas hydrophila, Chromobacterium violaceum, Pseudomonas* sp. 61-3, *Zoogloea ramigera, Alcaligenes latus, Alcaligenes* sp. SH-69, *Delftia acidovorans, Burkholderia* sp. DSMZ9242, *Ralstonia eutrophia* H16, *Burkholderia cepacia, Rhodococcus rubber* PP2, *Gordonia rubripertinctus, Rickettsia prowazekii, Synechocystis* sp. PCC6803, *Ectothiorhodospira shaposhnikovii* N1, *Thiocapsa pfennigii* 9111, *Allochromatium vinosum* D, *Thyocystis violacea* 2311, *Rhodobacter sphaeroides, Paracoccus denitrificans, Rhodobacter capsulatus, Caulobacter crescentus, Methylobacterium extorquens, Azorhizobium caulinodans, Agrobacterium tumefaciens, Sinorhizobium meliloti* 41, *Rhodospirillum rubrum* HA, and *Rhodospirillum rubrum* ATCC25903, class 2 *Burkholderia caryophylli, Pseudomonas chloraphis, Pseudomonas* sp. 61-3, *Pseudomonas putida* U, *Pseudomonas oleovorans, Pseudomonas aeruginosa, Pseudomonas resinovorans, Pseudomonas stutzeri, Pseudomonas mendocina, Pseudomonas pseudolcaligenes, Pseudomonas putida* BM01, *Pseudomonas nitroreducins, Pseudomonas chloraphis*, and class 4 *Bacillus megaterium* and *Bacillus* sp. INT005.

Other polymer synthases amenable to use in the present invention include polymer synthases, each identified by it accession number, from the following organisms: *C. necator* (AY836680), *P. aeruginosa* (AE004091), *A. vinosum* (AB205104), *B. megaterium* (AF109909), *H. marismortui* (YP137339), *P. aureofaciens* (AB049413), *P. putida* (AF150670), *R. eutropha* (A34341), *T. pfennigii* (X93599), *A. punctata* (O32472), *Pseudomonas* sp. 61-3 (AB014757 and AB014758), *R. sphaeroides* (AAA72004, *C. violaceum* (AAC69615), *A. borkumensis* SK2 (CAL17662), *A. borkumensis* SK2 (CAL16866), *R. sphaeroides* KD131 (ACM01571 AND YP002526072), *R. opacus* B4 (BAH51880 and YP002780825), *B. multivorans* ATCC 17616 (YP001946215 and BAG43679), *A. borkumensis* SK2 (YP693934 and YP693138), *R. rubrum* (AAD53179), gamma proteobacterium HTCC5015 (ZP05061661 and EDY86606), *Azoarcus* sp. BH72 (YP932525), *C. violaceum* ATCC 12472 (NP902459), *Limnobacter* sp. MED105 (ZP01915838 and EDM82867), *M. algicola* DG893 (ZP01895922 and EDM46004), *R. sphaeroides* (CAA65833), *C. violaceum* ATCC 12472 (AAQ60457), *A. latus* (AAD10274, AAD01209 and AAC83658), *S. maltophilia* K279a (CAQ46418 and YP001972712), *R. solanacearum* IPO1609 (CAQ59975 and YP002258080), *B. multivorans* ATCC 17616 (YP001941448 and BAG47458), *Pseudomonas* sp. g113 (ACJ02400), *Pseudomonas* sp. g106 (ACJ02399), *Pseudomonas* sp. g101 (ACJ02398), *R.* sp. g132 (ACJ02397), *R. leguminosarum* bv. *viciae* 3841 (CAK10329 and YP770390), *Azoarcus* sp. BH72 (CAL93638), *Pseudomonas* sp. LDC-5 (AAV36510), *L. nitroferrum* 2002 (ZP03698179), *Thauera* sp. MZ1T (YP002890098 and ACR01721), *M. radiotolerans* JCM 2831 (YP001755078 and ACB24395), *Methylobacterium* sp. 4-46 (YP001767769 and ACA15335), *L. nitroferrum* 2002 (EEG08921), *P. denitrificans* (BAA77257), *M. gryphiswaldense* (ABG23018), *Pseudomonas* sp. USM4-55 (ABX64435 and ABX64434), *A. hydrophila* (AAT77261 and AAT77258), *Bacillus* sp. INT005 (BAC45232 and BAC45230), *P. putida* (AAM63409 and AAM63407), *G. rubripertinctus* (AAB94058), *B. megaterium* (AAD05260), *D. acidovorans* (BAA33155), *P. seriniphilus* (ACM68662), *Pseudomonas* sp. 14-3 (CAK18904), *Pseudomonas* sp. LDC-5 (AAX18690), *Pseudomonas* sp. PC17 (ABV25706), *Pseudomonas* sp. 3Y2 (AAV35431, AAV35429 and AAV35426), *P. mendocina* (AAM10546 and AAM10544), *P. nitroreducens* (AAK19608), *P. pseudoalcaligenes* (AAK19605), *P. resinovorans* (AAD26367 and AAD26365), *Pseudomonas* sp. USM7-7 (ACM90523 and ACM90522), *P. fluorescens* (AAP58480) and other uncultured bacterium (BAE02881, BAE02880, BAE02879, BAE02878, BAE02877, BAE02876, BAE02875, BAE02874, BAE02873, BAE02872, BAE02871, BAE02870, BAE02869, BAE02868, BAE02867, BAE0286, BAE02865, BAE02864, BAE02863, BAE02862, BAE02861, BAE02860, BAE02859, BAE02858, BAE02857, BAE07146, BAE07145, BAE07144, BAE07143, BAE07142, BAE07141, BAE07140, BAE07139, BAE07138, BAE07137, BAE07136, BAE07135, BAE07134, BAE07133, BAE07132, BAE07131, BAE07130, BAE07129, BAE07128, BAE07127, BAE07126, BAE07125, BAE07124, BAE07123, BAE07122, BAE07121, BAE07120, BAE07119, BAE07118, BAE07117, BAE07116, BAE07115, BAE07114, BAE07113, BAE07112, BAE07111, BAE07110, BAE07109, BAE07108, BAE07107, BAE07106, BAE07105, BAE07104, BAE07103, BAE07102, BAE07101, BAE07100, BAE07099, BAE07098, BAE07097, BAE07096, BAE07095, BAE07094, BAE07093, BAE07092, BAE07091, BAE07090, BAE07089, BAE07088, BAE07053, BAE07052, BAE07051, BAE07050, BAE07049, BAE07048, BAE07047, BAE07046, BAE07045, BAE07044, BAE07043, BAE07042, BAE07041, BAE07040, BAE07039, BAE07038, BAE07037, BAE07036, BAE07035, BAE07034, BAE07033, BAE07032, BAE07031, BAE07030, BAE07029, BAE07028, BAE07027, BAE07026, BAE07025, BAE07024, BAE07023, BAE07022, BAE07021, BAE07020, BAE07019, BAE07018, BAE07017, BAE07016, BAE07015, BAE07014, BAE07013, BAE07012, BAE07011, BAE07010, BAE07009, BAE07008, BAE07007, BAE07006, BAE07005, BAE07004, BAE07003, BAE07002, BAE07001, BAE07000, BAE06999, BAE06998, BAE06997, BAE06996, BAE06995, BAE06994, BAE06993, BAE06992, BAE06991, BAE06990, BAE06989, BAE06988, BAE06987, BAE06986, BAE06985, BAE06984, BAE06983, BAE06982, BAE06981, BAE06980, BAE06979, BAE06978, BAE06977, BAE06976, BAE06975, BAE06974, BAE06973, BAE06972, BAE06971, BAE06970, BAE06969, BAE06968, BAE06967, BAE06966, BAE06965, BAE06964, BAE06963, BAE06962, BAE06961, BAE06960, BAE06959, BAE06958, BAE06957, BAE06956, BAE06955, BAE06954, BAE06953, BAE06952, BAE06951, BAE06950, BAE06949, BAE06948, BAE06947, BAE06946, BAE06945, BAE06944, BAE06943, BAE06942, BAE06941, BAE06940, BAE06939, BAE06938, BAE06937, BAE06936, BAE06935, BAE06934, BAE06933, BAE06932, BAE06931, BAE06930, BAE06929, BAE06928, BAE06927, BAE06926, BAE06925, BAE06924, BAE06923, BAE06922, BAE06921, BAE06920, BAE06919, BAE06918, BAE06917, BAE06916, BAE06915, BAE06914, BAE06913, BAE06912, BAE06911, BAE06910, BAE06909, BAE06908, BAE06907, BAE06906, BAE06905, BAE06904, BAE06903, BAE06902, BAE06901, BAE06900, BAE06899, BAE06898, BAE06897, BAE06896, BAE06895, BAE06894, BAE06893, BAE06892, BAE06891, BAE06890, BAE06889, BAE06888, BAE06887, BAE06886, BAE06885, BAE06884, BAE06883, BAE06882, BAE06881, BAE06880, BAE06879, BAE06878, BAE06877, BAE06876, BAE06875, BAE06874, BAE06873, BAE06872, BAE06871, BAE06870, BAE06869, BAE06868, BAE06867, BAE06866, BAE06865, BAE06864, BAE06863, BAE06862, BAE06861, BAE06860, BAE06859, BAE06858, BAE06857, BAE06856, BAE06855, BAE06854, BAE06853 and BAE06852).

The N-terminal fragment of PHA synthase protein (about amino acids 1 to 200, or 1 to 150, or 1 to 100) is highly variable and in some examples is deleted or replaced by an antigen, an antigen binding domain, or another fusion partner without inactivating the enzyme or preventing covalent attachment of the synthase via the polymer particle binding domain (i.e. the C-terminal fragment) to the polymer core. The polymer particle a binding domain capable of binding the synthase comprises at least the catalytic domain of the synthase protein that mediates polymerisation of the polymer core and formation of the polymer particles.

In some embodiments the C-terminal fragment of PHA synthase protein is modified, partially deleted or partially replaced by an antigen capable of eliciting an immune response, a binding domain capable of binding an antigen capable of eliciting an immune response, or another fusion partner without inactivating the enzyme or preventing covalent attachment of the synthase to the polymer particle.

In certain cases, the antigen capable of eliciting an immune response, the binding domain capable of binding an antigen capable of binding an immune response, or another fusion partner are fused to the N-terminus or to the C-terminus of PHA synthase protein without inactivating the enzyme or preventing covalent attachment of the synthase to the polymer particle. Similarly, in other cases the antigen capable of eliciting an immune response, the binding domain capable of binding an antigen capable of eliciting an immune response, or another fusion partner are inserted within the PHA synthase protein, or indeed within the particle-forming protein. Examples of PhaC fusions are known in the art and presented herein.

In one example, the N-terminal fragment of PHA synthase protein (about amino acids 1 to 200, or 1 to 150, or 1 to 100) is highly variable and is deleted or replaced by a *M. tuberculosis* or *M. bovis* antigen, a *M. tuberculosis* or *M. bovis* antigen binding domain, or another fusion partner without inactivating the enzyme or preventing covalent attachment (covalent attachment occurs through the active site from which the nascent polyester protrudes) of the synthase via the polymer particle binding domain (i.e. the C-terminal fragment (this domain binds via hydrophobic interaction)) to the polymer particle. The polymer particle binding domain of the synthase comprises at least the catalytic domain of the synthase protein that mediates polymerisation of the polymer particle and formation of the polymer particles.

The C-terminal fragment of PHA synthase protein may also be modified, partially deleted or partially replaced, for example by the *M. tuberculosis* or *M. bovis* antigens described herein, or by a *M. tuberculosis* or *M. bovis* antigen binding domain as contemplated herein, or another fusion partner without inactivating the enzyme or preventing covalent attachment of the synthase to the polymer particle.

In certain cases, the *M. tuberculosis* or *M. bovis* antigen(s) or the *M. tuberculosis* or *M. bovis* antigen binding domain(s) or another fusion partner are fused to the N-terminus or to the C-terminus of PHA synthase protein without inactivating the enzyme or preventing covalent attachment of the synthase to the polymer particle. Similarly, in other cases the *M. tuberculosis* or *M. bovis* antigen(s), the *M. tuberculosis* or *M. bovis* antigen binding domain(s), or other fusion partner are inserted within the PHA synthase protein, or indeed within the particle-forming protein. Examples of PhaC fusions are known in the art and presented herein.

A "polymer depolymerase" as used herein refers to a protein which is capable of hydrolysing existing polymer, such as that found in a polymer particle, into water soluble monomers and oligomers. Examples of polymer depolymerases occur in a wide variety of PHA-degrading bacteria and fungi, and include the PhaZ1-PhaZ7 extracellular depolymerases from *Paucimonas lemoignei*, the PhaZ depolymerases from *Acidovorax* sp., *A. faecalis* (strains AE122 and T1), *Delftia* (*Comamonas*) *acidovorans* strain YM1069, *Comamonas testosteroni*, *Comamonas* sp., *Leptothrix* sp. strain HS, *Pseudomonas* sp. strain GM101 (acession no. AF293347), *P. fluorescens* strain GK13, *P. stutzeri*, *R. pickettii* (strains A1 and K1, acession no. JO4223, D25315), *S. exfoliatus* K10 and *Streptomyces hygroscopicus* (see Jendrossek D., and Handrick, R., *Microbial Degredation of Polyhydroxyalkanoates*, Annual Review of Microbiology, 2002, 56:403-32).

The term "polypeptide", as used herein, encompasses amino acid chains of any length but preferably at least 5 amino acids, including full-length proteins, in which amino acid residues are linked by covalent peptide bonds. Polypeptides of the present invention are purified natural products, or are produced partially or wholly using recombinant or synthetic techniques. The term may refer to a polypeptide, an aggregate of a polypeptide such as a dimer or other multimer, a fusion polypeptide, a polypeptide variant, or derivative thereof.

The term "promoter" refers to non transcribed cis-regulatory elements upstream of the coding region that regulate gene transcription. Promoters comprise cis-initiator elements which specify the transcription initiation site and conserved boxes such as the TATA box, and motifs that are bound by transcription factors.

The term "terminator" refers to sequences that terminate transcription, which are found in the 3' untranslated ends of genes downstream of the translated sequence. Terminators are important determinants of mRNA stability and in some cases have been found to have spatial regulatory functions.

The term "substance" when referred to in relation to being bound to or absorbed into or incorporated within a polymer particle is intended to mean a substance that is bound by a fusion partner or a substance that is able to be absorbed into or incorporated within a polymer particle.

The term "variant" as used herein refers to polynucleotide or polypeptide sequences different from the specifically identified sequences, wherein one or more nucleotides or amino acid residues is deleted, substituted, or added. Variants are naturally-occurring allelic variants, or non-naturally occurring variants. Variants are from the same or from other species and may encompass homologues, paralogues and orthologues. In certain embodiments, variants of the polynucleotides and polypeptides possess biological activities that are the same or similar to those of the wild type polynucleotides or polypeptides. The term "variant" with reference to polynucleotides and polypeptides encompasses all forms of polynucleotides and polypeptides as defined herein.

Polynucleotide and Polypeptide Variants

The term "polynucleotide(s)," as used herein, means a single or double-stranded deoxyribonucleotide or ribonucleotide polymer of any length but preferably at least 15 nucleotides, and include as non-limiting examples, coding and non-coding sequences of a gene, sense and antisense sequences complements, exons, introns, genomic DNA, cDNA, pre-mRNA, mRNA, rRNA, siRNA, miRNA, tRNA, ribozymes, recombinant polypeptides, isolated and purified naturally occurring DNA or RNA sequences, synthetic RNA and DNA sequences, nucleic acid probes, primers and fragments. A number of nucleic acid analogues are well known in the art and are also contemplated.

A "fragment" of a polynucleotide sequence provided herein is a subsequence of contiguous nucleotides that is preferably at least 15 nucleotides in length. The fragments of the invention preferably comprises at least 20 nucleotides, more preferably at least 30 nucleotides, more preferably at least 40 nucleotides, more preferably at least 50 nucleotides and most preferably at least 60 contiguous nucleotides of a polynucleotide of the invention. A fragment of a polynucleotide sequence can be used in antisense, gene silencing, triple helix or ribozyme technology, or as a primer, a probe, included in a microarray, or used in polynucleotide-based selection methods.

The term "fragment" in relation to promoter polynucleotide sequences is intended to include sequences comprising cis-elements and regions of the promoter polynucleotide sequence capable of regulating expression of a polynucleotide sequence to which the fragment is operably linked.

Preferably fragments of promoter polynucleotide sequences of the invention comprise at least 20, more preferably at least 30, more preferably at least 40, more preferably at least 50, more preferably at least 100, more preferably at least 200, more preferably at least 300, more preferably at least 400, more preferably at least 500, more preferably at least 600, more preferably at least 700, more preferably at least 800, more preferably at least 900 and most preferably at least 1000 contiguous nucleotides of a promoter polynucleotide of the invention.

The term "primer" refers to a short polynucleotide, usually having a free 3'OH group, that is hybridized to a template and used for priming polymerization of a polynucleotide complementary to the template. Such a primer is preferably at least 5, more preferably at least 6, more preferably at least 7, more preferably at least 9, more preferably at least 10, more preferably at least 11, more preferably at least 12, more preferably at least 13, more preferably at least 14, more preferably at least 15, more preferably at least 16, more preferably at least 17, more preferably at least 18, more preferably at least 19, more preferably at least 20 nucleotides in length.

The term "probe" refers to a short polynucleotide that is used to detect a polynucleotide sequence that is complementary to the probe, in a hybridization-based assay. The probe may consist of a "fragment" of a polynucleotide as defined herein. Preferably such a probe is at least 5, more preferably at least 10, more preferably at least 20, more preferably at least 30, more preferably at least 40, more preferably at least 50, more preferably at least 100, more preferably at least 200, more preferably at least 300, more preferably at least 400 and most preferably at least 500 nucleotides in length.

The term "variant" as used herein refers to polynucleotide or polypeptide sequences different from the specifically identified sequences, wherein one or more nucleotides or amino acid residues is deleted, substituted, or added. Variants are naturally-occurring allelic variants, or non-naturally occurring variants. Variants are from the same or from other species and may encompass homologues, paralogues and orthologues. In certain embodiments, variants of the polynucleotides and polypeptides possess biological activities that are the same or similar to those of the wild type polynucleotides or polypeptides. The term "variant" with reference to polynucleotides and polypeptides encompasses all forms of polynucleotides and polypeptides as defined herein.

Polynucleotide Variants

Variant polynucleotide sequences preferably exhibit at least 50%, more preferably at least 51%, at least 52%, at least 53%, at least 54%, at least 55%, at least 56%, at least 57%, at least 58%, at least 59%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least %, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identity to a specified polynucleotide sequence. Identity is found over a comparison window of at least 20 nucleotide positions, preferably at least 50 nucleotide positions, at least 100 nucleotide positions, or over the entire length of the specified polynucleotide sequence.

Polynucleotide sequence identity can be determined in the following manner. The subject polynucleotide sequence is compared to a candidate polynucleotide sequence using BLASTN (from the BLAST suite of programs, version 2.2.10 [October 2004]) in bl2seq (Tatiana A. Tatusova, Thomas L. Madden (1999), "Blast 2 sequences—a new tool for comparing protein and nucleotide sequences", FEMS Microbiol Lett. 174:247-250), which is publicly available from NCBI (ftp://ftp.ncbi.nih.gov/blast/). The default parameters of bl2seq are utilized except that filtering of low complexity parts should be turned off.

The identity of polynucleotide sequences can be examined using the following unix command line parameters:

bl2seq -i nucleotideseq1 -j nucleotideseq2 -F F -p blastn

The parameter -F F turns off filtering of low complexity sections. The parameter -p selects the appropriate algorithm for the pair of sequences. The bl2seq program reports sequence identity as both the number and percentage of identical nucleotides in a line "Identities=".

Polynucleotide sequence identity may also be calculated over the entire length of the overlap between a candidate and subject polynucleotide sequences using global sequence alignment programs (e.g. Needleman, S. B. and Wunsch, C. D. (1970) J. Mol. Biol. 48, 443-453). A full implementation of the Needleman-Wunsch global alignment algorithm is found in the needle program in the EMBOSS package (Rice, P. Longden, I. and Bleasby, A. EMBOSS: The European Molecular Biology Open Software Suite, Trends in Genetics June 2000, vol 16, No 6. pp. 276-277) which can be obtained from http://www.hgmp.mrc.ac.uk/Software/EMBOSS/. The European Bioinformatics Institute server also provides the facility to perform EMBOSS-needle global alignments between two sequences on line at http:/www.ebi.ac.uk/emboss/align/.

Alternatively the GAP program can be used which computes an optimal global alignment of two sequences without penalizing terminal gaps. GAP is described in the following paper: Huang, X. (1994) On Global Sequence Alignment. Computer Applications in the Biosciences 10, 227-235.

Polynucleotide variants of the present invention also encompass those which exhibit a similarity to one or more of the specifically identified sequences that is likely to preserve the functional equivalence of those sequences and which could not reasonably be expected to have occurred by random chance. Such sequence similarity with respect to polypeptides determined using the publicly available bl2seq program from the BLAST suite of programs (version 2.2.10 [October 2004]) from NCBI (ftp://ftp.ncbi.nih.gov/blast/).

The similarity of polynucleotide sequences can be examined using the following unix command line parameters:

bl2seq -i nucleotideseq1 -j nucleotideseq2 F F -p TBlastx

The parameter -F F turns off filtering of low complexity sections. The parameter -p selects the appropriate algorithm for the pair of sequences. This program finds regions of similarity between the sequences and for each such region reports an "E value" which is the expected number of times one could expect to see such a match by chance in a database of a fixed reference size containing random sequences. The size of this database is set by default in the bl2seq program. For small E values, much less than one, the E value is approximately the probability of such a random match.

Variant polynucleotide sequences preferably exhibit an E value of less than $1\times10-10$, more preferably less than $1\times10-20$, less than $1\times10-30$, less than $1\times10-40$, less than $1\times10-50$, less than $1\times10-60$, less than $1\times10-70$, less than $1\times10-80$, less than $1\times10-90$, less than $1\times10-100$, less than $1\times10-110$, less than $1\times10-120$ or less than $1\times10-123$ when compared with any one of the specifically identified sequences.

Alternatively, variant polynucleotides of the present invention hybridize to a specified polynucleotide sequence, or complements thereof under stringent conditions.

The term "hybridize under stringent conditions", and grammatical equivalents thereof, refers to the ability of a polynucleotide molecule to hybridize to a target polynucleotide molecule (such as a target polynucleotide molecule immobilized on a DNA or RNA blot, such as a Southern blot or Northern blot) under defined conditions of temperature and salt concentration. The ability to hybridize under stringent hybridization conditions can be determined by initially hybridizing under less stringent conditions then increasing the stringency to the desired stringency.

With respect to polynucleotide molecules greater than about 100 bases in length, typical stringent hybridization conditions are no more than 25 to 30° C. (for example, 10° C.) below the melting temperature (Tm) of the native duplex (see generally, Sambrook et al., Eds, 1987, Molecular Cloning, A Laboratory Manual, 2nd Ed. Cold Spring Harbor Press; Ausubel et al., 1987, Current Protocols in Molecular Biology, Greene Publishing). Tm for polynucleotide molecules greater than about 100 bases can be calculated by the formula Tm=81.5+0.41% (G+C-log (Na+). (Sambrook et al., Eds, 1987, Molecular Cloning, A Laboratory Manual, 2nd Ed. Cold Spring Harbor Press; Bolton and McCarthy, 1962, PNAS 84:1390). Typical stringent conditions for polynucleotide of greater than 100 bases in length would be hybridization conditions such as prewashing in a solution of 6×SSC, 0.2% SDS; hybridizing at 65° C., 6×SSC, 0.2% SDS overnight; followed by two washes of 30 minutes each in 1×SSC, 0.1% SDS at 65° C. and two washes of 30 minutes each in 0.2×SSC, 0.1% SDS at 65° C.

With respect to polynucleotide molecules having a length less than 100 bases, exemplary stringent hybridization conditions are 5 to 10° C. below Tm. On average, the Tm of a polynucleotide molecule of length less than 100 bp is reduced by approximately (500/oligonucleotide length)° C.

With respect to the DNA mimics known as peptide nucleic acids (PNAs) (Nielsen et al., Science. 1991 Dec. 6; 254(5037):1497-500) Tm values are higher than those for DNA-DNA or DNA-RNA hybrids, and can be calculated using the formula described in Giesen et al., Nucleic Acids Res. 1998 Nov. 1; 26(21):5004-6. Exemplary stringent hybridization conditions for a DNA-PNA hybrid having a length less than 100 bases are 5 to 10° C. below the Tm.

Variant polynucleotides of the present invention also encompasses polynucleotides that differ from the sequences of the invention but that, as a consequence of the degeneracy of the genetic code, encode a polypeptide having similar activity to a polypeptide encoded by a polynucleotide of the present invention. A sequence alteration that does not change the amino acid sequence of the polypeptide is a "silent variation". Except for ATG (methionine) and TGG (tryptophan), in some examples other codons for the same amino acid are changed by art recognized techniques, e.g., to optimize codon expression in a particular host organism.

Polynucleotide sequence alterations resulting in conservative substitutions of one or several amino acids in the encoded polypeptide sequence without significantly altering its biological activity are also included in the invention. A skilled artisan will be aware of methods for making phenotypically silent amino acid substitutions (see, e.g., Bowie et al., 1990, Science 247, 1306).

Variant polynucleotides due to silent variations and conservative substitutions in the encoded polypeptide sequence can be determined using the publicly available bl2seq program from the BLAST suite of programs (version 2.2.10 [October 2004]) from NCBI (ftp://ftp.ncbi.nih.gov/blast/) via the TBlastx algorithm as previously described.

Polypeptide Variants

The term "variant" with reference to polypeptides encompasses naturally occurring, recombinantly and synthetically produced polypeptides. Variant polypeptide sequences preferably exhibit at least 50%, more preferably at least 51%, at least 52%, at least 53%, at least 54%, at least 55%, at least 56%, at least 57%, at least 58%, at least 59%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least %, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identity to a sequences of the present invention. Identity is found over a comparison window of at least 20 amino acid positions, preferably at least 50 amino acid positions, at least 100 amino acid positions, or over the entire length of a polypeptide of the invention.

Polypeptide sequence identity can be determined in the following manner. The subject polypeptide sequence is compared to a candidate polypeptide sequence using BLASTP (from the BLAST suite of programs, version 2.2.10 [October 2004]) in bl2seq, which is publicly available from NCBI (ftp://ftp.ncbi.nih.gov/blast/). The default parameters of bl2seq are utilized except that filtering of low complexity regions should be turned off.

Polypeptide sequence identity may also be calculated over the entire length of the overlap between a candidate and subject polynucleotide sequences using global sequence alignment programs. EMBOSS-needle (available at http://www.ebi.ac.uk/emboss/align/) and GAP (Huang, X. (1994) On Global Sequence Alignment. Computer Applications in the Biosciences 10, 227-235.) as discussed above are also suitable global sequence alignment programs for calculating polypeptide sequence identity.

Polypeptide variants of the present invention also encompass those which exhibit a similarity to one or more of the specifically identified sequences that is likely to preserve the functional equivalence of those sequences and which could not reasonably be expected to have occurred by random chance. Such sequence similarity with respect to polypeptides can be determined using the publicly available bl2seq program from the BLAST suite of programs (version 2.2.10 [October 2004]) from NCBI (ftp://ftp.ncbi.nih.gov/blast/). The similarity of polypeptide sequences can be examined using the following unix command line parameters:

bl2seq -i peptideseq1 -j peptideseq2 -F F -p blastp

Variant polypeptide sequences preferably exhibit an E value of less than $1\times10^{-10}$, more preferably less than $1\times10^{-20}$, less than $1\times10^{-30}$, less than $1\times10^{-40}$, less than $1\times10^{-50}$, less than $1\times10^{-60}$, less than $1\times10^{-70}$, less than $1\times10^{-80}$, less than $1\times10^{-90}$, less than $1\times10^{-100}$, less than $1\times10^{-110}$, less than $1\times10^{-120}$ or less than $1\times10^{-123}$ when compared with any one of the specifically identified sequences.

The parameter -F F turns off filtering of low complexity sections. The parameter -p selects the appropriate algorithm for the pair of sequences. This program finds regions of similarity between the sequences and for each such region reports an "E value" which is the expected number of times one could expect to see such a match by chance in a database of a fixed reference size containing random sequences. For small E values, much less than one, this is approximately the probability of such a random match.

Conservative substitutions of one or several amino acids of a described polypeptide sequence without significantly altering its biological activity are also included in the invention. A skilled artisan will be aware of methods for making phenotypically silent amino acid substitutions (see, e.g., Bowie et al., 1990, Science 247, 1306).

A polypeptide variant of the present invention also encompasses that which is produced from the nucleic acid encoding a polypeptide, but differs from the wild type polypeptide in that it is processed differently such that it has an altered amino acid sequence. For example, a variant is produced by an alternative splicing pattern of the primary RNA transcript to that which produces a wild type polypeptide.

The term "vector" refers to a polynucleotide molecule, usually double stranded DNA, which is used to transport the genetic construct into a host cell. In certain examples the vector is capable of replication in at least one additional host system, such as *E. coli*.

2. Tuberculosis

It will be appreciated that the polymer particles, methods and compositions of the present invention are in part directed to the identification, prevention or treatment of *tuberculosis*.

*Tuberculosis* is a severe global health concern, resulting in over 2 million human deaths worldwide per year. The disease in human subjects is caused by the bacterium *M. tuberculosis*. The bacterium commonly invades the lungs, through inhalation, causing infection in the lung, which can ultimately spread to other parts of the body, including the central nervous system, the lymphatic system, the circulatory system, the genitourinary system, the gastrointestinal systems, bones, joints and the skin (Dietrich, 2006; Mustafa, 2001). Various forms of *tuberculosis* in agricultural animals, such as bovine *tuberculosis* (typically caused by *M. bovis*) and Johne's disease (typically caused by *M. paratuberculosis*), also have a significant negative effect on production. *Mycobacterium* is a genus of Actinobacteria. The genus includes pathogens known to cause serious diseases in mammals, including *tuberculosis* and leprosy. Examples of pathogen species include *M. tuberculosis*, *M. bovis*, *M. africanum*, *M. microti*; *M. leprae* (leprosy), *M. avium paratuberculosis* (associated with Crohn's disease in humans and Johne's disease in sheep).

The spread of infection by *M. tuberculosis* or *M. bovis* is limited by the immune system. Many individuals show few symptoms other than a cough and fever. However, approximately 30% of individuals are not able to sufficiently control the infection and develop a primary disease. Despite this, the disease is capable of sitting dormant in individuals, infecting them again years or even decades later. For this reason, *M. tuberculosis* and *M. bovis* is unusual among infectious bacteria, as they can evade the immune response and survive in a refractory non- or slow-replicating phase for long periods of time.

*Tuberculosis* infection expresses itself in three phases. The first acute stage is identified by a proliferation of bacteria in the body's organs. An immune response quickly follows, controlling the infection and eventually resulting in a decline in bacterial load. Following the acute phase, the second latent phase is established. During this second stage, bacterial load is maintained at a stable and low level. *M. tuberculosis* or *M. bovis* change from an active multiplication state in the acute phase to a dormant state in the latent phase. A third reactivation phase may occur whereby the bacteria begin replicating again. The factors that influence this third stage are still largely unknown (Barnes and Cave, 2003).

It it thought that changes in antigen specificity of the immune response occur throughout the different stages of infection, as the bacterium is capable of modulating gene expression during transition from active replication to dormancy.

2.1 Current Treatment Strategies

Current treatment strategies for protection against *tuberculosis* include specific vaccines against known antigens, or antibiotic treatment in patients infected with intracellular bacterial pathogens.

The lack of suitable vaccines for protecting against reactivation of intracellular pathogens, either prophylactically prior to infection, or therapeutically after onset of infection, has prompted the need for new and improved treatment strategies against intracellular pathogens.

For example, the only currently available vaccine for *tuberculosis* is Bacille Calmette-Geurin (BCG), which contains live attenuated strains of *Mycobacterium bovis*. The efficacy of BCG in controlling *tuberculosis* infection is limited. Although the vaccine appears to protect children against the primary disease, its protective efficacy against the adult form of the disease (reactivation after latency) is reduced (World Health Organisation—http://www.who.int). It has also been reported that efficacy of BCG is limited in many Third World countries where *tuberculosis* is prevalent. In addition, as the BCG vaccine is a live vaccine it is not suitable for administration to patients who are immunocomprosmised. While the BCG vaccine reportedly reduces dissemination of *M. tuberculosis* to the spleen (and other organs), it does not prevent bacterial growth in the lungs.

The lack of a suitable vaccine for protecting against reactivation, either prophylactically prior to infection, or therapeutically after onset of infection, together with the other problems associated with live vaccines, has prompted the need for new and improved diagnosis and treatment strategies against *tuberculosis*.

3. Immune Response

3.1. Cell-Mediated Response

Cell-mediated immunity is primarily mediated by T-lymphocytes. Pathogenic antigens are expressed on the surface of antigen presenting cells (such as macrophages, B-lymphocytes, and dendritic cells), bound to either major histocompatibility MHC Class I or MHC Class II molecules. Presentation of pathogenic antigen coupled to MHC Class II activates a helper (CD4+) T-cell response. Upon binding of the T-cell to the antigen-MHC II complex, CD4+ T-cells proliferate, releasing cytokines, including interferon-gamma (IFN-γ) and interleukin 2 (IL-2), IL-4, IL-7, and IL-12.

Presentation of pathogenic antigens bound to MHC Class I molecules activates a cytotoxic (CD8+) T-cell response. Upon binding of the T-cell to the antigen-MHC I complex, CD8+ cells secrete perforin, resulting in pathogen cell lysis, swelling and death. Alternatively, CD8+ cells induce programmed cell death or apoptosis. Activation of CD8+ T-cells is amplified by the release of specific cytokines by CD4+ T-cells.

A cell-mediated immune response is believed to be central to the immunity against various pathogens, including intracellular pathogens such as *M. tuberculosis*.

Methods to assess and monitor the onset or progression of a cell-mediated response in a subject are well known in the art. Convenient exemplary methods include those in which the presence of or the level of one or more cytokines associated with a cell-mediated response, such as those identified herein, including for example interferon-gamma, is assessed. Similarly, cell-based methods to assess or monitor the onset and progression of a cell-mediated response are amenable to use in the present invention, and may include cell proliferation or activation assays, including assays targeted at identifying activation or expansion of one or more populations of immune cells, such as T-lymphocytes.

In certain embodiments, methods of the invention that elicit both a cell-mediated immune response and a humoral response are preferred.

In other embodiments, methods of the invention that elicit predominantly a cell-mediated response are preferred. Such methods may include those that elicit a cell-mediated immune response without a significant humoral response, or without any detectable humoral response. In one example, the immune response is a cell-mediated immune response, such as that indicated by an IFN-γ response, in the absence of a significant IgA response, or in the absence of a significant IgE response, or in the absence of a significant IgG response, including the absence of a significant IgG1 response, or the absence of a significant IgG2 response, or in the absence of a significant IgM response.

3.2. Humoral Response

The humoral immune response is mediated by secreted antibodies produced by B cells. The secreted antibodies bind to antigens presented on the surface of invading pathogens, flagging them for distruction.

It has been suggested that a combined cell-mediated and humoral response (such as that as a consequence of an initiated cell-mediated response) would be beneficial to achieve a more highly sensitive immune response to or enhance the level of protection against intracellular pathogens.

Again, methods to assess and monitor the onset or progression of a humoral response are well known in the art. These include antibody binding assays, ELISA, skin-prick tests and the like.

4. *Tuberculosis* Antigens

It will be appreciated that a great many *M. tuberculosis* and *M. bovis* antigens have been characterised. Exemplary *M. tuberculosis* and *M. bovis* antigens early secretary antigen target (ESAT) –6, Ag85A, Ag85B (MPT59), Ag85B, Ag85C, MPT32, MPT51, MPT59, MPT63, MPT64, MPT83, MPB5, MPB59, MPB64, MTC28, MTB2, MTB8.4, MTB9.9, MTB32A, MTB39, MTB41, TB10.4, TB10C, TB11B, TB12.5, TB13A, TB14, TB15, TB15A, TB16, TB16A, TB17, TB18, TB21, TB20.6, TB24, TB27B, TB32, TB32A, TB33, TB38, TB40.8, TB51, TB54, TB64, CFP6, CFP7, CFP7A, CFP7B, CFP8A, CFP8B, CFP9, CFP10, CFP11, CFP16, CFP17, CFP19, CFP19A, CFP19B, CFP20, CFP21, CFP22, CFP22A, CFP23, CFP23A, CFP23B, CFP25, CFP25A, CFP27, CFP28, CFP28B, CFP29, CFP30A, CFP30B, CFP50, CWP32, hspX (alpha-crystalline), APA, Tuberculin purified protein derivative (PPD), ST-CF, PPE68, LppX, PstS-1, PstS-2, PstS-3, HBHA, GroEL, GroEL2, GrpES, LHP, 19 kDa lipoprotein, 71 kDa, RD1-ORF2, RD1-ORF3, RD1-ORF4, RD1-ORF5, RD1-ORF8, RD1-ORF9A, RD1-ORF9B, Rv1984c, Rv0577, Rv1827, BfrB, Tpx. Rv1352, Rv1810, PpiA, Cut2, FbpB, FbpA, FbpC, DnaK, FecB, Ssb, Rp1L, FixA, FixB, AhpC2, Rv2626c, Rv1211, Mdh, Rv1626, Adk, C1pP, SucD (Belisle et al, 2005; U.S. Pat. No. 7,037,510; US 2004/0057963; US 2008/0199493; US 2008/0267990), or at least one antigenic portion or T-cell epitope of any of the above mentioned antigens.

However, the applicants have determined that a combination of the antigens selected from the group consisting of ESAT6, CFP10, Rv3615c, and Rv3020c are particularly effective in the present invention.

The amino acid sequence of the ESAT6

```
[SEQ. ID. NO. 1]
MTEQQWNFAGIEAAASAIQGNVTSIHSLLDEGKQSLTKLAAAWGGSGSEA

YQGVQQKWDATATELNNALQNLARTISEAGQAMASTEGNVTGMFA.
```

The amino acid sequence of the CFP10 antigen is as follows:

```
[SEQ. ID. NO. 2]
MAEMKTDAATLAQEAGNFERISGDLKTQIDQVESTAGSLQGQWRGAAGTA

AQAAVVRFQEAANKQKQELDEISTNIRQAGVQYSRADEEQQQALSSQMGF.
```

The amino acid sequence of the Rv3615c antigen is as follows:

```
[SEQ. ID. NO. 3]
MTENLTVQPERLGVLASHHDNAAVDASSGVEAAAGLGESVAITHGPYCSQ

FNDTLNVYLTAHNALGSSLHTAGVDLAKSLRIAAKIYSEADEAWRKAIDG

LFT.
```

The amino acid sequence of the Rv3020c antigen is as follows:

```
[SEQ. ID. NO. 4]
GGGGGMSLLDAHIPQLIASHTAFAAKAGLMRHTIGQAEQQAMSAQAFHQG

ESAAAFQGAHARFVAAAAKVNTLLDIAQANLGEAAGTYVAADAAAASSYT

GF.
```

The amino acid sequence of the Rv2346c antigen is as follows:

```
[SEQ. ID. NO. 5]
MTINYQFGDVDAHGAMIRAQAGLLEAEHQAIVRDVLAAGDFWGGAGSVAC

QEFITQLGRNFQVIYEQANAHGQKVQAAGNNMAQTDSAVGSSWA.
```

In various examples, the two or more antigens, for example three, four, or all five of the antigens selected from the group consisting of ESAT6, CFP10, Rv3615c, Rv3020c, and Rv2346c, or two or more binding domains capable of binding the specified antigens, or any combination thereof, are produced as a fusion protein, in certain embodiments additionally comprising a particle-forming polypeptide. In certain embodiments, other *M. tuberculosis* or *M. bovis* antigens, including other *M. tuberculosis* or *M. bovis* antigens selected from above mentioned antigens, may additionally be utilised.

For example, in one embodiment, the two or more antigens comprise an ESAT6-Rv3020c fusion, for example for in-frame fusion at the C-terminus of the polymer synthase, such as phaC, comprising the amino acid sequence:

[SEQ. ID. NO. 6]

EMTEQQWNFAGIEAAASAIQGNVTSIHSLLDEGKQSLTKLAAAWGGSGSE

AYQGVQQKWDATATELNNALQNLARTISEAGQAMASTEGNVTGMFAGGGG

GMSLLDAHIPQLIASHTAFAAKAGLMRHTIGQAEQQAMSAQAFHQGESAA

AFQGAHARFVAAAAKVNTLLDIAQANLGEAAGTYVAADAAAASSYTGF.

In another example, the two or more antigens comprise CFP10, Rv3615c, and ESAT6, for example as a fusion polypeptide additionally comprising a polymer synthase, such as PhaC. For example, the fusion polypeptide comprises CFP10 and Rv3615c fused to the N-terminus of PhaC, with ESAT6 fused to the C-terminus, such as a polypeptide comprising the amino acid sequence depicted herein as SEQ. ID. NO. 10.

In other embodiments, the fusion polypeptides of the invention comprise the antigen fusions as described herein in the Examples, including, for example, the fusion polypeptides comprising an amino acid sequence of any one of SEQ. ID. NO.s 7 to 10, including those encoded by the nucleotide sequences of any one of SEQ. ID. NO.s 11 to 15.

It will be appreciated that fusion polypeptides comprising two or more antigens for use in the present invention can be encoded by nucleic acid sequences suitable for expression, including those optimised for expression in different host cells. For example, the ESAT6-Rv3020c fusion polypeptide depicted herein as SEQ. ID. NO. 6 can be encoded by a nucleotide sequence optimised for expression in *E. coli*, using codon optimisation, such as the nucleotide sequence:

[SEQ. ID. NO. 11]

ctcgagatgacggaacaacaatggaactttgctggcatcgaagccgccgc atctgctattcaaggcaatgtgacctctatccactcgctgctggatgaag gcaaacagagtctgaccaaactggcagcagcatggggcggtagcggctct gaagcctatcaaggtgtgcagcaaaaatgggacgctaccgcgacggaact gaacaatgccctgcagaacctggcacgtacgatttctgaagcaggtcaag ctatggcaagcacggaaggcaatgtcacgggcatgttcgcaggcggcggc ggcggcatgagcctgctggatgcgcatattccgcagctgattgcgagcca taccgcgtttgcggcgaaagcgggcctgatgcgtcataccattggccagg cggaacagcaggcgatgagcgcgcaggcgtttcatcagggcgaaagcgcg gcggcgtttcagggcgcgcatgcgcgttttgtggcggcggcggcgaaagt gaacaccctgctggatattgcgcaggcgaacctgggcgaagcggcgggca cctatgtggcggcggatgcggcggcggcgagcagctataccggcttttaa ggatcc.

In another embodiment of nucleic acid coding sequences optimised for expression in a particular host, the CFP10-Rv3615c-PhaC-ESAT6 fusion polypeptide comprising the amino acid sequence depicted herein as SEQ. ID. NO. 10 is encoded by a nucleotide sequence optimised for expression in *E. coli*, using codon optimisation, such as the nucleotide sequence:

[SEQ. ID. NO. 15]

atggcagaaatgaaaacggatgcggcgaccctggcacaagaagcgggcaactttgaacgtattagcggcgacctgaaaacccaaatcgat caggttgaaagcaccgcgggttctctgcaaggccagtggcgtggtgcggccggtacggcagctcaagcggccgtggttcgctttcaggaa gcagctaacaaacaaaaacaggaactggatgaaatttcaaccaatatccgtcaagccggcgtgcagtattcgcgcgcagacgaagaacag -continued

```
caacaggctctgagctctcaaatgggtttcgggcccggcggtggcggtggcccgatgaccgaaaacctgacggttcagccggaacgtctg ggtgtcctggcaagtcatcacgataatgcagcagtcgacgccagttccggtgtggaagcagctgcaggtctgggtgaaagtgtggcgatt acccatggtccgtattgctcccagtttaacgataccctgaatgtttacctgacggcccataacgcactgggttcatcgctgcacacggct ggtgtcgacctggcaaaatctctgcgcatcgccgcaaaaatctattcagaagcagacgaagcgtggcgtaaagcaatcgacggcctgttc accactagtgcgaccggcaaaggcgcggcagcttccacgcaggaaggcaagtcccaaccattcaaggtcacgccggggccattcgatcca gccacatggctggaatggtcccgccagtggcagggcactgaaggcaacggccacgcggccgcgtccggcattccgggcctggatgcgctg gcaggcgtcaagatcgcgccggcgcagctgggtgatatccagcagcgctacatgaaggacttctcagcgctgtggcaggccatggccgag ggcaaggccgaggccaccggtccgctgcacgaccggcgcttcgccggcgacgcatggcgcaccaacctcccatatcgcttcgctgccgcg ttctacctgctcaatgcgcgcgccttgaccgagctggccgatgccgtcgaggccgatgccaagaccccgccagcgcatccgcttcgcgatc tcgcaatgggtcgatgcgatgtcgcccgccaacttccttgccaccaatcccgaggcgcagcgcctgctgatcgagtcgggcggcgaatcg ctgcgtgccggcgtgcgcaacatgatggaagacctgacacgcggcaagatctcgcagaccgacgagagcgcgtttgaggtcggccgcaat gtcgcggtgaccgaaggcgccgtggtcttcgagaacgagtacttccagctgttgcagtacaagccgctgaccgacaaggtgcacgcgcgc ccgctgctgatggtgccgccgtgcatcaacaagtactacatcctggacctgcagccggagagctcgctggtgcgccatgtggtggagcag ggacatacggtgtttctggtgtcgtggcgcaatccggacgccagcatggccggcagcacctgggacgactacatcgagcacgcggccatc cgcgccatcgaagtcgcgcgcgacatcagcggccaggacaagatcaacgtgctcggcttctgcgtgggcggcaccattgtctcgaccgcg ctggcggtgctggccgcgcgcggcgagcacccggccgccagcgtcacgctgctgaccacgctgctggactttgccgacacgggcatcctc gacgtctttgtcgacgagggccatgtgcagttgcgcgaggccacgctgggcggcggcgccggcgcgccgtgcgcgctgctgcgcggcctt gagctggccaataccttctcgttcttgcgcccgaacgacctggtgtggaactacgtggtcgacaactacctgaagggcaacacgccggtg ccgttcgacctgctgttctggaacggcgacgccaccaacctgccggggccgtggtactgctggtacctgcgccacacctacctgcagaac gagctcaaggtaccgggcaagctgaccgtgtgcggcgtgccggtggacctggccagcatcgacgtgccgacctatatctacggctcgcgc gaagaccatatcgtgccgtggaccgcggcctatgcctcgaccgcgctgctggcgaacaagctgcgcttcgtgctgggtgcgtcgggccat atcgccggtgtgatcaacccgccggccaagaacaagcgcagccactggactaacgatgcgctgccggagtcgccgcagcaatggctggcc ggcgccatcgagcatcacggcagctggtggccggactggaccgcatggctggccgggcaggccggcgcgaaacgcgccgcgcccgccaac tatggcaatgcgcgctatcgcgcaatcgaacccgcgcctgggcgatacgtcaaagccaaggcacatatggtgctggcggtggcgattgat aaacgcggaggcggtggaggcctcgagatgacggaacaacaatggaactttgctggcatcgaagccgccgcatctgctattcaaggcaat gtgacctctatccactcgctgctggatgaaggcaaacagagtctgaccaaactggcagcagcatggggcggtagcggctctgaagcctat caaggtgtgcagcaaaaatgggacgctaccgcgacggaactgaacaatgccctgcagaacctggcacgtacgatttctgaagcaggtcaa gctatggcaagcacggaaggcaatgtcacgggcatgttcgcataa.
```

In other embodiments, the fusion polypeptides of the invention include those encoded by the nucleotide sequences of any one of SEQ. ID. NO.s 11 to 15.

5. Expression Constructs

Processes for producing and using expression constructs for expression of fusion polypeptides in microorganisms, plant cells or animal cells (cellular expression systems) or in cell free expression systems, and host cells comprising expression constructs useful for forming polymer particles for use in the invention are well known in the art (e.g. Sambrook et al., 1987; Ausubel et al., 1987).

Expression constructs for use in methods of the invention are in one embodiment inserted into a replicable vector for cloning or for expression, or in another embodiment are incorporated into the host genome. Various vectors are publicly available. The vector is, for example, in the form of a plasmid, cosmid, viral particle, or phage. The appropriate nucleic acid sequence can be inserted into the vector by a variety of procedures. In general, DNA is inserted into an appropriate restriction endonuclease site(s) using techniques known in the art. Vector components generally include, but are not limited to, one or more of a signal sequence, an origin of replication, one or more selectable marker genes, an enhancer element, a promoter, and a transcription termination sequence. Construction of suitable vectors containing one or more of these components employs standard ligation techniques known in the art.

Both expression and cloning vectors contain a nucleic acid sequence that enables the vector to replicate in one or more selected host cells. Such sequences are well known for a variety of bacteria, yeast, and viruses.

In one embodiment the expression construct is present on a high copy number vector.

In one embodiment the high copy number vector is selected from those that are present at 20 to 3000 copies per host cell.

In one embodiment the high copy number vector contain a high copy number origin of replication (ori), such as ColE1 or a ColE1-derived origin of replication. For example, the ColE-1 derived origin of replication may comprise the pUC19 origin of replication.

Numerous high copy number origins of replication suitable for use in the vectors of the present invention are known to those skilled in the art. These include the ColE1-derived origin of replication from pBR322 and its derivatives as well as other high copy number origins of replication, such as M13 FR on or p15A ori. The 2μ plasmid origin is suitable for yeast, and various viral origins (SV40, polyoma, adenovirus, VSV or BPV) are useful for cloning vectors in mammalian cells.

Preferably, the high copy number origin of replication comprises the ColE1-derived pUC19 origin of replication.

The restriction site is positioned in the origin of replication such that cloning of an insert into the restriction site will inactivate the origin, rendering it incapable of directing replication of the vector. Alternatively, the at least one restriction site is positioned within the origin such that cloning of an insert into the restriction site will render it capable of supporting only low or single copy number replication of the vector.

Expression and cloning vectors will typically contain a selection gene, also termed a selectable marker to detect the presence of the vector in the transformed host cell. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

Selectable markers commonly used in plant transformation include the neomycin phophotransferase II gene (NPT II) which confers kanamycin resistance, the aadA gene, which confers spectinomycin and streptomycin resistance, the phosphinothricin acetyl transferase (bar gene) for Ignite (AgrEvo) and Basta (Hoechst) resistance, and the hygromycin phosphotransferase gene (hpt) for hygromycin resistance.

Examples of suitable selectable markers for mammalian cells are those that enable the identification of cells competent to take up expression constructs, such as DHFR or thymidine kinase. An appropriate host cell when wild-type DHFR is employed is the CHO cell line deficient in DHFR activity, prepared and propagated as described by Urlaub et al., 1980. A suitable selection gene for use in yeast is the trp1 gene present in the yeast plasmid YRp7 (Stinchcomb et al., 1979; Kingsman et al., 1979; Tschemper et al., 1980). The trp1 gene provides a selection marker for a mutant strain of yeast lacking the ability to grow in tryptophan, for example, ATCC No. 44076 or PEP4-1 [Jones, Genetics, 85:12 (1977)].

An expression construct useful for forming polymer particles preferably includes a promoter which controls expression of at least one nucleic acid encoding a polymer synthase, particle-forming protein or fusion polypeptide.

Promoters recognized by a variety of potential host cells are well known. Promoters suitable for use with prokaryotic hosts include the β-lactamase and lactose promoter systems [Chang et al., 1978; Goeddel et al., 1979), alkaline phosphatase, a tryptophan (trp) promoter system [Goeddel, Nucleic Acids Res., 8:4057 (1980); EP 36,776], and hybrid promoters such as the tac promoter [deBoer et al., 1983). Promoters for use in bacterial systems also will contain a Shine-Dalgarno (S.D.) sequence operably linked to the nucleic acid encoding a polymer synthase, particle-forming protein or fusion polypeptide.

Examples of suitable promoting sequences for use with yeast hosts include the promoters for 3-phosphoglycerate kinase [Hitzeman et al., 1980) or other glycolytic enzymes [Hess et al., 1968; Holland, 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization.

Examples of suitable promoters for use in plant host cells, including tissue or organ of a monocot or dicot plant include cell-, tissue- and organ-specific promoters, cell cycle specific promoters, temporal promoters, inducible promoters, constitutive promoters that are active in most plant tissues, and recombinant promoters. Choice of promoter will depend upon the temporal and spatial expression of the cloned polynucleotide, so desired. The promoters are those from the host cell, or promoters which are derived from genes of other plants, viruses, and plant pathogenic bacteria and fungi. Those skilled in the art will, without undue experimentation, be able to select promoters that are suitable for use in modifying and modulating expression constructs using genetic constructs comprising the polynucleotide sequences of the invention. Examples of constitutive plant promoters include the CaMV 35S promoter, the nopaline synthase promoter and the octopine synthase promoter, and the Ubi 1 promoter from maize. Plant promoters which are active in specific tissues, respond to internal developmental signals or external abiotic or biotic stresses are described in the scientific literature. Exemplary promoters are described, e.g., in WO 02/00894, which is herein incorporated by reference.

Examples of suitable promoters for use in mammalian host cells comprise those obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, and from heat-shock promoters, provided such promoters are compatible with the host cell systems.

Transcription of an expression construct by higher eukaryotes is in some examples increased by inserting an enhancer sequence into the vector. Enhancers are cis-acting elements of DNA, usually about from 10 to 300 bp that act on a promoter to increase its transcription. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. Typically, the enhancer is spliced into the vector at a position 5' or 3' to the polymer synthase, particle-forming protein or fusion polypeptide coding sequence, but is preferably located at a site 5' from the promoter.

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding the polymer synthase, particle-forming protein or fusion polypeptide.

In one embodiment the expression construct comprises an upstream inducible promoter, such as a BAD promoter, which is induced by arabinose.

In one embodiment the expression construct comprises a constitutive or regulatable promoter system.

In one embodiment the regulatable promoter system is an inducible or repressible promoter system.

While it is desirable to use strong promoters in the production of recombinant proteins, regulation of these promoters is essential since constitutive overproduction of heterologous proteins leads to decreases in growth rate, plasmid stability and culture viability.

A number of promoters are regulated by the interaction of a repressor protein with the operator (a region downstream from the promoter). The most well known operators are those from the lac operon and from bacteriophage A. An overview of regulated promoters in $E.$ $coli$ is provided in Table 1 of Friehs & Reardon, 1991.

A major difference between standard bacterial cultivations and those involving recombinant $E.$ $coli$ is the separation of the growth and production or induction phases. Recombinant protein production often takes advantage of regulated promoters to achieve high cell densities in the growth phase (when the promoter is "off" and the metabolic burden on the host cell is slight) and then high rates of heterologous protein production in the induction phase (following induction to turn the promoter "on").

In one embodiment the regulatable promoter system is selected from LacI, Trp, phage γ and phage RNA polymerase.

In one embodiment the promoter system is selected from the lac or Ptac promoter and the lad repressor, or the trp promoter and the TrpR repressor.

In one embodiment the LacI repressor is inactivated by addition of isopropyl-β-D-thiogalactopyranoside (IPTG) which binds to the active repressor causes dissociation from the operator, allowing expression.

In one embodiment the trp promoter system uses a synthetic media with a defined tryptophan concentration, such that when the concentration falls below a threshold level the system becomes self-inducible. In one embodiment 3-β-indole-acrylic acid is added to inactivate the TrpR repressor.

In one embodiment the promoter system may make use of the bacteriophage γ repressor cI. This repressor makes use of the γ prophage and prevent expression of all the lytic genes by interacting with two operators termed OL and OR. These operators overlap with two strong promoters PL and PR respectively. In the presence of the cI repressor, binding of RNA polymerase is prevented. The cI repressor can be inactivated by UV-irradiation or treatment of the cells with mitomycin C. A more convenient way to allow expression of the recombinant polypeptide is the application of a temperature-sensitive version of the cI repressor cI857. Host cells carrying a γ-based expression system can be grown to mid-exponential phase at low temperature and then transferred to high temperature to induce expression of the recombinant polypeptide.

A widely used expression system makes use of the phage T7 RNA polymerase which recognises only promoters found on the T7 DNA, and not promoters present on the host cell chromosome. Therefore, the expression construct may contain one of the T7 promoters (normally the promoter present in front of gene 10) to which the recombinant gene will be fused. The gene coding for the T7 RNA polymerase is either present on the expression construct, on a second compatible expression construct or integrated into the host cell chromosome. In all three cases, the gene is fused to an inducible promoter allowing its transcription and translation during the expression phase.

The $E.$ $coli$ strains BL21 (DE3) and BL21 (DE3) pLysS (Invitrogen, CA) are examples of host cells carrying the T7 RNA polymerase gene (there are a few more very suitable and commercially available $E.$ $coli$ strains harbouring the T7RNA polymerase gene such as e.g. KRX and XJ (autolysing)). Other cell strains carrying the T7 RNA polymerase gene are known in the art, such as $Pseudomonas$ $aeruginosa$ ADD1976 harboring the T7 RNA polymerase gene integrated into the genome (Brunschwig & Darzins, 1992) and $Cupriavidus$ $necator$ (formerly $Ralstonia$ $eutropha$) harboring the T7 RNA polymerase gene integrated into the genome under phaP promoter control (Barnard et al., 2004).

The T7 RNA polymerase offers three advantages over the host cell enzymes: First, it consists of only one subunit, second it exerts a higher processivity, and third it is insensitive towards rifampicin. The latter characteristic can be used especially to enhance the amount of fusion polypeptide by adding this antibiotic about 10 min after induction of the gene coding for the T7 RNA polymerase. During that time, enough polymerase has been synthesised to allow high-level expression of the fusion polypeptide, and inhibition of the host cell enzymes prevents further expression of all the other genes present on both the plasmid and the chromosome. Other antibiotics which inhibit the bacterial RNA polymerase but not the T7 RNA polymerase are known in the art, such as streptolydigin and streptovaricin.

Since all promoter systems are leaky, low-level expression of the gene coding for T7 RNA polymerase may be deleterious to the cell in those cases where the recombinant polypeptide encodes a toxic protein. These polymerase molecules present during the growth phase can be inhibited by expressing the T7-encoded gene for lysozyme. This enzyme is a bifunctional protein that cuts a bond in the cell wall of the host cell and selectively inhibits the T7 RNA polymerase by binding to it, a feed-back mechanism that ensures a controlled burst of transcription during T7 infection. The $E.$ $coli$ strain BL21 (DE3) pLysS is an example of a host cell that carries the plasmid pLysS that constitutively expresses T7 lysozyme.

In one embodiment the promoter system makes use of promoters such as API or APR which are induced or "switched on" to initiate the induction cycle by a temperature shift, such as by elevating the temperature from about 30-37° C. to 42° C. to initiate the induction cycle.

A strong promoter may enhance fusion polypeptide density at the surface of the particle during in-vivo production.

Exemplary fusion polypeptides comprise:
a polymer synthase, and any two or more of the following
(i) an ESAT6 antigen,
(ii) a binding domain capable of binding an ESAT6 antigen,
(iii) a CFP10 antigen,
(iv) a binding domain capable of binding a CFP10 antigen,
(v) an Rv3615c antigen, (vi) a binding domain capable of binding an Rv3615c antigen
(vii) an Rv3020c antigen,
(viii) a binding domain capable of binding an Rv3020c antigen.
Other exemplary fusion polypeptides comprise:
a polymer synthase, and any two or more of the following
(ix) an ESAT6 antigen,
(x) a binding domain capable of binding an ESAT6 antigen,
(xi) a CFP10 antigen,
(xii) a binding domain capable of binding a CFP10 antigen,
(xiii) an Rv3615c antigen,
(xiv) a binding domain capable of binding an Rv3615c antigen
(xv) an Rv3020c antigen,
(xvi) a binding domain capable of binding an Rv3020c antigen, and
(xvii) an Rv2346c antigen
(xviii) a binding domain capable of binding an Rv2346c antigen.

Once expressed, the fusion polypeptide is able to form or facilitate formation of a polymer particle.

In one embodiment the nucleic acid sequence encoding at least polymer synthase is indirectly fused with the other nucleic acid sequences through a polynucleotide linker or spacer sequence of a desired length.

In one embodiment the amino acid sequence of the fusion polypeptide comprising the antigen(s) or binding domain(s) is contiguous with the C-terminus of the amino acid sequence comprising a polymer synthase.

In one embodiment the amino acid sequence of the fusion protein comprising the antigen(s) or binding domain(s) is indirectly fused with the N-terminus of the amino acid sequence comprising a polymer synthase fragment through a peptide linker or spacer of a desired length that facilitates independent folding of the fusion polypeptides.

In one embodiment the amino acid sequence of the fusion polypeptide the antigen(s) or binding domain(s) is contiguous with the N-terminus of the amino acid sequence comprising a particle-forming protein, preferably a polymer synthase, or a C-terminal synthase fragment.

In one embodiment the amino acid sequence of the fusion protein the antigen(s) or binding domain(s) is indirectly fused with the C-terminus of the amino acid sequence comprising a particle-forming protein, preferably a polymer synthase, or a N-terminal polymer synthase fragment through a peptide linker or spacer of a desired length to facilitate independent folding of the fusion polypeptides.

In one embodiment the amino acid sequence of the fusion polypeptide the antigen(s) or binding domain(s) is contiguous with the N-terminus of the amino acid sequence encoding a depolymerase, or a C-terminal depolymerase fragment.

One advantage of the fusion polypeptides according to the present invention is that the modification of the proteins binding to the surface of the polymer particles does not affect the functionality of the proteins involved in the formation of the polymer particles. For example, the functionality of the polymer synthase is retained if a recombinant polypeptide is fused with the N-terminal end thereof, resulting in the production of recombinant polypeptide on the surface of the particle. Should the functionality of a protein nevertheless be impaired by the fusion, this shortcoming is offset by the presence of an additional particle-forming protein which performs the same function and is present in an active state.

In this manner, it is possible to ensure a stable bond of the recombinant polypeptide bound to the polymer particles via the particle-forming proteins.

It should be appreciated that the arrangement of the proteins in the fusion polypeptide is dependent on the order of gene sequences in the nucleic acid contained in the plasmid.

For example, it may be desired to produce a fusion polypeptide wherein the *M. tuberculosis* antigen is indirectly fused to the polymer synthase. The term "indirectly fused" refers to a fusion polypeptide comprising a particle-forming protein, preferably a polymer synthase, and at least one *M. tuberculosis* or *M. bovis* antigen or a binding domain capable of binding at least one *M. tuberculosis* or *M. bovis* antigen that are separated by an additional protein which may be any protein that is desired to be expressed in the fusion polypeptide.

When used in the context of particles for use in the diagnosis or treatment of *tuberculosis*, it may be desired to produce a fusion polypeptide wherein the *M. tuberculosis* or *M. bovis* antigen(s) or at least one *M. tuberculosis* or *M. bovis* antigen binding domain is indirectly fused to the polymer synthase.

In one embodiment the additional protein is selected from a particle-forming protein or a fusion polypeptide, or a linker or spacer to facilitate independent folding of the fusion polypeptides, as discussed above. In this embodiment it would be necessary to order the sequence of genes in the plasmid to reflect the desired arrangement of the fusion polypeptide.

In other embodiments the *M. tuberculosis* or *M. bovis* antigen(s) or binding domain(s) capable of binding at least one *M. tuberculosis* or *M. bovis* antigen are directly fused to the polymer synthase. The term "directly fused" is used herein to indicate where two or more peptides are linked via peptide bonds.

It is also possible to form a particle wherein the particle comprises at least two distinct fusion polypeptides that are bound to the polymer particle. For example, a first fusion polypeptide comprising a *M. tuberculosis* or *M. bovis* antigen or a binding domain capable of binding at least one *M. tuberculosis* or *M. bovis* antigen fused to a polymer synthase could be bound to the polymer particle. When used in the context of particles for use in the treatment of *tuberculosis*, the exemplary particle comprises a first fusion polypeptide comprising a *M. tuberculosis* or *M. bovis* antigen, for example, or at least one *M. tuberculosis* or *M. bovis* antigen binding domain fused to a polymer synthase bound to the polymer particle.

In one embodiment the expression construct is expressed in vivo. Preferably the expression construct is a plasmid which is expressed in a microorganism, preferably *Escherichia coli*.

In one embodiment the expression construct is expressed in vitro. Preferably the expression construct is expressed in vitro using a cell free expression system.

In one embodiment one or more genes can be inserted into a single expression construct, or one or more genes can be integrated into the host cell genome. In all cases expression can be controlled through promoters as described above.

In one embodiment the expression construct further encodes at least one additional fusion polypeptide comprising a *M. tuberculosis* or *M. bovis* antigen or at least one *M. tuberculosis* or *M. bovis* antigen binding domain and a particle-forming protein as discussed above.

Plasmids useful herein are shown in the examples and are described in detail in PCT/DE2003/002799 published as WO 2004/020623 (Bernd Rehm) and PCT/NZ2006/000251 published as WO 2007/037706 (Bernd Rehm) which are each herein incorporated by reference in their entirety.

It will be appreciated that the binding domain capable of binding at least one *M. tuberculosis* or *M. bovis* antigen are able to bind *M. tuberculosis* or *M. bovis* antigen present in the subject to which the binding domain is administered or in which the immune response is to be elicited.

Thus, in the context of use for the diagnosis or treatment of *tuberculosis*, it will be appreciated that the *M. tuberculosis* or *M. bovis* antigen binding domains are able to bind at least one *M. tuberculosis* or *M. bovis* antigen, for example a *M. tuberculosis* or *M. bovis* antigen present in the subject to which the *M. tuberculosis* or *M. bovis* antigen binding domain is administered or in which the immune response is to be elicited.

6. Hosts for Particle Production

The particles of the present invention are conveniently produced in a host cell, using one or more expression constructs as herein described. Polymer particles of the invention can be produced by enabling the host cell to express the expression construct. This can be achieved by first introducing the expression construct into the host cell or a progenitor of the host cell, for example by transforming or transfecting a host cell or a progenitor of the host cell with the expression construct, or by otherwise ensuring the expression construct is present in the host cell.

Following transformation, the transformed host cell is maintained under conditions suitable for expression of the fusion polypeptides from the expression constructs and for formation of polymer particles. Such conditions comprise those suitable for expression of the chosen expression construct, such as a plasmid in a suitable organism, as are known in the art. For example, and particularly when high yield or overexpression is desired, provision of a suitable substrate in the culture media allows the particle-forming protein component of a fusion polypeptide to form a polymer particle.

Accordingly, the present invention provides a method for producing polymer particles, the method comprising:

providing a host cell comprising at least one expression construct of the invention, maintaining the host cell under conditions suitable for expression of the expression construct and for formation of polymer particles; and separating the polymer particles from the host cells.

Preferably the host cell is, for example, a bacterial cell, a fungi cell, yeast cell, a plant cell, an insect cell or an animal cell, preferably an isolated or non-human host cell. Host cells useful in methods well known in the art (e.g. Sambrook et al., 1987; Ausubel et al., 1987) for the production of recombinant polymer particles are frequently suitable for use in the methods of the present invention, bearing in mind the considerations discussed herein.

Suitable prokaryote host cells comprise, for example, eubacteria, such as Gram-negative or Gram-positive organisms, for example, Enterobacteriaceae such as *E. coli*. Various *E. coli* strains are publicly available, such as *E. coli* K12 strain MM294 (ATCC 31,446); *E. coli* X1776 (ATCC 31,537); *E. coli* strain W3110 (ATCC 27,325) and K5 772 (ATCC 53,635). Other suitable prokaryotic host cells include other Enterobacteriaceae such as *Escherichia* spp., *Enterobacter, Erwinia, Klebsiella, Proteus, Salmonella*, e.g., *Salmonella typhimurium, Serratia*, e.g., *Serratia marcescans*, and *Shigella*, as well as Bacilli such as *B. subtilis* and *B. licheniformis, Pseudomonas* such as *P. aeruginosa*, and *Actinomycetes* such as *Streptomyces, Rhodococcus, Corynebacterium* and *Mycobaterium*.

In some embodiments, for example, *E. coli* strain W3110 may be used because it is a common host strain for recombinant DNA product fermentations. Preferably, the host cell secretes minimal amounts of proteolytic enzymes. For example, strain W3110 may be modified to effect a genetic mutation in the genes encoding proteins endogenous to the host, with examples of such hosts including *E. coli* W3110 strain 1A2, which has the complete genotype tonA; *E. coli* W3110 strain 9E4, which has the complete genotype tonA ptr3; *E. coli* W3110 strain 27C7 (ATCC 55,244), which has the complete genotype tonA ptr3 phoA E15 (argF-lac)169 degP ompT kanr; *E. coli* W3110 strain 37D6, which has the complete genotype tonA ptr3 phoA E15 (argF-lac)169 degP ompT rbs7 ilvG kanr; *E. coli* W3110 strain 40B4, which is strain 37D6 with a non-kanamycin resistant degP deletion mutation.

In some preferred embodiments, for example, *Lactococcus lactis* strains that do not produce lipopolysaccharide endotoxins may be used. Examples of *Lactococcus lactis* strains include MG1363 and *Lactococcus lactis* subspecies *cremoris* NZ9000.

In addition to prokaryotes, eukaryotic microbes such as filamentous fungi or yeast are suitable cloning or expression hosts for use in the methods of the invention, for example. Examples include *Saccharomyces cerevisiae*, a commonly used lower eukaryotic host microorganism. Other examples include *Schizosaccharomyces pombe* (Beach and Nurse, 1981; EP 139,383), *Kluyveromyces* hosts (U.S. Pat. No. 4,943,529; Fleer et al., 1991) such as, e.g., *K. lactis* (MW98-8C, CBS683, CBS4574; Louvencourt et al., 1983), *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906; Van den Berg et al, 1990), *K. thermotolerans*, and *K. marxianus; yarrowia* (EP 402,226); *Pichia pastoris* (EP 183,070; Sreekrishna et al., 1988); *Candida; Trichoderma reesia* (EP 244,234); *Neurospora crassa* (Case et al., 1979); *Schwanniomyces* such as *Schwanniomyces occidentalis* (EP 394,538 published 31 Oct. 1990); and filamentous fungi such as, e.g., *Neurospora, Penicillium, Tolypocladium* (WO 91/00357 published 10 Jan. 1991), and *Aspergillus* hosts such as *A. nidulans* (Ballance et al., 1983; Tilburn et al., 1983; Yelton et al., 1984) and *A. niger* (Kelly and Hynes, 1985). Methylotropic yeasts are suitable herein and comprise yeast capable of growth on methanol selected from the genera consisting of *Hansenula, Candida, Kloeckera, Pichia, Saccharomyces, Torulopsis*, and *Rhodotorula*. A list of specific species that are exemplary of this class of yeasts may be found in Anthony, 1982.

Examples of invertebrate host cells include insect cells such as *Drosophila* S2 and *Spodoptera* Sf9, as well as plant cells, such as cell cultures of cotton, corn, potato, soybean, petunia, tomato, and tobacco. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells.

Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., J. Gen Virol. 36:59 (1977)); baby hamster kidney cells (BHK, ATCC CCL 10); Chinese hamster ovary cells/-DHFR (CHO, Urlaub et al., 1980); mouse sertoli cells (TM4, Mather, 1980); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., 1982); MRC 5 cells; FS4 cells; and a human hepatoma line (Hep G2).

Eukaryotic cell lines, and particularly mammalian cell lines, will be preferred when, for example, the antigen capable of eliciting a cell-mediated immune response or the binding domain capable of binding the antigen capable of eliciting a cell-mediated immune response or the *M. tuberculosis* or *M. bovis* antigen or the *M. tuberculosis* or *M. bovis* antigen binding domain requires one or more post-translational modifications, such as, for example, glycation. For example, one or more antigens capable of eliciting a cell-mediated immune response may require post-translational modification to be immunogenic or optimally immunogenic, and may thus be usefully expressed in an expression host capable of such post-translational modifications.

In one embodiment the host cell is a cell with an oxidising cytosol, for example the *E. coli* Origami strain (Novagen).

In another embodiment the host cell is a cell with a reducing cytosol, preferably *E. coli.*

The host cell, for example, may be selected from the genera comprising *Ralstonia, Acaligenes, Pseudomonas* and *Halobiforma*. Preferably the microorganism used is selected from the group comprising, for example, *Ralstonia eutropha, Alcaligenes latus, Escherichia coli, Pseudomonas fragi, Pseudomonas putida, Pseudomonas oleovorans, Pseudomonas aeruginosa, Pseudomonas fluorescens*, and *Halobiforma haloterrestris*. This group comprises both microorganisms which are naturally capable of producing biocompatible, biodegradable particles and microorganisms, such as for example *E. coli*, which, due to their genetic makeup, are not capable of so doing. The genes required to enable the latter-stated microorganisms to produce the particles are introduced as described above.

Extremely halophilic archaea produce polymer particles with lower levels of unspecific binding of protein, allowing easier isolation and purification of the particles from the cells.

In principle, any culturable host cell may be used for the production of polymer particles by means of the above-described process, even if the host cell cannot produce the substrates required to form the polymer particles due to a different metabolism. In such cases, the necessary substrates are added to the culture medium and are then converted into polymer particle by the proteins which have been expressed by the genes which have been introduced into the cell.

Genes utilized to enable the latter-stated host cells to produce the polymer particles include, for example, a thiolase, a reductase or a polymer synthase, such as phaA thiolase, phaB ketoacyl reductase or phaC synthase from *Ralstonia eutropha*. Which genes are used to augment what the host cell lacks for polymer particle formation will be dependent on the genetic makeup of the host cell and which substrates are provided in the culture medium.

The genes and proteins involved in the formation of polyhydroxyalkanoate (PHA) particles, and general considerations for particle formation are reported in Madison, et al, 1999; published PCT International Application WO 2004/020623 (Bernd Rehm); and Rehm, 2003; Brockelbank J A. et al., 2006; Peters and Rehm, 2006; Backstrom et al, (2006) and Rehm, (2006), all of which are herein incorporated by reference.

A polymer synthase alone can be used in any host cell with (R)-Hydroxyacyl-CoA or other CoA thioester or derivatives thereof as a substrate.

The polymer particle can also be formed in vitro. Preferably, for example, a cell free expression system is used. In such systems a polymer synthase is provided. Purified polymer synthase, such as that obtainable from recombinant production, or in cell free systems capable of protein translation, that obtainable in the cell free system itself by way of introduction of an expression construct encoding a polymer synthase, will be preferred. In order to produce an environment to allow particle formation in vitro the necessary substrates for polymer particle formation should be included in the media.

The polymer synthase can be used for the in vitro production of functionalised polymer particles using (R)-Hydroxyacyl-CoA or other CoA thioester as a substrate, for example.

The fusion polypeptides can be purified from lysed cells using a cell sorter, centrifugation, filtration or affinity chromatography prior to use in in vitro polymer particle production.

In vitro polymer particle formation enables optimum control of surface composition, including the level of fusion polypeptide coverage, phospholipid composition and so forth.

It will be appreciated that the characteristics of the polymer particle may be influenced or controlled by controlling the conditions in which the polymer particle is produced. This may include, for example, the genetic make up of the host cell, eg cell division mutants that produce large granules, as discussed in Peters and Rehm, 2005. The conditions in which a host cell is maintained, for example temperature, the presence of substrate, the presence of one or more particle-forming proteins such as a particle size-determining protein, the presence of a polymer regulator, and the like.

In one embodiment, a desirable characteristic of the polymer particle is that it is persistent. The term “persistent” refers to the ability of the polymer particle to resist degradation in a selected environment. An additional desirable characteristic of the polymer particle is that it is formed from the polymer synthase or particle-forming protein and binds to the C- or N-terminal of the polymer synthase or particle-forming protein during particle assembly.

In some embodiments of the invention it is desirable to achieve overexpression of the expression constructs in the host cell. Mechanisms for overexpression a particular expression construct are well known in the art, and will depend on the construct itself, the host in which it is to be expressed, and other factors including the degree of overexpression desired or required. For example, overexpression can be achieved by i) use of a strong promoter system, for example the T7 RNA polymerase promoter systemin prokaryotic hosts; ii) use of a high copy number plasmid, for example a plasmid containing the colE1 origin of replication or iii) stabilisation of the messenger RNA, for example through use of fusion sequences, or iv) optimization of translation through, for example, optimization of codon usage, of ribosomal binding sites, or termination sites, and the like. The benefits of overexpression may allow the production of smaller particles where desired and the production of a higher number of polymer particles.

The composition of the polymers forming the polymer particles may affect the mechanical or physiochemical properties of the polymer particles. For example, polymer particles differing in their polymer composition may differ in half-life or may release biologically active substances, in particular pharmaceutical active ingredients, at different rates. For example, polymer particles composed of C6-C14 3-hydroxy fatty acids exhibit a higher rate of polymer degradation due to the low crystallinity of the polymer. An increase in the molar ratio of polymer constituents with relatively large side chains on the polymer backbone usually reduces crystallinity and results in more pronounced elastomeric properties. By controlling polymer composition in accordance with the process described in the invention, it is accordingly possible to influence the biodegradability of the polymer particles and thus affect the duration the polymer particles (and when present the one or more antigens capable of eliciting a cell-mediated immune response or the binding domains of the antigens capable of eliciting a cell-mediated immune response on the particle or the one or more *M. tuberculosis* or *M. bovis* antigens or *M. tuberculosis* or *M. bovis* antigen binding domains on the particle, are maintained in, for example, a subject to whom they are administered, or to affect the release rate for biologically active substances present on or in the polymer particles, in particular pharmaceutically active agents or skin-care ingredients.

At least one fatty acid with functional side groups is preferably introduced into the culture medium as a substrate for the formation of the polymer particles, with at least one hydroxy fatty acid and/or at least one mercapto fatty acid and/or at least one β-amino fatty acid particularly preferably being introduced. "Fatty acids with functional side groups" should be taken to mean saturated or unsaturated fatty acids. These also include fatty acids containing functional side groups which are selected from the group comprising methyl groups, alkyl groups, hydroxyl groups, phenyl groups, sulfhydryl groups, primary, secondary and tertiary amino groups, aldehyde groups, keto groups, ether groups, carboxyl groups, O-ester groups, thioester groups, carboxylic acid amide groups, hemiacetal groups, acetal groups, phosphate monoester groups and phosphate diester groups. Use of the substrates is determined by the desired composition and the desired properties of the polymer particle.

The substrate or the substrate mixture may comprise at least one optionally substituted amino acid, lactate, ester or saturated or unsaturated fatty acid, preferably acetyl-CoA.

In one embodiment an adjuvant, an immunomodulatory agent or molecule, such as an immunostimulatory agent or molecule, or other compound useful in the preparation of vaccines is provided in the substrate mixture and is incorporated into the polymer particle during polymer particle formation, or is allowed to diffuse into the polymer particle.

The polymer particle may comprise a polymer selected from poly-beta-amino acids, polylactates, polythioesters and polyesters, for example. Most preferably the polymer comprises polyhydroxyalkanoate (PHA), preferably poly(3-hydroxybutyrate) (PHB).

The polymer synthase or polymer particle preferably comprises a phospholipid monolayer that encapsulates the polymer particle. Preferably said particle-forming protein spans said lipid monolayer.

The polymer synthase or particle-forming protein is preferably bound to the polymer particle or to the phospholipid monolayer or is bound to both.

The particle-forming protein is preferably covalently or non-covalently bound to the polymer particle it forms.

Preferably at least about 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, 99% or 100% of the surface area of the polymer particle is covered by fusion polypeptides.

In certain circumstances it may be desirable to control the size of the particles produced in the methods of the invention, for example to produce particles particularly suited to a given application. For example, it may be desirable to produce polymer particles comprising one or more antigens capable of eliciting a cell-mediated immune response of a relatively large size, for example to elicit a robust cell-mediated immune response. For example, in the context of particles for use in the treatment of *tuberculosis*, it may be desirable to produce polymer particles comprising one or more *M. tuberculosis* or *M. Bovis* antigens of a relatively large size, for example to elicit a robust cell-mediated immune response. Methods to control the size of polymer particles are described in PCT/DE2003/002799 published as WO 2004/020623, and PCT/NZ2006/000251 published as WO 2007/037706.

In some embodiments, particle size is controlled by controlling the expression of the particle-forming protein, or by controlling the expression of a particle size-determining protein if present, for example.

In other embodiments of the present invention, for example, particle size control may be achieved by controlling the availability of a substrate, for example the availability of a substrate in the culture medium. In certain examples, the substrate may be added to the culture medium in a quantity such that it is sufficient to ensure control of the size of the polymer particle.

It will be appreciated that a combination of such methods may be used, allowing the possibility for exerting still more effective control over particle size.

In various embodiments, for example, particle size may be controlled to produce particles having a diameter of from about 10 nm to 3 μm, preferably from about 10 nm to about 900 nm, from about 10 nm to about 800 nm, from about 10 nm to about 700 nm, from about 10 nm to about 600 nm, from about 10 nm to about 500 nm, from about 10 nm to about 400 nm, from about 10 nm to about 300 nm, from about 10 nm to about 200 nm, and particularly preferably of from about 10 nm to about 100 nm.

In other embodiments, for example, particle size may be controlled to produce particles having a diameter of from about 10 nm to about 90 nm, from about 10 nm to about 80 nm, from about 10 nm to about 70 nm, from about 10 nm to about 60 nm, from about 10 nm to about 50 nm, from about 10 nm to about 40 nm, from about 10 nm to about 30 nm, or from about 10 nm to about 20 nm.

Other ranges of average polymer size, for example, including ranges within the above recited ranges, are specifically contemplated, for example polymer particles having a diameter of from about 50 to about 500 nm, from about 150 to about 250 nm, or from about 100 to about 500 nm, etc.

In various embodiments, for example, 90% of the particles produced have a diameter of about 200 nm or below, 80% have a diameter about 150 nm or below, 60% have a diameter about 100 nm or below, 45% have a diameter about 80 nm or below, 40% have a diameter about 60 nm or below, 25% have a diameter about 50 nm or below, and 5% have a diameter about 35 nm or below In various embodiments, for example, the method produces polymer particles with an average diameter less than about 200 nm, less than about 150 nm, or less than about 110 nm.

7. Compositions and formulations

The polymer particles of the invention can be formulated as compositions suitable for use in the methods of the invention for a number of different applications, for example, formulated for administration via a particular route or formulated for storage, can be stably maintained as particles outside the host cell that produced them, and that these particles can be designed to suit a number of applications.

In one embodiment, for example, the compositions useful herein are formulated to allow for administration to a subject by any chosen route, including but not limited to oral or parenteral (including topical, subcutaneous, intramuscular and intravenous) administration.

Thus, for example, a pharmaceutical composition useful according to the invention may be formulated with an appropriate pharmaceutically acceptable carrier (including excipients, diluents, auxiliaries, and combinations thereof) selected with regard to the intended route of administration and standard pharmaceutical practice. For example, pharmaceutical compositions intended for vaccination can contain one or more adjuvants or immunostimulants, as are well known in the art. For example, a composition useful according to the invention can be administered orally as a powder, liquid, tablet or capsule, or topically as an ointment, cream or lotion. Suitable formulations may contain additional agents as required, including emulsifying, antioxidant, flavouring or colouring agents, and may be adapted for immediate-, delayed-, modified-, sustained-, pulsed- or controlled-release.

Thus, the invention also is directed to doses, dosage forms, formulations, compositions and/or devices comprising one or more polymer particles of the invention including those disclosed herein, useful for the diagnosis or therapy of diseases, disorders, and/or conditions in humans and other mammals and other disorders as disclosed herein. The use of these dosage forms, formulations compositions and/or devices comprising one or more polymer particles of the invention enables effective identification and/or treatment of these conditions. The invention provides, for example, dosage forms, formulations, devices and/or compositions containing one or more polymer particles of the invention. The dosage forms, formulations, devices and/or compositions of the invention may be formulated to optimize bioavailability, immunogenicity, or to maintain plasma, blood, or tissue concentrations within the immunogenic, diagnostic, or therapeutic range, including for extended periods. Controlled delivery preparations may also be used to optimize the antigen concentration at the site of action, for example.

The dosage forms, formulations, devices and/or compositions of the invention are in certain embodiments formulated for periodic administration, for example to provide continued exposure to the one or more polymer particles of the invention. Strategies to elicit a beneficial immunological response, for example those that employ one or more "booster" vaccinations, are well known in the art, and such strategies may be adopted in the practise of the present invention.

Diagnostic compositions of the present invention are in certain embodiments formulated for topical administration, for example formulated for use in skin prick tests.

Pharmaceutical compositions and dosage forms can be administered via the parenteral route, and this route will be preferred for certain embodiments of methods of eliciting an immune response, such as those described herein. Examples of parenteral dosage forms include aqueous solutions, isotonic saline or 5% glucose of the active agent, or other well-known pharmaceutically acceptable excipients. Cyclodextrins, for example, or other solubilising agents well-known to those familiar with the art, can be utilized as pharmaceutical excipients for delivery of the therapeutic agent.

Examples of dosage forms suitable for oral administration include, but are not limited to tablets, capsules, lozenges, or like forms, or any liquid forms such as syrups, aqueous solutions, emulsions and the like, capable of providing a therapeutically effective amount of a polymer particle of the invention. Capsules can contain any standard pharmaceutically acceptable materials such as gelatin or cellulose. Tablets can be formulated in accordance with conventional procedures by compressing mixtures of the active ingredients with a solid carrier and a lubricant. Examples of solid carriers include starch and sugar bentonite. Active ingredients can also be administered in a form of a hard shell tablet or a capsule containing a binder, e.g., lactose or mannitol, a conventional filler, and a tabletting agent.

Examples of dosage forms suitable for transdermal administration include, but are not limited, to transdermal patches, transdermal bandages, and the like. Examples of dosage forms suitable for topical administration of the compositions and formulations of the invention are any lotion, stick, spray, ointment, paste, cream, gel, etc., whether applied directly to the skin or via an intermediary such as a pad, patch or the like.

Examples of dosage forms suitable for suppository administration of the compositions and formulations of the invention include any solid dosage form inserted into a bodily orifice particularly those inserted rectally, vaginally and urethrally.

Examples of dosage of forms suitable for injection of the compositions and formulations of the invention include delivery via bolus such as single or multiple administrations by intravenous injection, subcutaneous, subdermal, and intramuscular administration or oral administration.

Examples of dosage forms suitable for depot administration of the compositions and formulations of the invention include pellets or small cylinders of polymer particles of the invention or solid forms wherein the polymer particles of the invention are entrapped in a matrix of biodegradable polymers, microemulsions, liposomes or are microencapsulated.

Examples of infusion devices for compositions and formulations of the invention include infusion pumps containing one or more polymer particles of the invention at a desired amount for a desired number of doses or steady state administration, and include implantable drug pumps.

Examples of implantable infusion devices for compositions, and formulations of the invention include any solid form in which the polymer particles of the invention are encapsulated within or dispersed throughout a biodegradable polymer or synthetic, polymer such as silicone, silicone rubber, silastic or similar polymer.

Examples of dosage forms suitable for transmucosal delivery of the compositions and formulations of the invention include depositories solutions for enemas, pessaries, tampons, creams, gels, pastes, foams, nebulised solutions, powders and similar formulations containing in addition to the active ingredients such carriers as are known in the art to be appropriate. Specifically contemplated are dosage forms suitable for inhalation or insufflation of the compositions and formulations of the invention, including compositions comprising solutions and/or suspensions in pharmaceutically acceptable, aqueous, or organic solvents, or mixture thereof and/or powders. Transmucosal administration of the compositions and formulations of the invention may utilize any mucosal membrane but commonly utilizes the nasal, buccal, vaginal and rectal tissues. Formulations suitable for nasal administration of the compositions and formulations of the invention may be administered in a liquid form, for example, nasal spray, nasal drops, or by aerosol administration by nebulizer, including aqueous or oily solutions of the polymer particles. Formulations for nasal administration, wherein the carrier is a solid, include a coarse powder having a particle size, for example, of less than about 100 microns, preferably less, most preferably less than about 50 microns, which is administered in the manner in which snuff is taken, i.e., by rapid inhalation through the nasal passage from a container of the powder held close up to the nose. Formulations of the invention may be prepared as aqueous solutions for example in saline, solutions employing benzyl alcohol or other suitable preservatives, absorption promoters to enhance bio-availability, fluorocarbons, and/or other solubilising or dispersing agents known in the art.

Examples of dosage forms suitable for buccal administration of the compositions and formulations of the invention include lozenges, tablets and the like, compositions comprising solutions and/or suspensions in pharmaceutically acceptable, aqueous, or organic solvents, or mixtures thereof and/or powders.

Examples of dosage forms suitable for sublingual administration of the compositions and formulations of the invention include lozenges, tablets and the like, compositions comprising solutions and/or suspensions in pharmaceutically acceptable, aqueous, or organic solvents, or mixtures thereof and/or powders.

Examples of dosage forms suitable for opthalmic administration of the compositions and formulations of the invention include inserts and/or compositions comprising solutions and/or suspensions in pharmaceutically acceptable, aqueous, or organic solvents.

Examples of formulations of compositions, including vaccines and controlled drug formulations, useful for delivery of the compositions and formulations of the invention are found in, for example, Sweetman, S. C. (Ed.). Martindale. The Complete Drug Reference, 33rd Edition, Pharmaceutical Press, Chicago, 2002, 2483 pp.; Aulton, M. E. (Ed.) Pharmaceutics. The Science of Dosage Form Design. Churchill Livingstone, Edinburgh, 2000, 734 pp.; and, Ansel, H. C., Allen, L. V. and Popovich, N. G. Pharmaceutical Dosage Forms and Drug Delivery Systems, 7th Ed., Lippincott 1999, 676 pp. Excipients employed in the manufacture of drug delivery systems are described in various publications known to those skilled in the art including, for example, Kibbe, E. H. Handbook of Pharmaceutical Excipients, 3rd Ed., American Pharmaceutical Association, Washington, 2000, 665 pp. The USP also provides examples of modified-release oral dosage forms, including those formulated as tablets or capsules. See, for example, The United States Pharmacopeia 23/National Formulary 18, The United States Pharmacopeial Convention, Inc., Rockville Md., 1995 (hereinafter "the USP"), which also describes specific tests to determine the drug release capabilities of extended-release and delayed-release tablets and capsules. The USP test for drug release for extended-release and delayed-release articles is based on drug dissolution from the dosage unit against elapsed test time. Descriptions of various test apparatus and procedures may be found in the USP. Further guidance concerning the analysis of extended release dosage forms has been provided by the F.D.A. (See Guidance for Industry. Extended release oral dosage forms: development, evaluation, and application of in vitro/in vivo correlations. Rockville, Md.: Center for Drug Evaluation and Research, Food and Drug Administration, 1997).

Further examples of dosage forms of the invention include, but are not limited to modified-release (MR) dosage forms including delayed-release (DR) forms; prolonged-action (PA) forms; controlled-release (CR) forms; extended-release (ER) forms; timed-release (TR) forms; and long-acting (LA) forms. For the most part, these terms are used to describe orally administered dosage forms, however these terms may be applicable to any of the dosage forms, formulations, compositions and/or devices described herein. These formulations effect delayed total drug release for some time after drug administration, and/or drug release in small aliquots intermittently after administration, and/or drug release slowly at a controlled rate governed by the delivery system, and/or drug release at a constant rate that does not vary, and/or drug release for a significantly longer period than usual formulations.

In certain embodiments, a diagnostically or therapeutically effective amount of one or more polymer particles of the invention or of one or more antigens comprising one or more polymer particles of the invention is from about 1 ug/kg to about 1 g/kg. Exemplary diagnostically or therapeutically effective dose ranges include, for example, from about 1 µg/kg to about 500 mg/kg, from about 1 µg/kg to about 400 mg/kg, from about 1 µg/kg to about 300 mg/kg, from about 1 µg/kg to about 200 mg/kg, from about 1 µg/kg to about 100 mg/kg, from about 1 µg/kg to about 90 mg/kg, from about 1 µg/kg to about 80 mg/kg, from about 1 µg/kg to about 70 mg/kg, from about 1 µg/kg to about 60 mg/kg, from about 1 µg/kg to about 50 mg/kg, from about 5 µg/kg to about 50 mg/kg, from about 10 µg/kg to about 50 mg/kg, from about 50 µg/kg to about 50 mg/kg, from about 100 µg/kg to about 50 mg/kg, from about 200 µg/kg to about 50 mg/kg, from about 300 µg/kg to about 50 mg/kg, from about 400 µg/kg to about 50 mg/kg, from about 500 µg/kg to about 50 mg/kg, from about 600 µg/kg to about 50 mg/kg, from about 700 µg/kg to about 50 mg/kg, from about 800 µg/kg to about 50 mg/kg, from about 900 µg/kg to about 50 mg/kg, about 1 mg/kg to about 50 mg/kg, about 5 mg/kg to about 50 mg/kg, about 10 mg/kg to about 50 mg/kg, about 15 mg/kg to about 50 mg/kg, about 20 mg/kg to about 50 mg/kg, about 25 mg/kg to about 50 mg/kg, about 30 mg/kg to about 50 mg/kg, about 35 mg/kg to about 50 mg/kg, about 40 mg/kg to about 50 mg/kg, or about 45 mg/kg to about 50 mg/kg.

Other diagnostically or therapeutically effective dose ranges include, for example, from about 1 mg/kg to about 1 g/kg, from about 1.5 mg/kg to about 950 mg/kg, about 2 mg/kg to about 900 mg/kg, about 3 mg/kg to about 850 mg/kg, about 4 mg/kg to about 800 mg/kg, about 5 mg/kg to about 750 mg/kg, about 5 mg/kg to about 700 mg/kg, 5 mg/kg to about 600 mg/kg, about 5 mg/kg to about 500 mg/kg, about 10 mg/kg to about 400 mg/kg, about 10 mg/kg to about 300 mg/kg, about 10 mg/kg to about 200 mg/kg, about 10 mg/kg to about 250 mg/kg, about 10 mg/kg to about 200 mg/kg, about 10 mg/kg to about 200 mg/kg, about 10 mg/kg to about 150 mg/kg, about 10 mg/kg to about 100 mg/kg, about 10 mg/kg to about 75 mg/kg, about 10 mg/kg to about 50 mg/kg, or about 15 mg/kg to about 35 mg/kg.

In some embodiments of the invention targeting human subjects, a diagnostically or therapeutically effective amount of one or more polymer particles of the invention or of one or more antigens comprising one or more polymer particles of the invention is, for example, from about 10 mg to about 10 g per dose. Other diagnostically or therapeutically effective dose ranges include, for example, from about 20 mg to about 9 g, from about 30 mg to about 8 g, from about 40 mg to about 7 g, from about 50 mg to about 6 g, from about 60 mg to about 5 g, from about 70 mg to about 4 g, about 80 mg to about 3 g, about 100 mg to about 2 g, about 100 mg to about 1.5 g, about 200 mg to about 1400 mg, about 200 mg to about 1300 mg, about 200 mg to about 1200 mg, about 200 mg to about 1100 mg, about 200 mg to about 1000 mg, about 300 mg to about 900 mg, about 300 mg to about 800, about 300 mg to about 700 mg or about 300 mg to about 600 mg per dose.

The invention also in part provides low dose compositions, formulations and devices comprising one or more one or more polymer particles of the invention. For example, low dose compositions, formulations and the like, are administered in an amount sufficient to provide, for example, dosages from about 0.001 mg/kg to about 5 mg/kg, about 0.01 mg/kg to about 4.5 mg/kg, about 0.02 mg/kg to about 4 mg/kg, about 0.02 to about 3.5 mg/kg, about 0.02 mg/kg to about 3 mg/kg, about 0.05 mg/kg to about 2.5 mg/kg, about 0.05 mg/kg to about 2 mg/kg, about 0.05-0.1 mg/kg to about 5 mg/kg, about 0.05-0.1 mg/kg to about 4 mg/kg, about 0.05-0.1 mg/kg to about 3 mg/kg, about 0.05-0.1 mg/kg to about 2 mg/kg, about 0.05-0.1 mg/kg to about 1 mg/kg, and/or any other doses or dose ranges within the ranges set forth herein, of one or more one or more polymer particles of the invention or of one or more antigens comprising one or more polymer particles of the invention.

The doses described herein, may be administered in a single dose or multiple doses or divided doses. For example, doses may be administered, once, twice, three, four or more times over a treatment regime, as is well known in the immunological arts.

The efficacy of a composition useful according to the invention can be evaluated both in vitro and in vivo. See, e.g., the examples below. Briefly, the composition can be tested in vitro or in vivo for its ability to induce a cell-mediated immune response. For in vivo studies, the composition can be fed to or injected into an animal (e.g., a mouse) and its effects on eliciting an immune response are then assessed. Based on the results, an appropriate dosage range and administration route are then determined.

In some embodiments of the invention, a diagnostically or therapeutically effective amount is an amount effective to elicit an immunological response, such as, for example, a concentration of IFN-gamma in the blood of from about 0.5 ng/mL to about 20 ng/mL, about 0.5 ng/mL to about 15 ng/mL, about 0.5 ng/mL to about 10 ng/mL, about 0.5 ng/mL to about 9 ng/mL, about 1 ng/mL to about 8 ng/mL, about 2 ng/mL to about 7 ng/mL or about 3 ng/mL to about 6 ng/mL.

In some circumstances, including post infection or during prolonged infection, elevated IFN-gamma blood concentrations are observed, and such elevated concentrations should be accounted for in assessing a baseline against which elicitation of an effective immunological response by the polymer particles of the invention is to be assessed.

8. Exemplary Uses of Polymer Particles of the Invention

It has been discovered that the polymer particles, e.g., polyhydroxyalkyl polymer particles, can be stably maintained as particles outside the host cell that produced them, and that these particles can be designed to suit a number of applications.

Functionalised polymer particles may comprise one or more surface-bound antigens capable of eliciting a cell-mediated or other immune response, one or more substances bound to binding domains of an antigen capable of eliciting a cell-mediated or other immune response, or a combination thereof.

In one embodiment, for example, a substance is immobilised on the particle surface during particle formation, bound to a binding domain capable of binding an antigen capable of eliciting a cell-mediated immune response, or integrated into the particle by loading, diffusion or incorporation.

In the context of use in the diagnosis or treatment of tuberculosis, for example, exemplary polymer particles comprise one or more surface-bound M. tuberculosis or M. Bovis antigens, and optionally one or more substances bound to M. tuberculosis or M. bovis antigen binding domains, or a combination thereof.

In one embodiment a substance may be immobilised on the particle surface during particle formation, bound to, for example, a M. tuberculosis or M. bovis antigen binding domain, or integrated into the particle by loading, diffusion or incorporation. Covalent linking to the surface of the polymer particle, for example, by cross-linking, is also specifically contemplated.

In one embodiment the substance is selected from the list comprising, for example, a protein or protein fragment, a peptide, a polypeptide, an antibody or antibody fragment, an antibody binding domain, an antigen, an antigenic determinant, an epitope, an immunogen or fragment thereof, or any combination of any two or more thereof.

In one embodiment DNA from an intracellular pathogen can be fragmented and inserted into expression constructs encoding fusion polypeptides that comprise a polymer synthase. In this way, polymer particles displaying intracellular pathogen antigenic determinants can be produced and screened using serum from infected patients and antigen-presenting particles identified, isolated and reproduced using well-known and scalable bacterial production systems.

In one embodiment multiple antigens capable of eliciting a cell-mediated (or other) immune response are immobilised on the surface of the polymer particles.

In one embodiment DNA from a M. tuberculosis or M. bovis bacterium, for example, can be fragmented and inserted into expression constructs encoding fusion polypeptides that comprise a polymer synthase. In this way, polymer particles displaying M. tuberculosis or M. bovis antigenic determinants, for example, can be produced and screened using serum from infected patients and antigen-presenting particles identified, isolated and reproduced using well-known and scalable bacterial production systems.

In one embodiment, for example, multiple M. tuberculosis or M. bovis or other antigens are immobilised on the surface of the polymer particles.

One aspect of the invention relates to the ability of the polymer particles carrying one or more antigens to elicit an immune response. In one embodiment, the polymer particles comprise at least one antigen capable of eliciting a cell-mediated or other immune response fused to the polymer particle. The polymer polymer particles display at least one antigens capable of eliciting a cell-mediated or other immune response on their surface to stimulate an optimal immune response to the antigenic moieties.

In one embodiment, the polymer particles carrying one or more antigens elicit an immune response. In one embodiment, the polymer particles comprise at least one *M. tuberculosis* antigen, for example, fused to the polymer particle. The polymer polymer particles display at least one *M. tuberculosis* antigen, for example, on their surface to stimulate an optimal immune response to the antigenic moieties.

In one embodiment, for example, more than one antigen or a combination of antigen and adjuvant or other immunomodulatory agent or molecule, such as an immunostimulatory agent or molecule, are present in or on the particle or present in a composition. Typically, the presence of the combination of antigens, adjuvants, or other immunomodulatory agents or molecules will be to further enhance the immune response.

The present invention also relates to a method of eliciting an immune response in a subject, wherein the method comprises administering to a subject in need thereof a polymer particle comprising a particle-forming protein, preferably a polymer synthase, for example, fused to one or more binding domain(s) capable of binding an antigen selected from an ESAT6, a CFP10, an Rv3615c, or an Rv3020c antigen. In this embodiment, on administration to the subject the binding domain(s) capable of binding said antigens bind endogenous antigen, thereby facilitating an immune response.

For example, antigens capable of eliciting a cell-mediated immune response that is present in the subject prior to administration of the particle comprising at least one *M. tuberculosis* antigen binding domain, for example, but is unable to elicit an effective immune response in the subject, is on binding to the particle able to elicit an effective immune response or is effective to enhance the subject's immune response.

In one embodiment, the invention provides a method of eliciting an immune response in a subject infected with *tuberculosis*, for example, or previously immunised against *tuberculosis*, for example, wherein the method comprises administering to a subject in need thereof a polymer particle comprising a particle-forming protein fused to a *M. tuberculosis* or *M. bovis* antigen binding domain, for example.

In this embodiment, for example, on administration to the subject the *M. tuberculosis* or *M. bovis* antigen binding domain may bind to an endogenous *M. tuberculosis* or *M. bovis* antigen. It will be appreciated that binding of a polymer particle comprising a *M. tuberculosis* or *M. bovis* antigen binding domain to endogenous *M. tuberculosis* or *M. bovis* antigen, for example, is able to elicit or enhance the subject's immune response.

For example, *M. tuberculosis* or *M. bovis* antigen that is present in the subject prior to administration of the particle comprising at least one *M. tuberculosis* or *M. bovis* antigen binding domain, but is unable to elicit an effective immune response in the subject, is on binding to the particle able to elicit an effective immune response or is effective to enhance the subject's immune response.

It will be appreciated that the present invention provides particles, compositions and methods that elicit an immune response in subjects to whom they are administered. Preferably, the magnitude of the immune response elicited in response to one or more antigens presented to a subject using the particles, compositions and methods of the invention is greater than that elicited in response to the antigen alone (that is, in the absence of a particle or composition of the invention or presented by a method other than those provided herein). Methods to quantify the magnitude of an immune response, and particularly a cell-mediated immune response, are well known in the art.

Particularly contemplated methods of eliciting an immune response, for example in the diagnosis of *tuberculosis*, comprise skin tests. The most common formats of the test for bovine are the caudal fold test (CFT), the single intradermal cervical tuberculin test (SIT) and the single intradermal comparative cervical tuberculin (SICCT) test (Monaghan et al. (1994) Vet. Microbiol, vol. 40 pp 111-24).

These test formats use a purified protein derivative (PPD) tuberculin prepared from a culture of *M. bovis* (PPD-B) as the primary diagnostic antigen. Additionally, the SICCT test attempts to address environmental sensitisation through the use of a *M. avium* derived PPD (PPD-A). The skin tests referred to herein may be any of a CFT, SIT or SICCT test, as described in the Office International des Epizooties (OIE) Manual of Diagnostic Tests and Vaccines for Terrestrial Animals 2009 (ISBN-10:92-9044-718-4; http://www.oie.int/fileadmin/Home/eng/Health_standards/tahm/2008/pdf/2.04.07_BOVINE_TB. pdf, accessed 8 Nov. 2013, in particular Chapter 2.4.7. Positive test criteria are outlined therein, and will be well understood by a person skilled in the art.

Therefore, when the polymer particles and diagnostic reagents of the invention elicit a positive result when administered in a skin test, this result is determined by, for example, detection of an increased thickness and/or induration of skin at the site of administration (e.g., injection). As outlined in the manual, callipers or other measurement devices are helpfully used, for example. In certain embodiments, the skin thickness is determined prior to administration/injection, and again at one or more of, for example, about 24, 36, 48, 72, 96 or about 120 hours after administration/injection. Determining skin thickness at about 72 hours after injection is typical, as exemplified herein.

Additional particularly contemplated methods of diagnosing *tuberculosis* comprise diagnostic assays such as cytokine or cell-based assays, including for example assays of cell-mediated immunity, in which a sample obtained from a subject is contacted with a polymer particle of the invention. Typically, the sample will contain a population of cells, including immune cells such as T cells, capable of mediating or modulating an immune response. Particularly contemplated assays include interferon-gamma assays, such as interferon-gamma ELISA. In particular examples, the response in an assay, such as an interferon-gamma ELISA, is capable of distinguishing between subjects suffering from *tuberculosis*, and subjects immunised against *tuberculosis*, for example with BCG.

9. Modulators of an Immune Response

In certain circumstances it will be desirable to produce polymer particles displaying a fusion protein comprising two or more antigens from the group comprising ESAT6, CFP10, Rv3615c, and Rv3020c. Alternatively, a fusion protein comprising at least one or more of these antigens with an adjuvant or other modulator of an immune response is desirable for eliciting an immune response.

In one example, a polymer particle of the invention comprises one or more antigens together with one or more toll-like receptors, including one or more toll-like receptors able to bind one or more of the group of ligands comprising LPS, lipoproteins, lipopeptides, flagellin, double-stranded RNA, unmethylated CpG islands, or bacterial or viral DNA or RNA. Similarly, a composition of the invention may comprise a population of polymer particles comprising one or more TB antigens, and a population of polymer particles comprising one or more immunomodulatory molecules, such as one or more toll-like receptors.

The presence of one or more immunomodulatory molecules may be useful in eliciting a humoral-specific immune response, or a cell-mediated-specific immune response, or in eliciting an immune response comprising a combination of both humoral and cell-mediated responses.

The invention consists in the foregoing and also envisages constructions of which the following gives examples only.

EXAMPLES

Example 1

Construction of Plasmids and Production of PHA Polymer Particles

This example describes the preparation of polymer particles of the invention, and their assessment as diagnostic reagents for *tuberculosis*.

Introduction

Three specific TB antigens, the 6-kDa early secretory antigenic target (ESAT6), the 10-kDa culture filtrate protein (CFP10), and Rv3615c are expressed by members of the pathogenic *M. tuberculosis* complex which includes *M. bovis*, but are not expressed by the majority of non-pathogenic environmental mycobacteria and the BCG vaccine strain (Millington, 2011; Waters et al, 2004). These immunodominant proteins have previously been evaluated in interferon-γ (IFN-γ) tests for the diagnosis of TB in cattle (Buddle et al, 1999). Recently, the skin testing of cattle using a combination of these three proteins indicated that they had a high sensitivity for detection of animals infected with *M. bovis* while differentiating against those vaccinated with BCG (Whelan et al, 2010; Casal et al, 2012). This example describes an investigation of the functional display of these three antigens on polyester particles and their performance in bovine TB skin tests.

Materials and Methods

Bacterial Strains and Growth Conditions.

The bacteria strains used in this study are listed in Table 1. The *E. coli* strain used for cloning, XL1-Blue (Stratagene) transformed with the expression plasmids were grown in Luria broth (Difco, Detroit, Mich.) supplemented with tetracycline (12.5 μg/ml) and ampicillin (75 μg/ml). Medium for growth of *E. coli* BL21 (DE3) used for production of polyester particles contained chloramphenicol (50 μg/ml) instead of tetracycline.

Plasmids, Oligonucleotides and Generation of Plasmids for Production of Bioparticles Displaying Mycobacterial Antigens.

Plasmids and primers used in this study are listed in Tables 1 and 2, respectively. General molecular cloning procedures were implemented as described elsewhere (Sambrook et al, 1989). DNA sequences of new plasmid constructs were verified by DNA sequencing. The biosynthesis of polyester requires, in addition to the polyester synthase gene (phaC), the enzymes PhaA and PhaB for precursor synthesis, and these enzymes were encoded on the plasmid pMCS69 (Amara et al, 2003).

TABLE 1

Bacterial strains and plasmids

| Strains or plasmids | Relevant characteristics | References |
|---|---|---|
| *E. coli* strains | | |
| BL21 (DE3) | F-dcm ompT hsdS(rB-mB-) gal λ(DE3) | Stratagene |
| XL1-Blue | recA1 endA1 gyrA96 thi-1 hsdR17 supE44 relA1 lac [F'proAB lacIqZΔM15 Tn10 (Tetr)] | Stratagene |
| Plasmid name | | |
| pET-14b | Apr; T7 promoter | Novagen |
| pET-14b phaC | pET-14b derivative containing phaCgene fragment | (Peters et al, 2005) |
| pET-14b cfp10-phaC | pET-14b derivative containing NdeI fragment gene cfp10fused to the 5' end of phaC | Herein |
| pET-14b rv3615c-phaC | pET-14b derivative containing NdeI fragment generv3615cfused to the 5' end of phaC | Herein |
| pET-14b esat6-phaC | pET-14b derivative containing NdeI fragment geneesat6fused to the 5' end of phaC | Herein |
| pET-14b cfp10-linker-rv3615c-phaC | pET-14b derivative containing SpeI fragment genes cfp10-linker-rv3615cfused to the 5' end of phaC | Herein |
| pET-14b cfp10-linker-rv3615c-phaC-esat6 | pET-14b derivative containing SpeI fragment genescfp10-linker-rv3615cfused to the 5' end of phaCand XhoI/BamHI fragment gene esat6 fused to the 3' end of phaCvia a linker sequence | Herein |
| pMCS69 | Cm$_r$; T7 promoter, pBBR1MCS derivative containing the genes phaA and phaB from *C. necator* co-linear to lac promoter | (Amara et al, 2003) |
| pUC57-esat6 | Cloning vector, ColE1 origin, Apr, XhoI/BamHI fragment gene ESAT6 | Herein |

Tetr, tetracycline resistance
Apr, ampicillin resistance
Cmr, chloramphenicol resistance

TABLE 2

Primers

| Primer name | Restriction site (underlined) | Sequence from 5' to 3' | SEQ. ID. No. |
|---|---|---|---|
| CFP10_fwd | NdeI | AACATATGGCA GAAATGAAAAC GGATGCGGC | 16 |

TABLE 2 -continued

Primers

| Primer name | Restriction site (underlined) | Sequence from 5' to 3' | SEQ. ID. No. |
|---|---|---|---|
| CFP10_rev | NdeI | TT<u>CATATG</u>GAA ACCCATTTGAG AGCTCAGAGCC | 17 |
| Rv3615c_fwd | NdeI | AA<u>CATATG</u>ACC GAAAACCTGAC GGTTCAGCCGG | 18 |
| Rv3615c_rev | NdeI | TT<u>CATATG</u>GGT GAACAGGCCGT CGATTGCTTTA C | 19 |
| ESAT6_fwd | NdeI | AA<u>CATATG</u>ACG GAACAACAATG GAACTTTGCTG GC | 20 |
| ESAT6_rev | NdeI | TT<u>CATATG</u>TGC GAACATGCCCG TGACATTGCCT TC | 21 |

To display the TB genes on the surfaces of the polyester particles, the genes encoding amino acid sequences of ESAT-6 (see Table 3, SEQ. ID. No. 1]), CFP-10 (see Table 3, SEQ. ID. No. 2, and RV3615c (see Table 3, SEQ. ID. No. 3) were synthesized by DNA2.0 (CA, USA) using the PCR primers identified in Table 2, optimized to the codon usage of $E.$ $coli$. An NdeI restriction site was inserted at both the 5' and 3' ends of each gene.

TABLE 3

Amino acid sequences of TB antigens

| Antigen | AA sequence | Seq. ID. No. |
|---|---|---|
| ESAT-6 | MTEQQWNFAGIEAAASAIQGNVTSIHSLLDEGKQS LTKLAAAWGGSGSEAYQGVQQKWDATATELNNALQ NLARTISEAGQAMASTEGNVTGMFA | 1 |
| CFP-10 | MAEMKTDAATLAQEAGNFERISGDLKTQIDQVEST AGSLQGQWRGAAGTAAQAAVVRFQEAANKQKQELD EISTNIRQAGVQYSRADEEQQQALSSQMGF | 2 |
| RV3615c | MTENLTVQPERLGVLASHHDNAAVDASSGVEAAAG LGESVAITHGPYCSQFNDTLNVYLTAHNALGSSLH TAGVDLAKSLRIAAKIYSEADEAWRKAIDGLFT | 3 |

The respective synthesized NdeI fragments encoding CFP-10, ESAT-6 or Rv3615c were inserted into the plasmid pHAS-Ag85A-ESAT-6 (Parlane et al, 2009) after hydrolysis with NdeI which resulted in plasmids pET-14b cfp10-phaC, pET-14b Rv3615c-phaC and pET-14b Esat-6-PhaC, respectively. The codon-optimised nucleotide sequences encoding the CFP10-PhaC fusion polypeptide, the Rv3615c-PhaC fusion polypeptide, and the ESAT6-PhaC fusion polypeptide, are presented herein as SEQ. ID. NO. 12, SEQ. ID. NO. 13, and SEQ. ID. NO. 14, respectively.

The plasmid construct, pET-14b cfp10-linker-rv3615c-phaC-esat6, encoding the three TB antigen genes was made as follows. The codon-optimised nucleotide sequence encoding the CFP10-linker-Rv3615c-PhaC-ESAT6 fusion polypeptide is presented herein as SEQ. ID. NO. 15.

The XhoI-BamHI fragment encoding the esat6 gene was sub-cloned into pET-14b cfp10-linker-rv3615c-phaC-MalE hydrolysed with XhoI-BamHI to generate the final plasmid, pET-14b cfp10-linker-rv3615c-phaC-esat6, which contained the three TB antigen genes.

A schematic representation of the plasmids used to display TB antigens on the surface of the polyester particles is shown in FIG. 1. The DNA constructs containing one TB gene, pET-14b cfp10-phaC (FIG. 1A), pET-14b rv3615c-phaC (FIG. 1B), and pET-14b esat6-phaC (FIG. 1C), and three TB genes, pET-14b cfp10-linker-rv3615c-phaC-esat6 (FIG. 1D) are shown. The amino acid sequence of the polypeptide comprising these three TB antigens encoded by pET-14b cfp10-linker-rv3615c-phaC-esat6 is presented in Table 4 below as SEQ. ID. NO. 10.

Production and Isolation of Polyester Particles.

Polyester particles displaying mycobacterial proteins or control particles alone were produced in $E.$ $coli$ BL21 (DE3) as previously described (Parlane et al, 2009).

Briefly, $E.$ $Coli$ stains were grown at 37° C. in LB and induced with 1 mM isopropyl-β-D-thiogalactopyranoside to induce protein and cultured for a further 48 h at 25° C. The presence of polyester inclusions was observed by staining cells with the fluorescent lipophilic dye Nile Red and by using fluorescence microscopy (Spiekermann et al, 1999). Transmission electron microscopy (TEM) was employed to assess shape and size of polyester inclusion as well as the number per cell. Polyester granules were isolated as previously described (Peters et al, 2008). Protease inhibitors (Roche, USA) were added as required. To confirm functionality of the PhaC enzyme, the polyester content of the cells was quantitatively determined by gas chromatography-mass spectroscopy (GC-MS) (Bramd; et al. 1988).

Analysis of Proteins Attached to Polyester Particles.

Proteins attached to the polyester particles were separated by SDS-PAGE using 8% polyacrylamide gels and stained with Coomassie blue. Proteins of interest were excised from the gels and subjected to tryptic peptide finger printing using matrix-assisted laser desorption ionisation time-of-flight mass spectrometry (MALDI-TOF/MS) (Jahns et al, 2009).

Enzyme-Linked Immunosorbent Assay (ELISA).

Specific Activity of the Particles displaying the TB antigens was determined by ELISA as previously described (Parlane et al, 2009). Briefly, a high-binding capacity microtitre plate (Greiner bio-one) was coated overnight at 4° C. with 100 μl of purified PHB particles displaying TB proteins or control particles, diluted in carbonate-bicarbonate coating buffer, pH 9.6 (Sigma-Aldrich) at protein concentrations ranging from 100 μg/ml to 0.05 μg/ml over serial dilutions. As positive controls, the microtitre plates were also coated overnight at 4° C. with 100 μl of free single or a mixture of the three single TB antigens, kindly provided by Dr H. M. Vordermeier (AHVLA, UK), diluted in carbonate-bicarbonate coating buffer, at protein concentrations ranging from 1 μg/ml to 0.125 μg/ml. Plates were washed with phosphate-buffered saline (PBS) containing 0.05% (vol/vol) Tween 20 (PBST) and blocked with 3% (wt/vol) bovine serum albumin for (BSA) for 1 hr at room temperature. Plates were washed with PBST and incubated with mouse monoclonal antibody to CFP-10 or ESAT-6 (both antibodies were from Abcam, Cambridge, UK) or polyclonal rabbit sera produced against recombinant Rv3615c (AgResearch, Hamilton, NZ) or pre-immune rabbit serum for 1 hr at room temperature. The rabbit antiserum against Rv3615c was produced by immunizing a rabbit with 100 μg of Rv3615c mixed in Incomplete Freund's Adjuvant (Sigma) and revaccinating the rabbit twice at 3 week intervals. Following washing with PBST, plates were incubated for 1 hr with anti-mouse IgG-horseradish peroxidase (HRP) conjugate or anti-rabbit HRP-conjugate. After further washing, o-pheylenediamine (OPD) substrate (Abbott Diagnostics, Ill., USA) was added and incubated for 15 min at room. The reaction was stopped with 0.5N $H_2SO_4$, and the absorbance measured at 490 nm on an ELx808iu ultra microtiter plate reader (BIO-TEK Instruments Inc., USA) (Jahns et al, 2008). Results were expressed as optical density units at 490 nm.

TB Skin Test on Cattle.

Ten, 15-month old Friesian-cross cattle were experimentally infected with a dose of approximately $5 \times 10^3$ colony forming units of *M. bovis* intratracheally as previously described (Buddle et al, 1995). These animals were kept on pasture in an isolation unit which was completely separate to paddocks where the 14 control cattle of equivalent age and breed were grazing. All cattle were sourced from TB-free herds and located in TB-free regions of New Zealand. Prior to the *M. bovis* inoculation, the cattle tested negative in the interferon-gamma test (BOVIGAM™ test; Prionics, Switzerland) for bovine TB and the control cattle were negative in this test throughout the study using the standard interpretation as described previously (Buddle et al, 2009). At 27 weeks after *M. bovis* infection, the infected and control cattle were tested in a comparative cervical skin test comparing responses for triple antigen TB polymer particles and control polymer particles with those for PPD from *M. bovis* (PPD-B; 5,000 IU/0.1 ml injection) and *M. avium* (PPD-A; 2,500 IU/0.1 ml injection; AsureQuality, Upper Hutt, New Zealand)). The 0.1 ml inoculum of the TB polyester particle reagent contained 3.3 μg of fusion protein, comprising 0.9 μg of the mycobacterial proteins and 2.4 μg of PhaC protein, mixed in PBS, while the control polyester particles contained 3.3 μg of PhaC protein in PBS. The skin thickness at the site of injection was measured with callipers immediately prior to injection and 72 h later and results expressed as the change in skin thickness (mm). The M. *Bovis*-infected animals were killed and necropsied at 28 weeks after infection. *Tuberculous* lesions typical of those found in naturally-infected animals were identified in the lungs and/or pulmonary lymph nodes of the animals and M. *Bovis* was cultured from the lesions of all these animals using the BACTEC method and confirmation by AccuProbe. All animal procedures were approved by the AgResearch Grasslands animal ethics committee.

Statistical Analyses.

The Kruskall-Wallis test was used to compare the in vitro ELISA responses for the antigen activity on the particles and analyses of the cross-reactivity of the antisera with heterologous antigens. Skin test responses to PPD-B and the triple TB antigen particles were compared by ANOVA. The correlation between the skin test responses for bovine PPB and the triple antigen particle in the experimentally-infected cattle was undertaken using Spearman's rank correlation test. Statistical analyses were conducted using package "agricolae" in R.3.0.1. and statistical significance was denoted when $P<0.05$.

Results

Production and Characterisation of Polyester Particles Displaying Mycobacterial Antigens.

Figure 2:
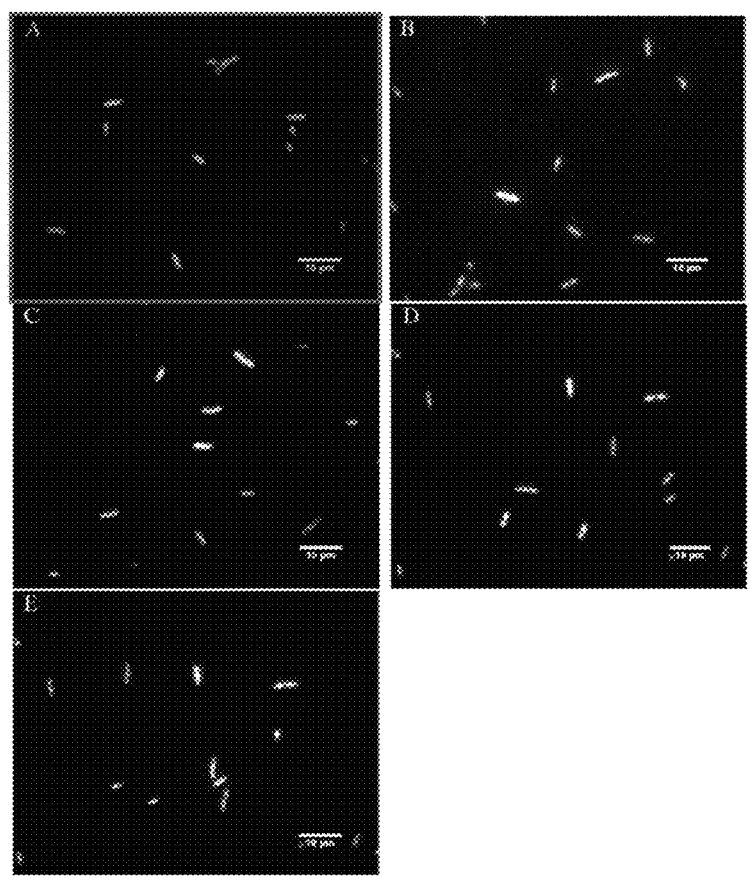
Figure 3:
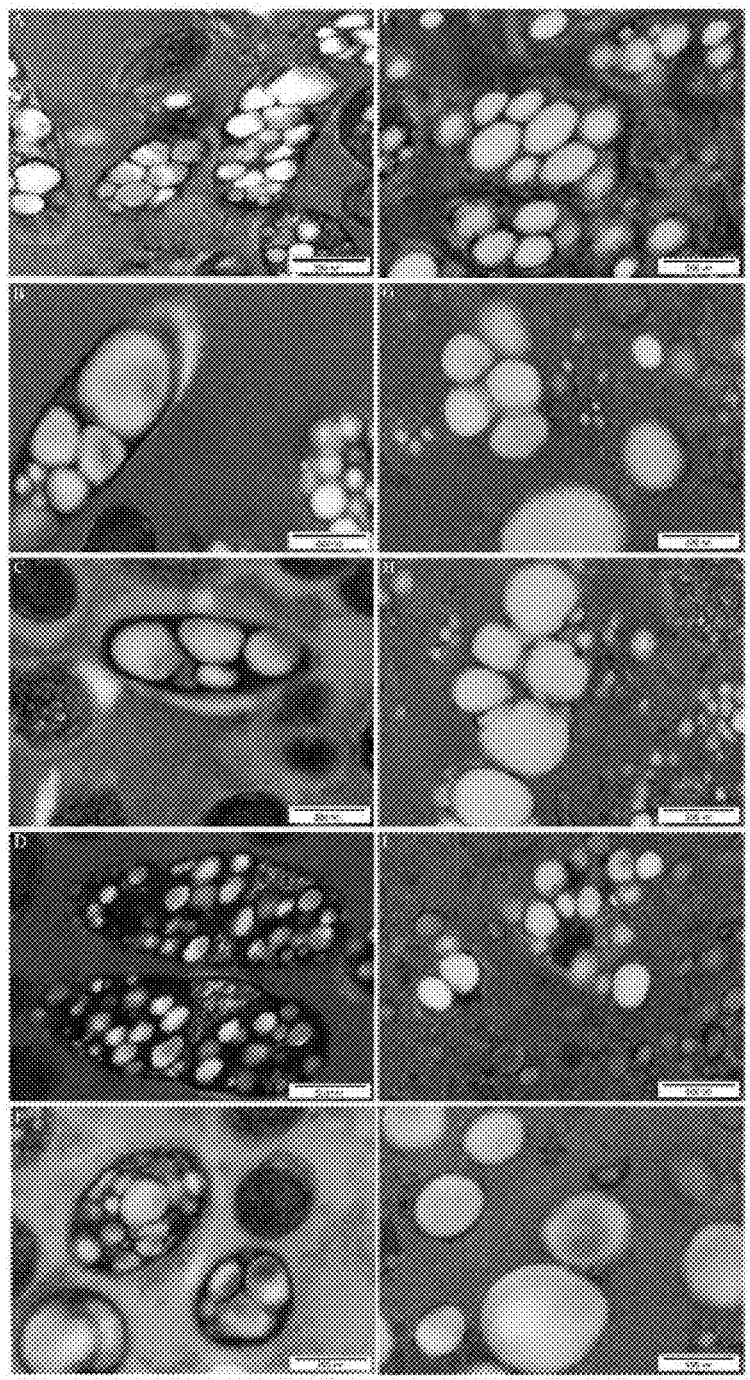

Plasmids encoding PhaC and containing either esat-6, cfp-10 or Rv3615c or all three mycobacterial genes were constructed as described in Materials and Methods. The modular compositions of the various hybrid genes and encoded fusion proteins are outlined in FIG. 1. Hybrid genes were constructed to encode fusion proteins which mediate intracellular production of polyester particles either displaying single TB antigens or all three TB antigens. Respective plasmids were introduced into *E. coli* cells harbouring the plasmid pMCS69 which mediates provision of precursors for polyester synthesis. *E. coli* cells harbouring the various plasmids were cultured to produce polyester particles displaying one or three TB antigens. The presence of intracellular polyester particles in the *E. coli* cells was indicated by fluorescent microscopy using Nile Red staining (FIG. 2). Transmission electron microscopy showed formation of polyester particles mediated by the respective fusion protein inside recombinant *E. coli* (FIG. 3). GC-MS analysis showed that cells were accumulating the polyester, polyhydroxybutyrate, contributing to 31.5%, 10%, 30%, 14.3%, and 40% of cellular dry weight when genes encoding PhaC, CFP10-PhaC, Rv3615c-PhaC, ESAT6-PhaC, and CFP10-Rv3615c-PhaC-ESAT6 were present, respectively.

Display of Recombinant PhaC Antigen Fusion Protein on Polyester Particles.

Figure 4:
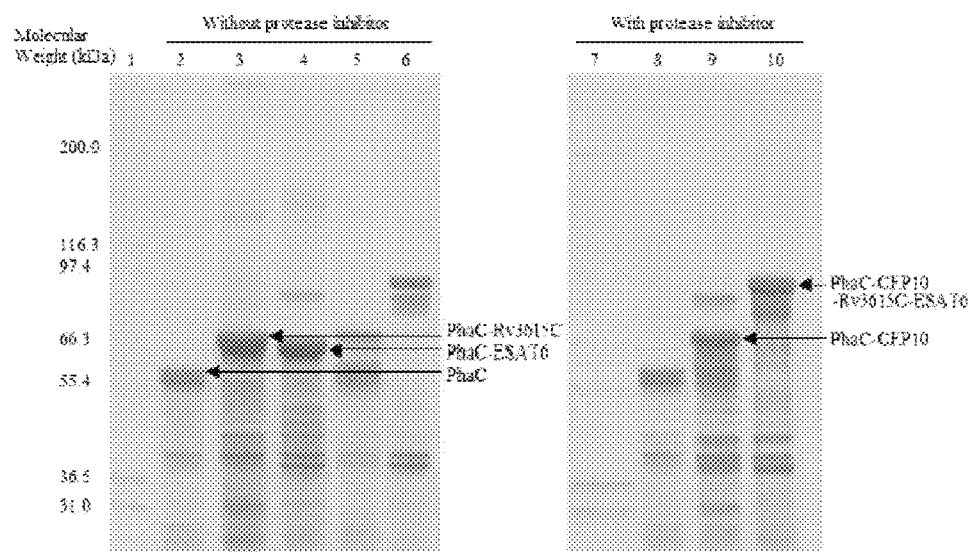

To test whether recombinant fusion proteins were immobilized to polyester particles and whether proteins were susceptible to proteolytic degradation, SDS-PAGE was performed to analyze the polyester particle protein profile. Dominant protein bands were observed which corresponded to proteins with the oretical molecular masses of 63 kDa for PhaC, 69 kDa for the PhaC-ESAT-6 fusion, 73 kDa for CFP10-PhaC, 74 kDa for PhaC-Rv3615c and 90 kDa for CFP10-Rv3615c-PhaC-ESAT6 (FIG. 4). Moreover, these four fusion proteins (CFP10-PhaC (SEQ. ID. NO. 7), Rv3615c-PhaC (SEQ. ID. NO. 8), PhaC-ESAT6 (SEQ. ID. NO. 9), and CFP10-Rv3615c-PhaC-ESAT6 (SEQ. ID. NO. 10)) were identified by tryptic peptide fingerprinting using MALDI-TOF/MS (Table 4). Densitometry analysis of the SDS-PAGE showed that PhaC accounted for 20% of the total protein in the PhaC fraction; CFP10-PhaC, Rv3615c-PhaC, PhaC-ESAT6 and CFP10-Rv3615c-PhaC-ESAT6 accounted for about 26% of the total protein in their corresponding particle fraction.

TABLE 4

Identified peptide fragments of TB fusion protein analyzed by MALDI-TOF/MS

| Protein/Protein sequence | Peptide fragments assigned to the various protein regions |
|---|---|
| CFP10-PhaC (MW: 75.2 kDa) | |
| MAEMKTDAATLAQEAGNFERISGDLKTQIDQVESTAGSLQ GQWRGAAGTAAQAAVVRFQEAANKQKQELDEISTNIRQA GVQYSRADEEQQQALSSQMGFHMATGKGAAASTQEGKS QPFKVTPGPFDPATWLEWSRQWQGTEGNGHAAASGIPGL DALAGVKIAPAQLGDIQQRYMKDFSALWQAMAEGKAEA | CFP10: A2-R20, T27-R57, Q78-R85 PhaC: V122-R137, I164-R175, D179-R209, F216-R226, F247-R281, I296-R308, Y351- |

TABLE 4 -continued

Identified peptide fragments of TB fusion protein analyzed by MALDI-TOF/MS

| Protein/Protein sequence | Peptide fragments assigned to the various protein regions |
|---|---|
| TGPLHDRRFAGDAWRTNLPYRFAAAFYLLNARALTELAD AVEADAKTRQRIRFAISQWVDAMSPANFLATNPEAQRLLI ESGGESLRAGVRNMMEDLTRGKISQTDESAFEVGRNVAV TEGAVVFENEYFQLLQYKPLTDKVHARPLLMVPPCINKYY ILDLQPESSLVRHVVEQGHTVFLVSWRNPDASMAGSTWD DYIEHAAIRAIEVARDISGQDKINVLGFCVGGTIVSTALAV LAARGEHPAASVTLLTTLLDFADTGILDVFVDEGHVQLRE ATLGGGAGAPCALLRGLELANTFSFLRPNDLVWNYVVDN YLKGNTPVPFDLLFWNGDATNLPGPWYCWYLRHTYLQN ELKVPGKLTVCGVPVDLASIDVPTYIYGSREDHIVPWTAA YASTALLANKLRFVLGASGHIAGVINPPAKNKRSHWTND ALPESPQQWLAGAIEHHGSWWPDWTAWLAGQAGAKRA APANYGNARYRAIEPAPGRYVKAKA [SEQ. ID. NO. 7] | R400, I414-K514, L557-K599, F602-K619, S623-K663, A665-R674 |

RV3615C-PhaC (MW: 75.2 kDa)

| MTENLTVQPERLGVLASHHDNAAVDASSGVEAAAGLGES VAITHGPYCSQFNDTLNVYLTAHNALGSSLHTAGVDLAKS LRIAAKIYSEADEAWRKAIDGLFTHMATGKGAAASTQEG KSQPFKVTPGPFDPATWLEWSRQWQGTEGNGHAAASGIP GLDALAGVKIAPAQLGDIQQRYMKDFSALWQAMAEGKA EATGPLHDRRFAGDAWRTNLPYRFAAAFYLLNARALTEL ADAVEADAKTRQRIRFAISQWVDAMSPANFLATNPEAQR LLIESGGESLRAGVRNMMEDLTRGKISQTDESAFEVGRNV AVTEGAVVFENEYFQLLQYKPLTDKVHARPLLMVPPCINK YYILDLQPESSLVRHVVEQGHTVFLVSWRNPDASMAGST WDDYIEHAAIRAIEVARDISGQDKINVLGFCVGGTIVSTAL AVLAARGEHPAASVTLLTTLLDFADTGILDVFVDEGHVQL REATLGGGAGAPCALLRGLELANTFSFLRPNDLVWNYVV DNYLKGNTPVPFDLLFWNGDATNLPGPWYCWYLRHTYL QNELKVPGKLTVCGVPVDLASIDVPTYIYGSREDHIVPWT AAYASTALLANKLRFVLGASGHIAGVINPPAKNKRSHWT NDALPESPQQWLAGAIEHHGSWWPDWTAWLAGQAGAK RAAPANYGNARYRAIEPAPGRYVKAKA [SEQ. ID. NO. 8] | RV3615C: T2-R11, I86-K96 PhaC: V125-R140, I167-R178, D182-R212, F219-R229, F250-R284, I299-R311, Y354-R403, I417-K517, L560-K602 F605-K622, S626-K666, A668-R677 |

ESAT6-PhaC (MW: 74.3 kDa)

| MTEQQWNFAGIEAAASAIQGNVTSIHSLLDEGKQSLTKLA AAWGGSGSEAYQGVQQKWDATATELNNALQNLARTISE AGQAMASTEGNVTGMFAHMATGKGAAASTQEGKSQPFK VTPGPFDPATWLEWSRQWQGTEGNGHAAASGIPGLDALA GVKIAPAQLGDIQQRYMKDFSALWQAMAEGKAEATGPL HDRRFAGDAWRTNLPYRFAAAFYLLNARALTELADAVEA DAKTRQRIRFAISQWVDAMSPANFLATNPEAQRLLIESGG ESLRAGVRNMMEDLTRGKISQTDESAFEVGRNVAVTEGA VVFENEYFQLLQYKPLTDKVHARPLLMVPPCINKYYILDL QPESSLVRHVVEQGHTVFLVSWRNPDASMAGSTWDDYIE HAAIRAIEVARDISGQDKINVLGFCVGGTIVSTALAVLAAR GEHPAASVTLLTTLLDFADTGILDVFVDEGHVQLREATLG GGAGAPCALLRGLELANTFSFLRPNDLVWNYVVDNYLKG NTPVPFDLLFWNGDATNLPGPWYCWYLRHTYLQNELKVP GKLTVCGVPVDLASIDVPTYIYGSREDHIVPWTAAYASTA LLANKLRFVLGASGHIAGVINPPAKNKRSHWTNDALPESP QQWLAGAIEHHGSWWPDWTAWLAGQAGAKRAAPANYG NARYRAIEPAPGRYVKAKA [SEQ. ID. NO. 9] | ESAT6: M1-K33, W58-R74 PhaC: V117-R132, I159-R170, D174-R204, F211-R235, F242-R276, I291-R303, Y346-R395, I409-K509, L552 K594 F597-K614, S618-K658, A660-R669 |

CFP10-RV3615C-PhaC-ESAT6 (MW: 98.1 kDa)

| MAEMKTDAATLAQEAGNFERISGDLKTQIDQVESTAGSLQ GQWRGAAGTAAQAAVVRFQEAANKQKQELDEISTNIRQA GVQYSRADEEQQQALSSQMGFGPGGGGPMTENLTVQPE RLGVLASHHDNAAVDASSGVEAAAGLGESVAITHGPYCS QFNDTLNVYLTAHNALGSSLHTAGVDLAKSLRIAAKIYSE ADEAWRKAIDGLFTTSATGKGAAASTQEGKSQPFKVTPGP FDPATWLEWSRQWQGTEGNGHAAASGIPGLDALAGVKIA PAQLGDIQQRYMKDFSALWQAMAEGKAEATGPLHDRRF AGDAWRTNLPYRFAAAFYLLNARALTELADAVEADAKT RQRIRFAISQWVDAMSPANFLATNPEAQRLLIESGGESLRA GVRNMMEDLTRGKISQTDESAFEVGRNVAVTEGAVVFEN EYFQLLQYKPLTDKVHARPLLMVPPCINKYYILDLQPESSL VRHVVEQGHTVFLVSWRNPDASMAGSTWDDYIEHAAIRA IEVARDISGQDKINVLGFCVGGTIVSTALAVLAARGEHPAA SVTLLTTLLDFADTGILDVFVDEGHVQLREATLGGGAGAP CALLRGLELANTFSFLRPNDLVWNYVVDNYLKGNTPVPF | CFP10: A2-R20, T27-R57, Q78-R85 RV3615C: T108-R117, I192-K202 PhaC: V233-R248, I275-R286, D290-R320, F327-R337, F358-R392, I407-R419, Y462-R511, I525-K625, L668-K710, F713-K730, S734-K774, A776-R785 ESAT6: W877-R893 |

TABLE 4 -continued

Identified peptide fragments of TB fusion protein analyzed by MALDI-TOF/MS

| Protein/Protein sequence | Peptide fragments assigned to the various protein regions |
|---|---|
| DLLFWNGDATNLPGPWYCWYLRHTYLQNELKVPGKLTV<br>CGVPVDLASIDVPTYIYGSREDHIVPWTAAYASTALLANK<br>LRFVLGASGHIAGVINPPAKNKRSHWTNDALPESPQQWLA<br>GAIEHHGSWWPDWTAWLAGQAGAKRAAPANYGNARYR<br>AIEPAPGRYVKAKAHMVLAVAIDKRGGGGGLEMTEQQW<br>NFAGIEAAASAIQGNVTSIHSLLDEGKQSLTKLAAAWGGS<br>GSEAYQGVQQKWDATATELNNALQNLARTISEAGQAMA<br>STEGNVTGMFA [SEQ. ID. NO. 10] | |

Protein degradation was also assessed. As shown in FIG. 4, the samples on the left panel were not treated by protease inhibitor during particle isolation. The Rv3615c-PhaC and PhaC-ESAT6 fusion proteins were stable and did not show degradation (Lanes 3 and 4). However, there was an increased level of protein degradation in the CFP10-PhaC and CFP10-Rv3615c-PhaC-ESAT6 fusion proteins (Lanes 5 and 6). The samples on the right panel were treated with protease inhibitor during particle extraction. The degradation of these two recombinant fusion proteins containing CFP10 was significantly inhibited by protease inhibitor (Lanes 9 and 10). This suggested that the recombinant fusion proteins containing CFP10 were sensitive to protease digestion during particle isolation and purification (FIG. 4). A schematic view of the triple antigen displaying polyester particles is provided in FIG. 5.

Assessment of TB Antigen Reactivity In Vitro

Figure 6:
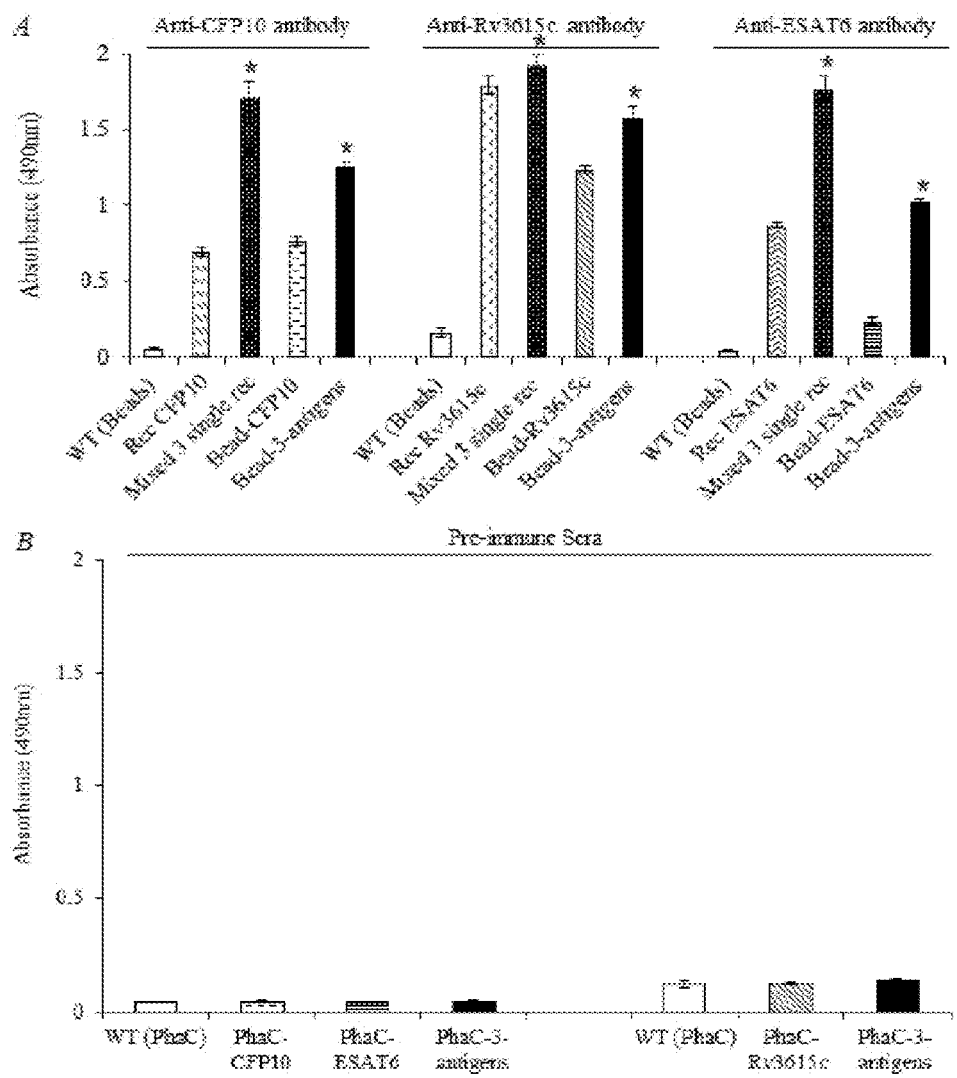

The use of polyester particles displaying one or more TB antigens as TB diagnostic reagents was assessed. ELISA was used to probe the accessibility and structural integrity of TB antigens displayed on the surface of polyester particles in vitro (FIG. 6).

In the reactivity test for the immobilized TB antigens (FIG. 6A) the negative control was the polyester particles carrying only PhaC. The positive controls were free single and a mixture of the three antigens (CFP10, Rv3615c, and ESAT6). Particles carrying the various TB antigens were analyzed. A very low antibody binding of the negative control was observed, which indicated that the polyester particles with no TB antigen displayed did not have binding sites for the three antibodies (anti-CFP10, anti-Rv3615c, and anti-ESAT6). In contrast, there was a dramatic increase in the antibody binding of the positive controls. Particularly, the antibody binding of the immobilized triple TB antigens was significantly higher than that for the displayed single antigens; this was also observed with the soluble triple and soluble single TB antigens (FIG. 6A, $P<0.05$).

Moreover, the negative control experiment using rabbit pre-immune sera instead of the three specific antibodies showed that all the samples have very low antibody binding to the negative control serum (FIG. 6B). Furthermore, the cross-reactivity test showed the antibody binding of TB antigens was specific and the antibody binding of TB antigens was significantly higher when the corresponding antibody was applied compared to that for the heterologous antigens ($P<0.05$).

Assessment of TB Antigen Reactivity In Vivo

Figure 7:
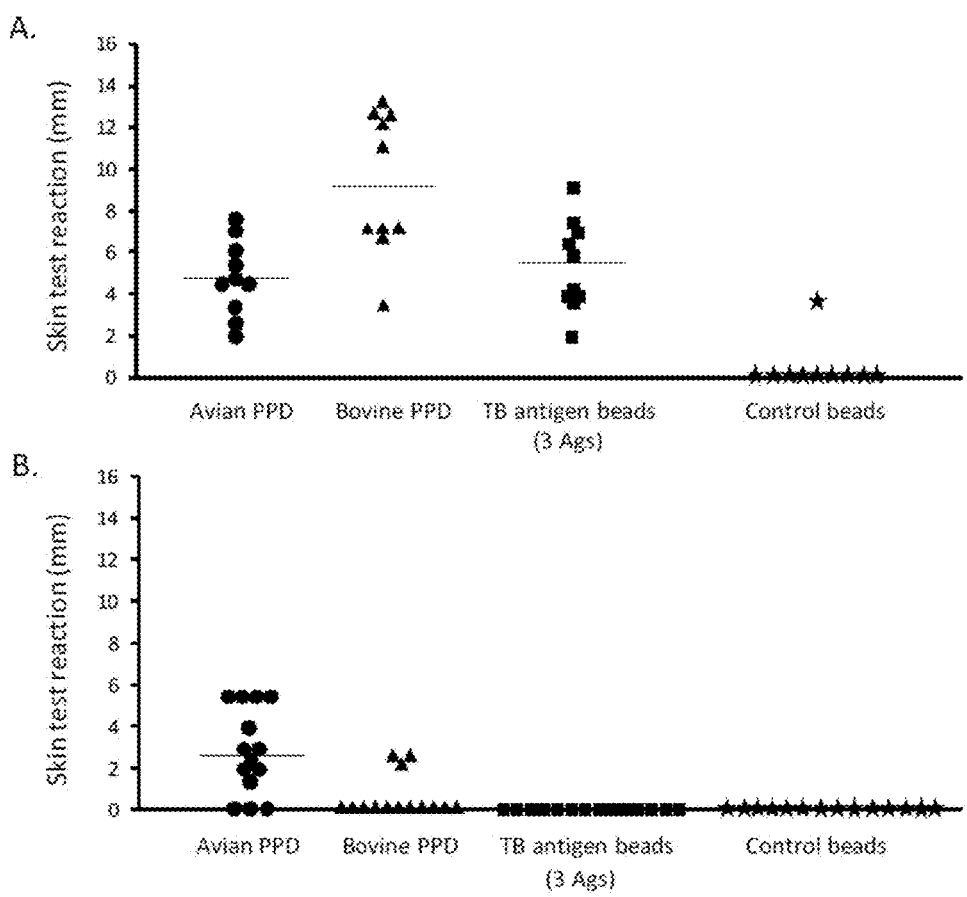
Figure 8:
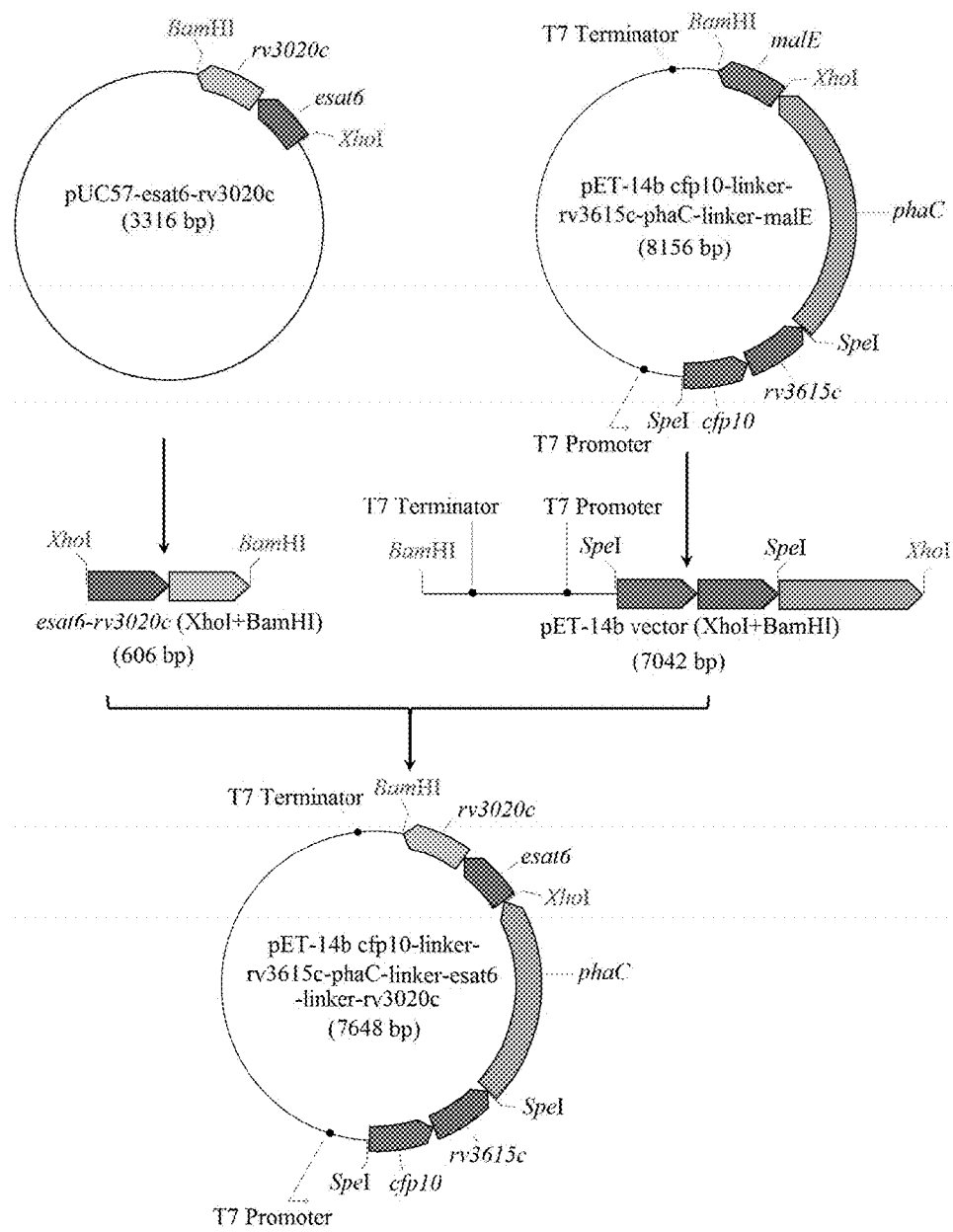
Figure 9:
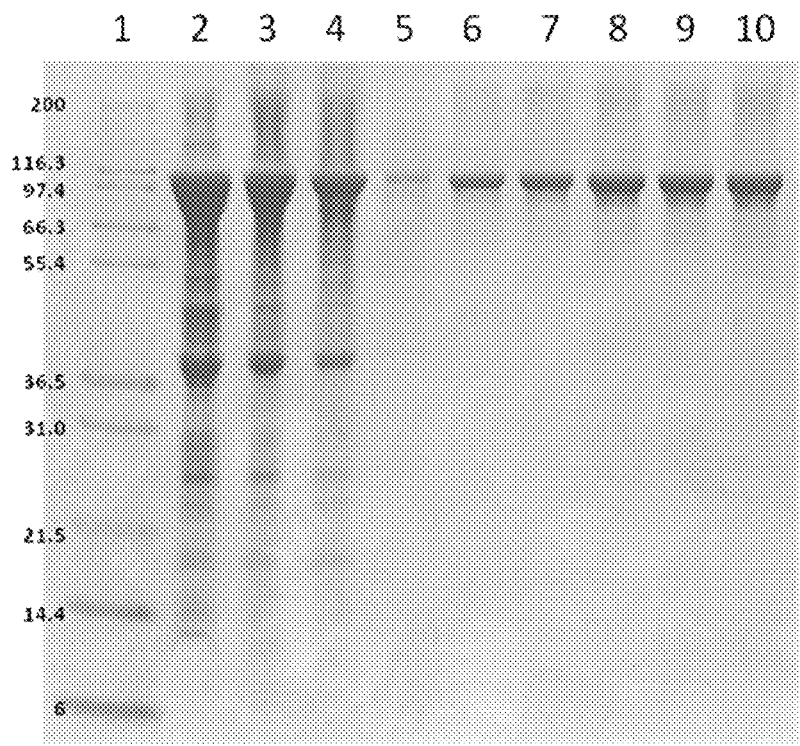

To test the immunogenicity and specificity of the triple TB antigen displaying particles in vivo, the respective particles were intradermally injected into cattle. Four reagents, particles displaying the triple TB antigens, control particles, PPD-B, and PPD-A were administered for the TB skin tests (FIG. 7). All of the experimentally infected animals responded positively in the skin test ($\geq 1$ mm increase in skin test thickness) to PPD-B alone and in addition, all PPD-B responses were greater than those for PPD-A.

Responses to a 0.9 µg/injection of TB antigen fusion proteins displayed on polyester particles were also positive for all animals and there were no significant differences in the responses between PPD-B and TB polyester particles ($P>0.05$). Two animals produced a weak response (2.5 mm increase in skin thickness to the control polyester particles. In contrast, when testing these skin test reagents in 14 equivalent-aged cattle, naturally-sensitized to environmental mycobacteria, none responded positively to the TB polyester particle reagents, while 11 responded positively to PPD-A and three to PPD-B. The skin test responses to PPD-B and the triple antigen particles were compared in the cattle experimentally infected with M. bovis. Although all the cattle responded to the two different antigen preparations, there was no correlation between the sizes of these responses for individual animals.

Discussion

The aim of this study was to produce fusion proteins which mediate formation of polyester particles displaying selected TB antigens (CFP10, ESAT6, Rv3615c) suitable for TB skin test applications. The display of selected TB antigens at the surface of immunogenic polyester particles is anticipated by the applicants to be important for the sensitivity and specificity of the TB skin test.

Figure 5:
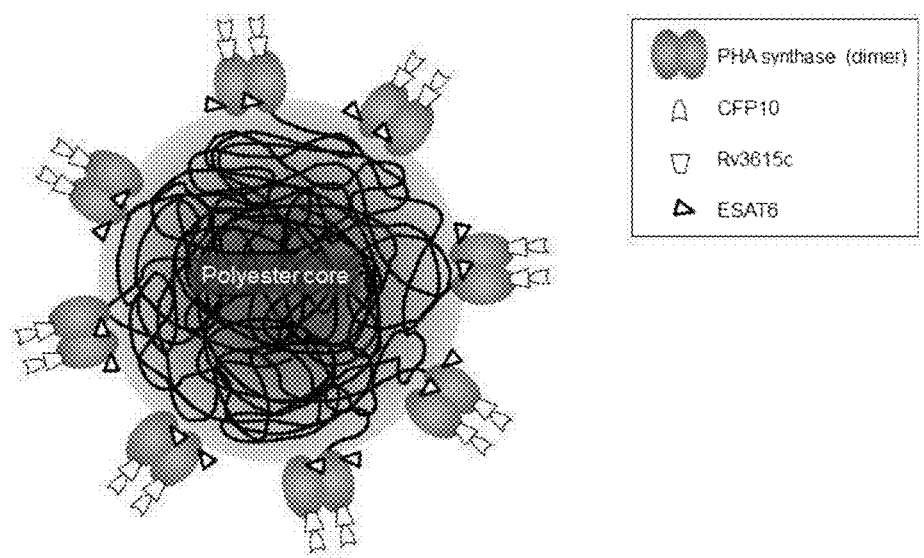

As outlined in FIG. 1 various hybrid genes encoding the polyester particle forming enzyme, PhaC, fused to a single and three TB antigens, were constructed. All four hybrid genes mediated polyester particle production in recombinant E. coli as was assessed by fluorescence microscopy (FIG. 2), TEM (FIG. 3) and GC-MS. This data suggested that the PhaC domain remained active in all of the fusion proteins, catalyzing the synthesis of the polyester and mediateing particle formation. Identity of the fusion proteins was obtained by SDS-PAGE analysis combined with tryptic peptide fingerprinting analysis using MALDI-TOF/MS (Jahns et al, 2009) (FIGS. 4 and 5, Table 3). Fusion proteins attached to the polyester particle surface which contained the antigen CFP10 were found to be susceptible to protease degradation which could be avoided by the addition of protease inhibitors during particle isolation (FIG. 4).

Polyester particle surface display of the respective TB antigen fused to PhaC was investigated by using specific anti-TB antigen antibodies in combination with ELISA (FIG. 6A). Assessment of cross-reactivity of the specific anti-TB antigen antibodies as well as assessment of possible non-specific antibody binding using pre-immune sera suggested that the anti-TB antigen antibodies were highly specific and the antigen displaying particles did not non-specifically bind to antibodies (FIG. 6B, C).

The various particles were found to display the respective TB antigen(s). Interestingly, the triple TB antigen displaying particles showed greater reactivity with the specific antibodies when compared with the respective single TB antigen displaying particles. This was not due to varying expression levels as similar amounts of fusion protein were detected per particle mass (FIG. 4). Hence, the applicants believe, without wishing to be bound by any theory, that the different arrangement of the antigens in the triple antigen fusion protein might have contributed to improve accessibility by the respective specific antibody. The high reactivity of the reagent containing the three immobilized TB antigens is also not caused by cross-reactivity of antibodies. Each antibody only specifically interacted with the corresponding TB antigen.

The polyester particle containing the triple TB antigens was assessed as TB skin test reagent due to its high reactivity with specific antibodies. In addition, the applicants believe, without wishing to be bound by any theory, the manufacture of only one multiple antigen polyester particle type will be a cost-effective strategy preferred to produce several single antigen particles. There is also a demand for a specific diagnostic reagent which distinguishes TB-infected from environmental strain-sensitized or BCG-vaccinated individuals.

A comparative cervical skin test is used in many countries for the diagnosis of bovine TB as both PPD-A and PPD-B contain antigens common to many environmental mycobacteria and a stronger response to PPD-B compared to that for PPD-A is indicative of infection with *M. bovis* (Monaghan et a (Monaghan et al, 1994). TB antigens, CFP10, Rv5c, and ESAT6 (27) are found in members of the pathogenic *M. tuberculosis* complex which includes *M. bovis* and therefore responses to these antigens would indicate a more specific response compared to that for PPD-B, containing a crude mix of antigens.

In this TB skin test study (FIG. 7), all the three reagents (TB antigens), PPD-A, PPD-B, and the triple TB antigen particle reagent, were able to identify TB-infected cattle with a high sensitivity (FIG. 7A). However, the particle reagent containing the triple TB antigens was most accurate in identifying non-infected cattle, naturally exposed to environmental mycobacteria, while PPD-A and PPD-B gave false positive results (FIG. 7)

On the basis of these results, the applicants believe that CFP10-Rv3615c-ESAT6 immobilized on the surface of polyester particle provides a more sensitive, specific, and cost effectively diagnostic reagent when compared to other tests, including free antigens.

Applicants further believe, again without wishing to be bound by any theory, that triple TB antigen displaying polyester particles also have utility in the diagnosis of human TB, mainly caused by *M. tuberculosis*. Indeed, CFP10, ESAT6, and Rv3615c from *M. tuberculosis* strongly cross-react with the orthologous proteins in *M. bovis*, a causative agent of bovine TB (Millington et al, 2011; Waters et al, 2004), and these antigens are immunodominant in both active and latent human TB infection (Millington et al, 2011; Sidders et al, 2008).

This polyester particle TB diagnostic reagent comprising the triple antigens has high specificity and sensitivity, allowing for quick and accurate screening of subjects infected by TB. In addition, the polyester particle based TB skin test has the potential to differentiate between infected and BCG vaccinated subjects This example demonstrates that bacterial polyester particles have been prepared to simultaneously display three TB specific antigens and that these recombinant particles show specific and sensitive performance as TB skin test reagents. This improved skin test showed less false positive results in subjects when compared to the commercial skin test reagents and which in turn reduces a significant economic loss for the end-user.

Example 2

Production of Tetravalent Antigen Polymer Particles

This example describes the preparation of tetravalent polymer particles of the invention comprising 4 TB antigens for use as diagnostic reagents for *tuberculosis*, including the construction and expression of the plasmid, pET-14b cfp10-linker-rv3615c-phaC-linker-esat6-linker-rv3020c.

Materials and Methods

The construction of pET-14b cfp10-linker-rv3615c-phaC-linker-esat6-linker-rv3020c is depicted in FIG. 8. Briefly, the DNA fragment encoding the esat6-rv3020c was isolated from pUC57-esat6-rv3020c by a restriction digest with XhoI and BamHI, followed by separation of DNA fragments using agarose gel electrophoresis and gel purification. The esat6-rv3020c gene (SEQ. ID. NO. 11) was ligated into linearized vector pET-14b cfp10-rv3615c-phaC-linker, generated by restriction digest with XhoI and BamHI, using T4 DNA ligase to generate the final plasmid, pET-14b cfp10-rv3615c-phaC-esat6-rv3020c.

Expression In Vivo

Plasmid pET-14b cfp10-rv3615c-phaC-esat6-rv3020c was expressed as described above in Example 1. SDS-PAGE analysis of the crude lysate, together with samples taken from various steps in the purification of the polymer particle as previously described (Peters et al, 2008), was performed. Again, MALDI-TOF analysis was used to confirm the presence of each of the various protein components in the expressed fusion polypeptide.

Results

FIG. 9 shows the SDS-PAGE analysis of the crude lysate, together with samples taken from various steps in the purification of the polymer particles. The observed molecular weight accords well with the calculated molecular weight.

The results of tryptic peptide fingerprinting using MALDI-TOF/MS are shown in Table 5 below. As shown therein, each of the five component proteins comprising the fusion polypeptide CFP10-Rv3615c-PhaC-ESAT6-Rv3020c (SEQ. ID. NO. 22) were identified, as underlined.

TABLE 5

Identified peptide fragments of a recombinant fusion protein containing four TB antigens analyzed by MALDI-TOF/MS

| Protein/Protein sequence | Peptide fragments assigned to the various protein regions |
|---|---|
| CFP10-Rv3615c-PhaC-ESAT6-Rv3020c (MW: 109.4 kDa) | |
| MAEMKTDAATLAQEAGNFERISGDLKTQIDQVESTA GSLQGQWRGAAGTAAQAAVVRFQEAANKQKQELDE ISTNIRQAGVQYSRADEEQQQALSSQMGFGPGGGGG | CFP10: T6-R20, T27-R57, A86-P102 |
| PMTENLTVQPERLGVLASHHDNAAVDASSGVEAAAG LGESVAITHGPYCSQFNDTLNVYLTAHNALGSSLHTA GVDLAKSLRIAAKIYSEADEAWRKAIDGLFTTS | Rv3615c: P108-R119, I194-K204 |
| ATGKGAAASTQEGKSQPFKVTPGPFDPATWLEWSRQ WQGTEGNGHAAASGIPGLDALAGVKIAPAQLGDIQQ RYMKDFSALWQAMAEGKAEATGPLHDRRFAGDAWR TNLPYRFAAAFYLLNARALTELADAVEADAKTRQRIR FAISQWVDAMSPANFLATNPEAQRLLIESGGESLRAG VRNMMEDLTRGKISQTDESAFEVGRNVAVTEGAVVF ENEYFQLLQYKPLTDKVHARPLLMVPPCINKYYILDL QPESSLVRHVVEQGHTVFLVSWRNPDASMAGSTWD DYIEHAAIRAIEVARDISGQDKINVLGFCVGGTIVSTAL AVLAARGEHPAASVTLLTTLLDFADTGILDVFVDEGH VQLREATLGGGAGAPCALLRGLELANTFSFLRPNDLV WNYVVDNYLKGNTPVPFDLLFWNGDATNLPGPWYC WYLRHTYLQNELKVPGKLTVCGVPVDLASIDVPTYIY GSREDHIVPWTAAYASTALLANKLRFVLGASGHIAGV INIPPAKNKRSHWTNDALPESPQQWLAGAIEHHGSWW PDWTAWLAGQAGAKRAAPANYGNARYRAIEPAPGR YVKAKAHMVLAVAIDKRGGGGG | PhaC: V233-R248, I275-R286, D290-K302, R313-R320, F327-R337, F358-R392, I407-R419, Y462-R511, D518-K625, L668-K710, A776-R785, A801-R812 |
| LEMTEQQWNFAGIEAAASAIQGNVTSIHSLLDEGKQS LTKLAAAWGGSGSEAYQGVQQKWDATATELNNALQ NLARTISEAGQAMASTEGNVTGMFAGGGGG | ESAT6: W877-R893 |
| MSLLDAHIPQLIASHTAFAAKAGLMRHTIGQAEQQA MSAQAFHQGESAAAFQGAHARFVAAAAKVNTLLDI AQANLGEAAGTYVAADAAAASSYTGF [SEQ. ID. NO. 22] | Rv3020c: H946-R976 |

Discussion

This example established that multivalent TB antigen-comprising polymer particles of the invention were able to be successfully prepared by expression of a fusion polypeptide comprising a particle-forming polypeptide fused to 4 different TB antigens. Furthermore, tetravalent particles have been purified for use in the invention.

Example 3

Assessment of Tetravalent PHA Polymer Particles as Diagnostic Reagents

This example describes the assessment of tetravalent polymer particles of the invention as diagnostic reagents for *tuberculosis*. The stability and efficacy of the tetravalent TB antigen-comprising polymer particles (TTPP) described in Example 2 above was assessed in bovine TB skin tests.

Materials and Methods

The materials and methods used in this study were as described in Examples 1 and 2 above, with the addition of the following.

Intradermal Assays—In Vivo Study Design

TTPP compositions prepared for intradermal assessment in the various in vivo studies presented in this Example are outlined in Tables 6-10 below.

TABLE 6

Compositions for Dose response/Sensitivity assessment

| Sample code | Formulation | dose (μg antigens) | Comments |
|---|---|---|---|
| A1 | PBS, Dextran | 3.00 | 3 fold dilution series |
| A2 | PBS, Dextran | 1.00 | |
| A3 | PBS, Dextran | 0.33 | |
| A4 | PBS, Dextran | 0.11 | |
| A5 | PBS, Dextran | 0.04 | |
| A6 | PBS, Dextran | 0.012 | |

TABLE 7

Compositions for Formulation assessment

| Sample code | Formulation | dose (μg antigens) | Comments |
|---|---|---|---|
| C1 | PBS, Dextran | 3.00 | High |
| C2 | PBS, Dextran | 0.11 | Mid |
| C3 | PBS, Dextran | 0.012 | Low |
| C4 | 2% Ethanol | 3.00 | High |
| C5 | 2% Ethanol | 0.11 | Mid |
| C6 | 2% Ethanol | 0.012 | Low |
| C7 | 10 mM Tris pH 8.5 | 3.00 | High |
| C8 | 10 mM Tris pH 8.5 | 0.11 | Mid |
| C9 | 10 mM Tris pH 8.5 | 0.012 | Low |

TABLE 8

Compositions for Stability assessment

| Sample code | Formulation | dose (μg antigens) | Storage temperature |
|---|---|---|---|
| B1 | PBS, Dextran | 3 | 4° C. |
| B2 | PBS, Dextran | 3 | 25° C. |
| B3 | PBS, Dextran | 3 | 37° C. |

TABLE 9

Compositions for Particle size assessment

| Sample code | Formulation | dose (μg antigens) | Size |
|---|---|---|---|
| B4 | 2% Ethanol | 3 | Large |
| B5 | 2% Ethanol | 3 | Medium |
| B6 | 2% Ethanol | 3 | Small |

TABLE 10

Compositions for Batch variability assessment

| Sample code | Formulation | dose (μg antigens) | Production batch |
|---|---|---|---|
| D1 | PBS, Dextran | 3 | DS498 |
| D2 | PBS, Dextran | 3 | DS504 |
| D3 | PBS, Dextran | 3 | DS507 |
| D4 | PBS, Dextran | 3 | DS560 |
| D5 | PBS, Dextran | 3 | DS585 |
| D6 | PBS, Dextran | 3 | DS625? |

Intradermal Administration

TTPP compositions were administered intradermally according to the following protocol.

Injections of 0.1 mL were made intradermally. Syringes were calibrated to 0.1 mL and the needle of the syringe was 22-26 gauge and 3-4 mm long. Syringes were kept clean and sterilized. Contamination of the syringe with disinfectants or alcohol, which may interfere with testing, was avoided, and care was taken to prevent contamination of vials.

Test Interpretation:

The test was read within 72 hours after injection.

Skin test reactions were classified in accordance with the requirements of the New Zealand Animal Health Board and National Pest Management Strategy for Bovine TB.

Results

In Vivo Functional Characterisation of Tetravalent Polyester Particles

Dose Response.

Figure 10:
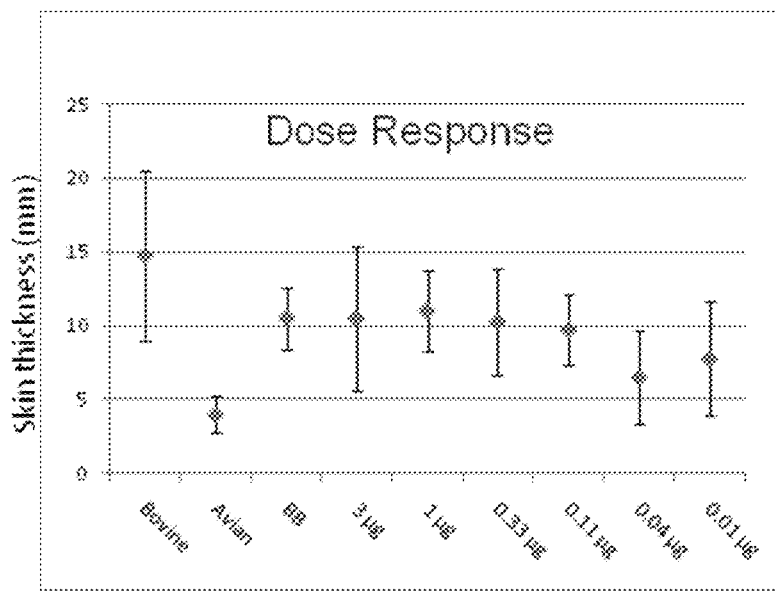

TTPP were effective in eliciting an immune response at doses as low as 0.11 ug, as shown in Table 11 below and in FIG. 10.

TABLE 11

Dose response/Sensitivity to TTPP

| | Skin thickness (mm) | | | | | | | | |
|---|---|---|---|---|---|---|---|---|---|
| | Controls | | Compositions | | | | | | |
| Subject | Bovine (PPDB) | Avian (PPDA) | BB | A1 | A2 | A3 | A4 | A5 | C6 |
| 7258 | 11 | 5 | 8 | 4.5 | 8 | 5 | 7.5 | 0.5 | 1.5 |
| 7202 | 23.5 | 3 | 10.5 | 11 | 14 | 11.5 | 11.5 | 9.5 | 9.5 |
| 7203 | 15.5 | 3.5 | 10.5 | 9.5 | 7.5 | 8.5 | 8 | 5 | 3 |
| 7214 | 8.5 | 2.5 | 14.5 | 19 | 12 | 12 | 12 | 8.5 | 10.5 |
| 7225 | 21 | 5.5 | 11 | 14.5 | 13.5 | 15.5 | 12.5 | 7 | 10 |
| 7229 | 14 | 4.5 | 10 | 10 | 10 | 9 | 7.5 | 6 | 6 |
| Median | 14.75 | 4 | 10.5 | 10.5 | 11 | 10.25 | 9.75 | 6.5 | 7.75 |

Formulation.

TTPP were effective in eliciting an immune response in each of the three formulations (Dextran, Ethanol, Tris) tested, as shown in Table 12 below and in FIG. 11.

TABLE 12

Effect of formulation on immunological response to TTPP

| | Skin thickness (mm) | | | | | | | | | | |
|---|---|---|---|---|---|---|---|---|---|---|---|
| | Controls | | Compositions | | | | | | | | |
| Subject | Bovine (PPDB) | Avian (PPDA) | C1 | C2 | C3 | C4 | C5 | C6 | C7 | C8 | C9 |
| 7223 | 21 | 8.5 | 18 | 9 | 6.5 | 13.5 | 11 | 6.5 | 13.5 | 12.5 | 6.5 |
| 7233 | 27.5 | 4 | 24 | 13 | 11.5 | 24.5 | 11.5 | 9 | 22 | 15.5 | 11 |
| 7201 | 22.5 | 5.5 | 15.5 | 7.5 | 6 | 16 | 9 | 5.5 | 10.5 | 7.5 | 6 |
| 7238 | 13 | 4.5 | 12.5 | 9 | 5 | 13 | 3.5 | 4 | 13.5 | 7.5 | 4 |
| 7224 | 25 | 3 | 12.5 | 13 | 6 | 17.5 | 9 | 2.5 | 14.5 | 5.5 | 2.5 |
| 7218 | 36 | 13.5 | 19.5 | 18.5 | 13 | 16.5 | 8.5 | 5 | 25 | 6.5 | 4 |
| Median | 23.75 | 5 | 16.75 | 11 | 6.25 | 16.25 | 9 | 5.25 | 14 | 7.5 | 5 |

Preferred Site of Injection:

Cattle: Caudal fold for the single intradermal test and the cervical site for the comparative cervical test (CCT);

Deer: the mid cervical site for both the single and the CCT. When using the cervical sites, care was required to evenly clip hair close to the skin surface (2 mm or less mean length) prior to injecting. The recommended size of the clipped area was 10×10 cm for each injection site.

Stability/Aggregation.

TTPP were effective in eliciting an immune response even after 6 months storage at 4° C., at 25° C., and at 37° C. (see Table 13 and FIG. 12). Furthermore, immunological efficacy was not impacted by aggregation (80 um, 20 um, 16 um as shown in Table 13 below and in FIG. 12.

TABLE 13

TTPP Stability/aggregation assessment

Skin thickness (mm)

| | Controls | | | | | | Compositions | | |
|---|---|---|---|---|---|---|---|---|---|
| | Bovine | Avian | | | | | | | |
| Subject | (PPDB) | (PPDA) | BB | B1 | B2 | B3 | 80 um | 20 um | 16 um |
| 7217 | 16.5 | 4.5 | 8 | 16 | 8 | 11.5 | 17.5 | 18 | 15.5 |
| 7205 | 21.5 | 5 | 9.5 | 16 | 13 | 13.5 | 17.5 | 5 | 3.5 |
| 7215 | 19.5 | 12 | 12 | 14 | 12 | 13.5 | 10.5 | 12.5 | 17 |
| 7208 | 19.5 | 7.5 | 11.5 | 7.5 | 7 | 12.5 | 8.5 | 12 | 14.5 |
| 7256 | 21.5 | 3.5 | 13.5 | 12 | 15.5 | 1.5 | 16 | 18.5 | 24 |
| Median | 19.5 | 5 | 11.5 | 14 | 12 | 12.5 | 16 | 12.5 | 15.5 |

Particle Size.

The efficacy of TTPP present at average particle sizes of ~16 um to 80 um in different compositions was assessed herein, as shown in FIGS. 13A and 13B. No significant impact of particle size on sensitivity or specificity was observed.

Batch Variability.

The immunological efficacy of TTPP was very consistent and showed little batch-to-batch variation, as shown in Table 14 below and in FIG. 14.

TABLE 14

TTPP batch variability

Skin thickness (mm)

| | Controls | | | | | | | |
|---|---|---|---|---|---|---|---|---|
| | Bovine | Avian | | | Compositions | | | |
| Subject | (PPDB) | (PPDA) | D1 | D2 | D3 | D4 | D5 | D6 |
| 7234 | 21 | 4.5 | 16.5 | 13.5 | 16.5 | 13.5 | 14.5 | 15.5 |
| 7244 | 23 | 7.5 | 15 | 14.5 | 13.5 | 14 | 17 | 22 |
| 7220 | 22 | 7.5 | 6.5 | 6 | 5.5 | 6 | 4 | 4.5 |
| 7240 | 25.5 | 5 | 22.5 | 18 | 22 | 19.5 | 19.5 | 21 |
| 7222 | 16.5 | 5 | 15 | 10.5 | 12 | 14.5 | 15 | 19 |
| 7263 | 26.5 | 7 | 20 | 17.5 | 19.5 | 22 | 21.5 | 20.5 |
| Median | 22.5 | 6 | 15.75 | 14 | 15 | 14.25 | 16 | 19.75 |

Discussion

This example established that tetravalent TB antigen-comprising polymer particles of the invention were effective in eliciting diagnostically informative skin responses in animals when present in compositions of various formulations, at very low doses, and that efficacy was largely unaffected by particle size or aggregation, or production batch.

Example 4

Assessment of Tetravalent PHA Polymer Particles as Diagnostic Reagents

This example describes further assessment of TTPP of the invention as diagnostic reagents for *tuberculosis*. The sensitivity and selectivity of the TTPP of the invention was assessed in bovine interferon-gamma assays.

Materials and Methods

The materials and methods used in this study were as described in Example 3 above, with the addition of the following.

Lipopolysaccharide-free *E. coli* (ClearColi®, Lucigen) was used as an additional production host for the preparation of TTPP.

Assessment of TB Antigen Reactivity—IFN-γ Assays.

To test the sensitivity and specificity of the TTPP, blood samples were obtained from TB-infected and non-infected cattle, and assayed using IFN-γ specific ELISA in multiwell plates and absorbance measured at 450 nm.

The following reagents were assayed: various dilutions of compositions comprising TTPP expressed in LPS+ and LPS-free *E. coli* (undiluted, 1/4, 1/16, 1/64, and 1/256 dilutions, providing 0.38 μg, 0.1 μg, 25 ng, 6 ng, and 1.5 ng total antigen in-well, respectively), PhaC-only control particles (¼ dilution, providing the same amount of PhaC protein in-well as undiluted tetravalent polymer particles), soluble ESAT6/CFP10 peptide (4 μg protein in-well), PPDB (20 μg protein in-well), PPDA (20 μg protein in-well), and a PBS buffer-only control, were assayed.

Blood Sample Preparation and IFN-γ Assay

The IFN-γ assays used in this example were conducted using sterile consumables under aseptic conditions, on unrefrigerated blood samples, as follows.

1. Mix blood gently by inversion 10 times.
2. Add 1 ml of fresh blood (<6 h post collection) to sterile 48 well plate.
3. Add 700 of tetravalent TB-antigen particles (~6 ng total antigens per mL, or if a 4-fold dilution is used ~1.5 ng/mL), or controls (PBS, $dH_2O$, PPDA, PPDB, etc).
4. Incubate at 37° C. for 20 hours in humidified air with 5% $CO_2$.
5. Centrifuge and collect plasma.
6. Measure IFN-γ levels using a sandwich ELISA kit (Bovigam (Prionics AG)).

Results

As can be seen in Table 15 below and in FIG. 15, substantial IFN-γ responses were observed in blood samples from infected animals receiving as little as 1.5 ng of total antigen when presented on the TTPP of the invention. This response was highly selective, as negative responses were observed with TTPP at all but the highest concentrations in blood samples from non-infected bovine, as shown in Table 15 and FIG. 16. Similar results were obtained irrespective of whether the TTPP of the invention were expressed in LPS+ or LPS− production hosts.

TABLE 15

Tetravalent TB antigen-comprising particles - IFN-γ assays.

| Controls | | Absorbance (450 nm) | | | | |
|---|---|---|---|---|---|---|
| Group | Animal | PBS | PPDA | PPDB | ESAT6/CFP10 | PhaC (1/4) |
| infected | 7202 | 0.007 | 0.357 | 0.668 | 0.454 | 0.404 |
|  | 7203 | 0.004 | 0.295 | 0.660 | 0.428 | 0.080 |
|  | 7205 | 0.019 | 1.155 | 2.620 | 2.034 | 1.183 |
|  | 7208 | 0.029 | 1.169 | 3.099 | 2.465 | 0.251 |
|  | 7214 | 0.009 | 3.385 | 2.788 | 2.086 | 0.601 |
|  | 7215 | 0.017 | 1.593 | 0.895 | 0.249 | 0.110 |
|  | 7217 | 0.005 | 0.641 | 1.949 | 1.465 | 0.300 |
|  | 7225 | 0.015 | 0.573 | 1.739 | 1.738 | 1.061 |
|  | 7229 | 0.185 | 1.859 | 1.468 | 1.419 | 0.997 |
|  | 7256 | 0.837 | 2.628 | 3.930 | 3.957 | 3.129 |
|  | 7258 | 0.631 | 3.218 | 3.773 | 3.554 | 0.774 |
| non infected | 1 891 | 0.016 | 1.012 | 0.220 | 0.065 | 0.283 |
|  | 2 227 | 0.010 | 0.242 | 0.031 | 0.016 | 0.161 |
|  | 3 424 | 0.005 | 0.092 | 0.031 | 0.009 | 0.230 |
|  | 4 422 | 0.011 | 0.119 | 0.041 | 0.007 | 0.145 |
|  | 5 156 | 0.003 | 0.700 | 0.159 | 0.073 | 0.775 |
|  | 6 115 | 0.006 | 0.024 | 0.015 | 0.010 | 0.063 |
|  | 7 904 | 0.009 | 0.050 | 0.023 | 0.008 | 0.055 |
|  | 8 909 | 0.006 | 0.052 | 0.035 | 0.013 | 0.083 |
|  | 9 425 | 0.006 | 0.007 | 0.007 | 0.005 | 0.030 |
|  | 10 291 | 0.005 | 0.021 | 0.009 | 0.004 | 0.025 |

| Tetravalent particles | | Absorbance (450 nm) | | | | | | | | |
|---|---|---|---|---|---|---|---|---|---|---|
| Group | Animal | LPS + 1 | LPS + 1/4 | LPS + 1/16 | LPS + 1/64 | LPS + 1/256 | LPS − 1 | LPS − 1/4 | LPS − 1/16 | LPS − 1/64 | LPS − 1/256 |
| infected | 7202 | 1.620 | 1.546 | 1.173 | 0.705 | 0.424 | 1.990 | 1.917 | 1.415 | 1.112 | 0.491 |
|  | 7203 | 1.110 | 1.134 | 0.987 | 0.568 | 0.441 | 1.068 | 0.961 | 1.022 | 0.897 | 0.558 |
|  | 7205 | 3.349 | 3.361 | 2.979 | 2.406 | 1.592 | 3.398 | 3.148 | 2.749 | 2.968 | 1.585 |
|  | 7208 | 3.365 | 3.742 | 3.359 | 2.873 | 1.740 | 3.675 | 3.784 | 3.675 | 3.601 | 3.011 |
|  | 7214 | 3.958 | 3.793 | 3.851 | 3.314 | 2.911 | 3.650 | 3.617 | 3.055 | 3.234 | 2.753 |
|  | 7215 | 0.259 | 0.306 | 0.312 | 0.268 | 0.137 | 1.474 | 0.468 | 0.365 | 0.337 | 0.241 |
|  | 7217 | 3.053 | 3.579 | 2.986 | 1.664 | 1.086 | 3.805 | 3.710 | 2.441 | 3.957 | 2.138 |
|  | 7225 | 2.582 | 2.790 | 2.538 | 1.959 | 1.353 | 3.122 | 2.729 | 2.092 | 2.426 | 1.689 |
|  | 7229 | 1.288 | 1.763 | 2.038 | 1.364 | 0.814 | 1.029 | 0.778 | 1.298 | 1.908 | 1.647 |
|  | 7256 | 3.467 | 3.659 | 3.709 | 3.560 | 2.956 | 3.874 | 3.808 | 3.846 | 3.890 | 3.818 |
|  | 7258 | 2.884 | 2.890 | 3.313 | 2.800 | 2.451 | 3.655 | 3.648 | 3.609 | 3.720 | 3.619 |
| non infected | 1 891 | 0.191 | 0.224 | 0.140 | 0.090 | 0.044 | 0.450 | 0.209 | 0.225 | 0.183 | 0.085 |
|  | 2 227 | 0.121 | 0.117 | 0.051 | 0.029 | 0.023 | 0.206 | 0.135 | 0.087 | 0.081 | 0.043 |
|  | 3 424 | 0.127 | 0.130 | 0.084 | 0.034 | 0.011 | 0.929 | 0.515 | 0.254 | 0.251 | 0.099 |
|  | 4 422 | 0.072 | 0.048 | 0.027 | 0.017 | 0.013 | 0.047 | 0.032 | 0.022 | 0.010 | 0.003 |
|  | 5 156 | 0.638 | 0.609 | 0.386 | 0.139 | 0.071 | 1.063 | 0.512 | 0.275 | 0.228 | 0.092 |
|  | 6 115 | 0.053 | 0.122 | 0.124 | 0.052 | 0.011 | 0.140 | 0.064 | 0.072 | 0.099 | 0.054 |
|  | 7 904 | 0.035 | 0.029 | 0.022 | 0.015 | 0.019 | 0.096 | 0.040 | 0.020 | 0.017 | 0.014 |
|  | 8 909 | 0.066 | 0.052 | 0.035 | 0.018 | 0.011 | 0.092 | 0.050 | 0.026 | 0.012 | 0.012 |
|  | 9 425 | 0.019 | 0.021 | 0.009 | 0.006 | 0.005 | 0.027 | −0.003 | 0.010 | 0.007 | 0.006 |
|  | 10 291 | 0.017 | 0.022 | 0.014 | 0.005 | 0.004 | 0.049 | 0.018 | 0.009 | 0.006 | 0.003 |

Discussion

This example established that TTPP of the invention were highly sensitive in IFN-γ blood assays, eliciting diagnostically informative responses in samples from infected animals when present at extremely low concentrations (6 ng and 1.5 ng total antigen), and highly specific with no to little responses in samples from non-infected animals.

The tetravalent particles of the invention were diagnostically informative at concentrations orders of magnitude lower than control reagents, such as PPDA and PPDB.

Example 5

Assessment of Tetravalent PHA Polymer Particles—Sensitisation Trial

This example describes a study testing sensitisation to TTPP of the invention.
Materials and Methods A sensitisation study of guinea pigs after injection with TTPP (DS498)) was conducted according to the EU Pharmacopeia method. A test group of "immunised" animals were intradermally injected with tetravalent polymer particles providing 3 μg total antigen (0.1 mL) on days zero, day 5 and day 10. The “immunised” test group and a control group were then intradermally injected with tetravalent polymer particles providing 3 μg total antigen (0.1 mL) on days 25 to 31. All animals were observed for erythema and induration at 24 hours post injection.

Results

No differences between controlled and “immunised” animals were observed, showing that “immunization” with tetravalent polymer particles (3 ug of total antigen) and subsequent skin testing showed that the guinea pigs did not become sensitised. This means that the animals did show immune reactions when injected with the tetravalent polymer particles more than once. Swellings were noticed at the injection sites; however, the absence of sensitisation shows that the tetravalent polymer particles of the invention do not produce a memory immune response which would interefere with a repeated testing regime.

Example 6

Assessment of Tetravalent PHA Polymer Particles—Field Trial

This example describes the assessment of tetravalent polymer particles of the invention as diagnostic reagents for *tuberculosis*. The specificity of the TTPP described in Example 2 above was assessed in large scale field trials in bovine and *cervine* using skin test assays.

Materials and Methods

The materials and methods used in this study were as described in Examples 1 and 2 above, with the addition of the following.

Field Trial 4628 cattle and 4265 deer were administered TTPP and a commercially available TB skin test reagent by intradermal administration, as follows.

Intradermal Administration

The commercially available TB skin test was administered according to the manufacturer's instructions. TTPP compositions were administered intradermally according to the following protocol.

Injections of 0.1 mL (3 μg of total antigen) were made intradermally. Syringes were calibrated to 0.1 mL and the needle of the syringe was 22-26 gauge and 3-4 mm long. Syringes were kept clean and sterilized. Contamination of the syringe with disinfectants or alcohol, which may interfere with testing, was avoided, and care was taken to prevent contamination of vials.

Preferred Site of Injection:

Cattle: Caudal fold for the single intradermal test and the cervical site for the comparative cervical test (CCT);

Deer: the mid cervical site for both the single and the CCT. When using the cervical sites, care was required to evenly clip hair close to the skin surface (2 mm or less mean length) prior to injecting. The recommended size of the clipped area was 10×10 cm for each injection site.

Test Interpretation:

Skin thickness was measured 72 hours after injection.

Skin test reactions were classified in accordance with the requirements of the New Zealand Animal Health Board and National Pest Management Strategy for Bovine TB.

Positive reactors were verified by IFN-γ assay, culture, and PCR assays.

Results

Deer. The 4265 animals were assigned an ID value from 1 to 4265. 63 animals were identified as being positive for TB using the commercially available TB skin test ('Observe'), while 18 animals were identified as positive to TB using the TTPP of the invention.

Observe: observe result with value 1 (n=63) and 0 (n=4202)

TTPP:TTPP result with value 1 (n=18) and 0 (n=4247).

TABLE 16

Paired T-Test and CI: b_TB, Observe - Deer

| | N | Mean | StDev | SE Mean |
|---|---|---|---|---|
| TTPP | 4265 | 0.00422 | 0.06483 | 0.00099 |
| Observe | 4265 | 0.01477 | 0.12065 | 0.00185 |
| Difference | 4265 | −0.01055 | 0.10668 | 0.00163 |

95% CI for mean difference: (−0.01375, −0.00735)

T-Test of mean difference=0 (vs≠0): T-Value=−6.46

P-Value=0.000

Post Hoc Power of the Paired t Test

Testing mean paired difference=0 (versus≠0)

Calculating power for mean paired difference=difference $\alpha$=0.05 Assumed standard deviation of paired differences=0.107

The difference of 0.01 for the sample size of 4265 gives a power for the above test of 0.999983.

Cattle. The 4628 animals were assigned an ID value from 1 to 4628. 76 animals were identified as being positive for TB using the 'Observe' test, while 3 animals were identified as positive to TB using the TTPP of the invention.

Observe: observe result with value 1 (n=76) and 0 (n=4552)

TTPP: TTPP result with value 1 (n=3) and 0 (n=4625).

TABLE 17

Paired T-Test and CI: b_TB, Observe - Cattle

| | N | Mean | StDev | SE Mean |
|---|---|---|---|---|
| TTPP | 4628 | 0.00065 | 0.02545 | 0.00037 |
| Observe | 4628 | 0.01642 | 0.12710 | 0.00187 |
| Difference | 4628 | −0.01577 | 0.12803 | 0.00188 |

95% CI for mean difference: (−0.01946, −0.01208)

T-Test of mean difference=0 (vs≠0): T-Value=−8.38

P-Value=0.000

Post Hoc Power of the Paired t Test

Testing mean paired difference=0 (versus≠0)

Calculating power for mean paired difference=difference $\alpha$=0.05 Assumed standard deviation of paired differences=0.128

The difference of 0.016 for the sample size of 4628 gives a power for the above test of 1.0.

Discussion

The highly statistically significant results presented in this example established that diagnostic assays using TTPP of the invention were highly specific, eliciting accurate diagnostic information and able to discern false positives identified using art standard methods.

Furthermore, the assays presented in Examples 3-6 established that TTPP of the invention were diagnostically informative even at amounts that provided very low total doses of the TB antigens, showing that the TTPP of the invention are highly sensitive, in addition to being highly selective.

INDUSTRIAL APPLICATION

Aspects of the invention described herein, including methods, polymer particles and fusion proteins have utility in the diagnosis, therapy and prevention of *tuberculosis*.

Those persons skilled in the art will understand that the above description is provided by way of illustration only and that the invention is not limited thereto.

PUBLICATIONS

Amara A A, Rehm B H A. 2003. Replacement of the catalytic nucleophile 533 cysteine-296 by serine in class II polyhydroxyalkanoate synthase from *Pseudomonas* 534 *aeruginosa*-mediated synthesis of a new polyester: identification of catalytic residues. 535 Biochem. J. 374: 413-421.

Anderson, P. "*Tuberculosis* vaccines—an update" *Nature* (2007) 5: 484-487

Barnard et al. "High level recombinant protein expression in *Ralstonia eutropha* using T7 RNA polymerase based amplification" *Protein Expr Puri* (2004) 38: 264-71

Barnes and Cave "Current concepts:molecular epidemiology of *tuberculosis*" *New England Journal of Medicine* (2003) 349: 1149-1156

Beach, D. and Nurse. P. "High-frequency transformation of the fission yeast *Schizosaccharomyces pombe*" *Nature* 290: 140-1421981

Belisle, J. T. et al. "*Tuberculosis and the Tubercle Bacillus*" ASM Press, Washington D.C. (2005)

Bowie, J. U. et al "Deciphering the message in protein sequences: tolerance to amino acid substitutions *Science* (1990) 247: 1306-1310

Brockelbank J. A. et al. "Recombinant *Escherichia coli* Strain Produces a ZZ Domain Displaying Biopolyester Granules Suitable for Immunoglobulin G Purification" *Applied and Environmental Microbiology* (2006) 72: 7394-7397

Brunschwig, E and Darzins, A. "A two-component T7 system for the overexpression of genes in *Pseudomonas aeruginosa*" *Gene* (1992) 111: 35-41

Buddle B M, Keen D, Thomson A, Jowett G, McCarthy A R, Heslop J, Delisle G W, Stanford J L, Aldwell F E. 1995. Protection of cattle from bovin *tuberculosis* by vaccination with BCG by the respiratory or subcutaneous route, but not by vaccination with killed *Mycobacterium-vaccae* Res. Vet. Sci. 59:10-16.

Buddle B M, Livingstone P G, Lisle G Wd. 2009. Advances in ante-mortem diagnosis of *tuberculosis* in cattle. New Zealand Veterinary Journal 57:173-180.

Buddle B M, Parlane N A, Keen D L, Aldwell F E, Pollock J M, LighTBody K, Andersen P. 1999. Differentiation between *Mycobacterium bovis* BCG-vaccinated and *M-bovis*-infected cattle by using recombinant mycobacterial antigens. Clinical and Diagnostic Laboratory Immunology 6:1-5.

Casal C, Bezos J, Diez-Guerrier A, Alvarez J, Romero B, de Juan L, 449 Rodriguez-Campos S, Vordermeier M, Whelan A, Hewinson R G, Mateos A, 450 Dominguez L, Aranaz A. 2012. Evaluation of two cocktails containing ESAT-6, 451 CFP-10 and Rv-3615c in the intradermal test and the interferon-gamma assay for 452 diagnosis of bovine *tuberculosis*. Prev. Vet. Med. 105:149-

Case et al., *Proceedings of the National Academy of Science USA* (1979) 76: 5259-5263

Chang et al., Nature, 275: 615 (1978)

DeBoer et al., "The tac promoter: a functional hybrid derived from the trp lac promoters" *Proceedings of the National Academy of Science USA* (1983) 80: 21-25

Fleer, R. et al., "Stable multicopy vectors for high-level secretion of recombinant human serum albumin in *Kluyveromyces* yeasts" *Bio/Technology* 9: 968-975

Friehs & Reardon "Parameters Influencing the Productivity of Recombinant *E. coli* Cultivations". *Advances in Biochemical Engineering Technology* Vol 48 Springer Verlag (1991)

Goeddel, D. V. et al. "Direct expression in *Escherichia coli* of a DNA sequence coding for human growth hormone" (1979) *Nature* 281: 544-548

Goeddel, D. V. "Synthesis of human fibroblast interferon by *E. coli*" *Nucleic Acids Research* (1980) 8: 4057-4074

Hess, B. et al. "Cooperation of glycolytic enzymes" *Advances in Enzyme Regulation* (1968) 7: 149-167.

Hitzeman et al., J. Biol. Chem., 255:2073 (1980)]

Holland, M. J. and Holland, J. P. "Isolation and identification of yeast messenger ribonucleic acids coding for enolase, glyceraldehyde-3-phosphate dehydrogenase, and phosphoglycerate kinase" *Biochemistry* (1978) 17: 4900-4907

Huang, X. "On global sequence alignment" *Computer Application in the Biosciences* (1994) 10: 227-235

Jahns A C, Rehm B H A. 2009. Tolerance of the *Ralstonia eutropha* Class I polyhydroxyalkanoate synthase for translational fusions to its C terminus reveals a new mode of functional display. Appl. Environ. Microbiol. 75:5461-5466.

Kelly, J. M. and Hynes, M. J. "Transformation of *Aspergillus niger* by the amdS 22 gene of *Aspergillus nidulans*" *EMBO Journal* (1985) 4:475-479

Kingsman, A. J. et al., "Replication in *Saccharomyces cerevisiae* of plasmid pBR313 carrying DNA from the yeast trp1 region" *Gene* (1979) 7:141-152

Louvencourt et al. "Transformation of *Kluyveromyces lactis* by killer plasmid DNA" *Journal of Bacteriology* (1983) 154: 737-742

Madison, L. L. et al, "Metabolic Engineering of Poly(3-hydroxyalkanoates): From DNA to Plastic", *Microbiology and Molecular Biology Reviews* (1999) 63: 21-53

Mather, J. P. "Establishment and characterization of two distinct mouse testicular epithelial cell lines" *Biology of Reproduction* (1980) 23: 243-251

Mather, J. P. et al. "Culture of Testicular Cells in Hormone-Supplemented Serum-Free Medium" *Annals of the N.Y. Academy of Science* (1982) 383:44-68

Millington K A, Fortune S M, Low J, Garces A, Hingley-Wilson S M, Wickremasinghe M, Kon O M, Lalvani A. 2011. Rv3615c is a highly immunodominant RD1 (Region of Difference 1)-dependent secreted antigen specific for *Mycobacterium tuberculosis* infection. Proceedings of the National Academy of Sciences of the United States of America 108:5730-5735.

Monaghan M L, Doherty M L, Collins J D, Kazda J F, Quinn P J. 1994. The tuberculin test Veterinary Microbiology 40:111-124.

Mustafa, A. S. "Biotechnology in the development of new vaccines and diagnostic reagents against *tuberculosis*" *Current Pharmaceutical Biotechnology* (2001) 2: 157-173

Parlane N A, Wedlock D N, Buddle B M, Rehm B H A. 2009. Bacterial polyester inclusions engineered to display vaccine candidate antigens for use as a novel class of safe and efficient vaccine delivery agents. Appl. Environ. Microbiol. 503 75:7739-7744.

Peters, V. and Rehm, B. H. A. "In vivo enzyme immobilization by use of engineered polyhydroxyalkanoate synthase" *Applied and Environmental Microbiology* (2006) 72: 1777-83

Peters V, Rehm B H A. 2008. Protein engineering of streptavidin for in vivo assembly of streptavidin beads. Journal of Biotechnology 134:266-274

Rehm, B. H. A. "Polyester synthesis; natural catalysts for plastics" *Biochemical Journal* (2003) 376: 15-33

Rehm, B. H. A. "Biopolyester particles produced by microbes or using polyester synthases: self assembly and potential applications" *Microbial Biotechnology: biological self-assembly systems and biopolymer-based nanostructures* Horizon Bioscience (2006)

Sambrook, et al "*Molecular Cloning; a Laboratory Manual*" (2$^{nd}$ ed) Cold Spring Harbor Press (1987)

Sambrook J. Fritsch E F, Maniatis T. 1989. Molecular cloning: a laboratory manual. Cold Spring Harbor Laboratory Press, New York, USA.

Sidders B, Pirson C, Hogarth P J, Hewinson R G, Stoker N G, Vordermeier H M, Ewer K. 2008. Screening of highly expressed mycobacterial genes identifies Rv3615c as a useful differential diagnostic antigen for the *Mycobacterium tuberculosis* complex. Infectin and Immunity 76:3932-3939.

Spiekermann P, Rehm B H A, Kalscheuer R, Baumeister D, Steinbuchel A. 1999. A sensitive, viable-colony staining method using Nile red for direct screening of bacteria that accumulate polyhydroxyalkanoic acids and other lipid storage compounds. Arch. Microbiol. 171:73-80.

Sreekrishna K et al. "High level expression of heterologous proteins in methylotropic yeast *Pichia pastoris*" *Journal of Basic Microbiology* (1988) 28: 265-278

Stinchcomb, D. T. et al. "Isolation and characterisation of a yeast chromosomal replicator" *Nature* (1979) 282: 39-43

Tilburn, J. et al. "Transformation by integration in *Aspergillus nidulans*" *Gene* (1983) 26: 205-221

Tschemper, G and Carbon, J. "Sequence of a yeast DNA fragment containing a chromosomal replicator and the TRP1 gene" *Gene* (1980) 10:157-166

Urlaub, G. and Chasin, L. A. "Isolation of Chinese hamster cell mutants deficient in dihydrofolate reductase activity" *Proceedings of the National Academy of Science USA* (1980) 77:4216-4220.

Van den Berg, G. et al. "*Kluyveromyces* as a host for heterologous gene expression: expression and secretion of prochymosin" *Bio/Technology* (1990) 8: 135-139.

Vordermeier H M, Whelan A, Cockle P J, Farrant L, Palmer N, Hewinson R G. 2001. Use of synthetic peptides derived from the antigens ESAT-6 and CFP-10 for differential diagnosis of bovine *tuberculosis* in cattle. Clinical and Diagnostic Laboratory Immunology 8:571-578.526

Waters W R, Nonnecke B J, Palmer M V, Robbe-Austermann S, Bannantine J P, Stabel J R, Whipple D L, Payeur J B, Estes D M, Pitzer J E, Minion F C. 2004. Use of recombinant ESAT-6: CFP-10 fusion protein for differentiation of infections of cattle by *Mycobacterium bovis* and by *M. avium* subsp *avium* and *M. avium* subsp *paratuberculosis*. Clinical and Diagnostic Laboratory Immunology 11:729-735.

Whelan A O, Clifford D, Upadhyay B, Breadon E L, McNair J, Hewinson G R, 445 Vordermeier M H. 2010. Development of a skin test for bovine *tuberculosis* for differentiating infected from vaccinated animals. Journal of Clinical Microbiology 48:3176-3181.

Yelton, M. M. et al. "Transformation of *Aspergillus nidulans* by using a trpC plasmid" *Proceedings of the National Academy of Science USA* (1984) 81: 1470-1474

All patents, publications, scientific articles, web sites, and other documents and materials referenced or mentioned herein are indicative of the levels of skill of those skilled in the art to which the invention pertains, and each such referenced document and material is hereby incorporated by reference to the same extent as if it had been incorporated by reference in its entirety individually or set forth herein in its entirety. Applicants reserve the right to physically incorporate into this specification any and all materials and information from any such patents, publications, scientific articles, web sites, electronically available information, and other referenced materials or documents.

The written description portion of this patent includes all claims. Furthermore, all claims, including all original claims as well as all claims from any and all priority documents, are hereby incorporated by reference in their entirety into the written description portion of the specification, and Applicants reserve the right to physically incorporate into the written description or any other portion of the application, any and all such claims. Thus, for example, under no circumstances may the patent be interpreted as allegedly not providing a written description for a claim on the assertion that the precise wording of the claim is not set forth in haec verba in written description portion of the patent.

All of the features disclosed in this specification may be combined in any combination. Thus, unless expressly stated otherwise, each feature disclosed is only an example of a generic series of equivalent or similar features.

It is to be understood that while the invention has been described in conjunction with the detailed description thereof, the foregoing description is intended to illustrate and not limit the scope of the invention, which is defined by the scope of the appended claims. Thus, from the foregoing, it will be appreciated that, although specific nonlimiting embodiments of the invention have been described herein for the purpose of illustration, various modifications may be made without deviating from the spirit and scope of the invention. Other aspects, advantages, and modifications are within the scope of the following claims and the present invention is not limited except as by the appended claims.

The specific methods and compositions described herein are representative of preferred nonlimiting embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. Thus, for example, in each instance herein, in nonlimiting embodiments or examples of the present invention, the terms "comprising", "including", "containing", etc. are to be read expansively and without limitation. The methods and processes illustratively described herein suitably may be practiced in differing orders of steps, and that they are not necessarily restricted to the orders of steps indicated herein or in the claims.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by various nonlimiting embodiments and/or preferred nonlimiting embodiments and optional features, any and all modifications and variations of the concepts herein disclosed that may be resorted to by those skilled in the art are considered to be within the scope of this invention as defined by the appended claims.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

It is also to be understood that as used herein and in the appended claims, the singular forms "a," "an," and "the" include plural reference unless the context clearly dictates otherwise, the term "X and/or Y" means "X" or "Y" or both "X" and "Y", and the letter "s" following a noun designates both the plural and singular forms of that noun. In addition, where features or aspects of the invention are described in terms of Markush groups, it is intended, and those skilled in the art will recognize, that the invention embraces and is also thereby described in terms of any individual member and any subgroup of members of the Markush group, and applicants reserve the right to revise the application or claims to refer specifically to any individual member or any subgroup of members of the Markush group.

The invention claimed is:

1. A method of diagnosing tuberculosis in a subject, the method comprising administering to the subject an effective amount of at least one polymer particle comprising one or more fusion polypeptides, wherein one or more of the fusion polypeptides comprise a particle-forming protein and three or more selected from the group consisting of:

a. an ESAT6 antigen;

b. a CFP10 antigen, c. an Rv3615c antigen, d. an Rv3020c antigen, and e. an Rv2346c antigen, and detecting an immune response in the subject, wherein the presence of an immune response is indicative of tuberculosis.

2. The method of claim 1, wherein the method is a method of detecting *M. tuberculosis* or *M. bovis* in a subject.

3. The method of claim 1, wherein the administration is topical.

4. The method of claim 1, wherein the administration is by skin prick.

5. The method of claim 1, wherein the administration is of a diagnostic reagent, and the diagnostic reagent comprises less than 5 μg of each antigen present per dose.

6. The method of claim 5, wherein the diagnostic reagent comprises less than 5 μg total antigen per dose.

7. The method of claim 5, wherein the diagnostic reagent comprises less than 1 μg of each antigen present per dose.

8. A method of detecting *M. tuberculosis* or *M. bovis* in a subject, the method comprising:

providing a sample from a subject, contacting the sample with at least one polymer particle comprising one or more fusion polypeptides, wherein one or more of the fusion polypeptides comprise a particle-forming protein and three or more selected from the group consisting of:

a. an ESAT6 antigen;

b. a CFP10 antigen, c. an Rv3615c antigen, d. an Rv3020c antigen, and e. an Rv2346c antigen, and detecting a response indicative of exposure of the subject to one or more *M. tuberculosis* or *M. bovis* antigens, wherein the response is indicative of *M. tuberculosis* or *M. bovis* in the subject.

9. The method of claim 8, wherein the detection of the response is the detection of interferon-gamma.

10. The method of claim 8, wherein the detection is by a cell proliferation assay, a cell sorting assay, fluorescence-activated cell sorting (FACS), an in situ hybridisation assay, an immunoassay, an enzyme-linked immunosorbent assay (ELISA), a radioimmunoassay, a Western Blot, or a cytokine assay.

* * * * *